United States Patent [19]

Harada et al.

[11] Patent Number: 5,686,066
[45] Date of Patent: Nov. 11, 1997

[54] POLYASPARTIC ACID ZWITTERIONIC DERIVATIVES, PREPARATION PROCESSES THEREOF, HAIR-TREATING COMPOSITIONS AND COSMETIC COMPOSITIONS

[75] Inventors: Yukiko Harada; Hosei Shinoda; Makoto Sukegawa; Hiroaki Tamatani, all of Kanagawa, Japan

[73] Assignee: Mitsui Toatsu Chemicals, Inc., Tokyo, Japan

[21] Appl. No.: 723,247

[22] Filed: Sep. 30, 1996

[30] Foreign Application Priority Data

Oct. 5, 1995 [JP] Japan ................................. 7-258969

[51] Int. Cl.$^6$ .................. C08F 283/06; C08G 68/48; C08L 77/04; A61K 7/11
[52] U.S. Cl. ............... 424/70.14; 424/78.3; 424/70.17; 424/DIG. 1; 424/DIG. 2; 525/420; 528/328; 528/363
[58] Field of Search ...................... 424/401, 78.3, 424/70.14, 70.17, DIG. 1, DIG. 2; 525/420; 528/328, 363

[56] References Cited

U.S. PATENT DOCUMENTS

| | | |
|---|---|---|
| 3,846,380 | 11/1974 | Fujimoto et al. . |
| 3,927,204 | 12/1975 | Neri et al. . |
| 3,948,863 | 4/1976 | Akamatsu et al. . |
| 4,284,755 | 8/1981 | Lohse et al. . |
| 4,363,797 | 12/1982 | Jacquet et al. . |
| 5,175,285 | 12/1992 | Lehmann et al. . |
| 5,461,085 | 10/1995 | Nagatomo et al. . |
| 5,571,889 | 11/1996 | Katoh et al. . |

FOREIGN PATENT DOCUMENTS

| | | |
|---|---|---|
| 63-35698 | 2/1968 | Japan . |
| 55-17009 | 5/1980 | Japan . |
| 56-92809 | 7/1981 | Japan . |
| 57-48335 | 3/1982 | Japan . |
| 59-209635 | 11/1984 | Japan . |
| 62-32165 | 7/1987 | Japan . |
| 1-213219 | 8/1989 | Japan . |
| 2-222421 | 9/1990 | Japan . |
| 6-248072 | 9/1994 | Japan . |
| 7-277916 | 10/1995 | Japan . |

*Primary Examiner*—Edward J. Webman
*Attorney, Agent, or Firm*—Burns, Doane, Swecker & Mathis

[57] ABSTRACT

Disclosed are polymers (polyaspartic acid Zwitterionic derivatives) containing, in the molecule, 1 mol % or more of at least one repeating unit selected from the group consisting of repeating units represented by the following formulas (1) and (2).

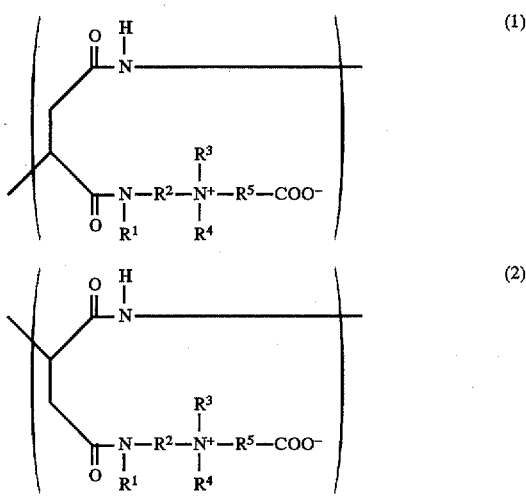

These polymers are useful in the preparation of hair-treating compositions and cosmetic compositions having excellent hairdressing properties and good biocompatibility.

23 Claims, No Drawings

POLYASPARTIC ACID ZWITTERIONIC DERIVATIVES, PREPARATION PROCESSES THEREOF, HAIR-TREATING COMPOSITIONS AND COSMETIC COMPOSITIONS

BACKGROUND OF THE INVENTION i) Field of the Invention

This invention relates to polymers (for example, polyaspartic acid derivatives) consisting at least partly of repeating units having a pendant group including a betaine structure, processes for preparing these derivatives, and hair-treating compositions and cosmetic compositions containing these polymers.

ii) Description of the Prior Art

Hair-treating agents (e.g., set lotions and hair sprays) consisting essentially of synthetic polymeric compounds are superior to oily cosmetics in that the former compositions shows less stickiness during use and can be easily removed by hair washing. As these synthetic polymeric compounds, nonionic, anionic and cationic polymeric compounds are being used. However, nonionic polymers are problematic, for example, in that they are subject to a flaking phenomenon and have weak hair-setting power under high-temperature and high-humidity conditions. Anionic polymers are superior to nonionic polymers in hair-setting power under high-temperature and high-humidity conditions, but still have the disadvantage that they have a low affinity for the hair and are not adapted well to the hair and that the addition of a cationic material is limited because an excessive amount of a cationic material may produce a precipitate. Similarly to nonionic polymers, cationic polymers have weak hair-setting power under high-temperature and high-humidity conditions and, moreover, involve the problem of toxicity and skin irritation because of their cationic properties. In view of these circumstances, hair-treating agents have been extensively investigated and developed as described below.

Japanese Patent Publication No. 17009/'80 discloses an amphoteric monochloroacetate ion-containing polymeric compound which consists of a dimethylaminoethyl methacrylate/ethyl acrylate/butyl methacrylate copolymer and can be suitably applied to aerosol type hairdressings. Moreover, Japanese Patent Publication No. 32165/'87 discloses an amphoteric ion-containing polymeric compound (e.g., N-methacryloylethyl-N,N-dimethylammonium-α-N-methylcarboxybetaine methacrylate) which can be suitably applied to hair cosmetics. However, these hair-treating agents do not have sufficient hair-setting power under high-humidity conditions. Moreover, these amphoteric ion-containing polymeric compounds are problematic in that their safety for the living body cannot be said to be sufficient and, when the residue resulting from treatment therewith is released to the natural world (e.g., rivers), they hardly decompose and tend to accumulate in the environment.

The amphoteric ion-containing polymer disclosed in Japanese Patent Laid-Open No. 92809/'81 is suitable for use in aerosol sprays using a halogenated hydrocarbon as propellant. However, when this amphoteric ion-containing polymer is used in a new type of aerosol sprays using, in pace of the halogenated hydrocarbon, a hydrogen (e.g., propane or butane) as propellant owing to the problem of environmental protection, the presence of the hydrocarbon causes a reduction in the solubility of the polymer in the polymer solution (using an alcohol or the like as solvent), so that the solution may become inhomogeneous and/or the polymer may separate out. As a result, there is a possibility that the spray may form a non-uniform film and/or cause a clogging of the valve.

Japanese Patent Publication No. 213219/'89 discloses an amphoteric ion-containing acrylic resin obtained by reacting a copolymer of a dimethylaminoalkyl acrylate and an acrylic acid long-chain alkyl ester with an alkali metal salt of haloacetic acid. However, this amphoteric ion-containing acrylic resin cannot be said to have sufficient safety for the living body. Moreover, this amphoteric ion-containing acrylic resin is problematic in that it hardly decomposes under natural environmental conditions because it is a polymeric compound having carbon-to-carbon bonds in the main skeleton, and it tends to accumulate in the environment when the resulting washings and the like are released to the natural world (e.g., rivers).

Under these circumstances, there has been a demand for the development of hair-treating compositions which meet various performance requirements for hair-treating agents, exhibit excellent hairdressing properties (in particular, excellent both set-keeping capacity in a highly humid state and good biocompatibility during use), and are not detrimental to the environment because they decompose easily after being used or dumped.

Meanwhile, with regard to cosmetics, techniques for the application of water-soluble polyamino acids have been investigated and developed as described below.

In Japanese Patent Laid-Open No. 209635/'84, it is disclosed that, when polyglutamic acid salts are used as humectants for cosmetic purposes, they impart moderate moisture and smoothness to the skin and have the effect of preventing the skin from becoming chapped. However, polyglutamic acid has the disadvantage that its moisture retention properties have pH dependence and, therefore, satisfactory moisture retention is not achieved at pH levels other than neutral.

In Japanese Patent Laid-Open No. 277916/'95, it is disclosed that cosmetics having a moist and smooth feeling can be obtained by incorporating therein polyaspartic acid, as well as amino acids, pyrrolidonecarboxylic acid and glycine betaine. However, these cosmetics have the disadvantage that they have an insufficient affinity for the skin and the hair and give a feeling of stickiness under high-humidity conditions.

Japanese Patent Laid-Open No. 35698/'88 discloses a surfactant composition having incorporated therein at least one skin irritation inhibitor selected from polyglutamic acid and salts thereof, and polyaspartic acid and salts thereof. It is disclosed in U.S. Pat. No. 3,846,380 that polyaspartic acid derivatives having a hydrophobic group and a hydrophilic group in the side chains are used as a surfactant. Moreover, it is disclosed in U.S. Pat. No. 4,363,797 that polyaspartic acid derivatives having a thiol group are suitable for use in such applications as shampoos, lotions, dyes and baths, and are used for hair cosmetics with a polymer based on poly-β-alanine. Furthermore, it is disclosed in Japanese Patent Laid-Open No. 248072/'94 that water-soluble polyamino acid derivatives having a thiol group and/or a disulfide group are suitable for use in such applications as shampoos, hair cream, hair lotions and hair brushing aids. However, cosmetics using these polyamino acids have no hair-setting power.

In Japanese Patent Laid-Open No. 48335/'82, it is disclosed that an amphoteric ion-containing polymeric compound derived from methacrylic acid can be used as a dispersion stabilizer in order to disperse an iridescent agent finely and stably in shampoo compositions. However, this amphoteric ion-containing polymeric compound is problematic in that its safety for the living body cannot be said to be sufficient and in that it hardly decomposes under natural environmental conditions and tends to accumulate in the environment.

Thus, there has been known no cosmetic composition that meets various performance requirements for cosmetics, exhibits excellent hairdressing properties (in particular, excellent both set-keeping capacity in a highly humid state and good biocompatibility during use), and is not detrimental to the environment because it decompose easily after being used or dumped.

SUMMARY OF THE INVENTION

A first object of the present invention is to provide polymers useful in the preparation of hair-treating compositions, cosmetic compositions and the like, the polymers being characterized in that, during use, they are expected to exhibit excellent hairdressing properties (in particular, excellent set-keeping capacity in a highly humid state), good biocompatibility with the living body (including, for example, biocompatibility with the eyes and skins of experimental animals such as mice, rats and rabbits) and low mutagenicity, and in that they are not detrimental to the environment because they decompose easily after being used or dumped.

A second object of the present invention is to provide processes for preparing polymers having the above-described excellent properties in an easy and satisfactory manner.

The above-described first object is accomplished by a polymer containing, in the molecule, 1 mol % or more of at least one repeating unit selected from the group consisting of repeating units represented by the following formulas (1) and (2).

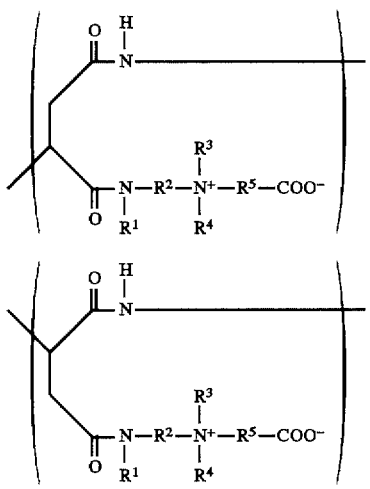

where $R^1$ is a hydrogen atom or a lower hydrocarbon radical of 1 to 6 carbon atoms, $R^2$ and $R^5$ are each independently a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom.

The second object of the present invention is accomplished by a process for the preparation of said polymer of the present invention, which comprises the steps of reacting polysuccinimide of formula (12)

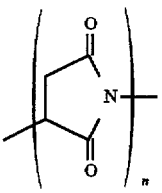

with at least one compound selected from the group consisting of amines of formula (13)

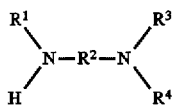

where $R^1$ is a hydrogen atom or a lower hydrocarbon radical of 1 to 6 carbon atoms, $R^2$ is a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, and salts thereof, and making the resulting product amphoteric by reaction with a halogenated fatty acid salt of formula (14)

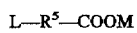

where L is a halogen atom, $R^5$ is a saturated or unsaturated hydrocarbon radical of 1 to 24 carbon atoms, and M is a hydrogen atom, an alkali metal atom or an alkaline earth metal atom.

The second object of the present invention is also accomplished by a process for the preparation of said polymer of the present invention, which comprises the steps of reacting polysuccinimide of said formula (12) with at least one compound selected from the group consisting of amines containing amphoteric ion of formula (15),

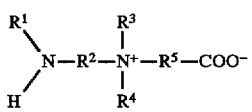

where $R^1$ is a hydrogen atom or a lower hydrocarbon radical of 1 to 6 carbon atoms, $R^2$ and $R^5$ are each independently a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, and salts thereof.

The novel polymers of the present invention have good biocompatibility and high decomposability and, at the same time, consist at least partly of repeating units having a pendant group including a specific betaine structure as represented by formulas (1) and (2), so that they exhibit excellent hairdressing properties (in particular, excellent set-keeping capacity in a highly humid state). When they are used for hair-treating compositions, cosmetic compositions and the like, they effect in good humectant, flexibilty of formed film, smoothness and natural softness after hair treatment. Furthermore, they show good workability for preparing hair-treating compositions and cosmetic compositions.

DESCRIPTION OF THE PREFERRED EMBODIMENTS

[Polymers (polyaspartic acid derivatives)]

The polymers of the present invention contain, in the molecule, 1 mol % or more of at least one repeating unit selected from the group consisting of repeating units represented by the above formulas (1) and (2). These repeating units are obtained by chemical modification of repeating units of a polysuccinimide derived by the condensation reaction of aspartic acid or a salt thereof. Although there is no limitation for preparation process for the polymers of the present invention, these are typicaly polyaspartic acid derivatives. In the following description, the polymers of the present invention are abbreviated by polyaspartic acid derivatives. As used herein, the term "hydrocarbon radical" comprehends straight-chain, branched and cyclic hydrocarbon radicals and, moreover, substantial hydrocarbon radicals containing atoms others than C and H (e.g., N, O and S) in the atomic group. For example, the "hydrocarbon radical" containis a hydrocarbon radical having carboxy, amino, hydroxy or ester groups.

The substituent groups present in formulas (1) and (2) are defined as described below.

$R^1$ is a hydrogen atom or a lower hydrocarbon radical of 1 to 6 carbon atoms. Specific examples of $R^1$ include hydrogen atom; alkyl groups such as methyl, ethyl, propyl, butyl; hydroxyalkyl groups such as hydroxymethyl, hydroxyethyl, hydroxypropyl and hydroxybutyl; and the like. Among them, hydrogen atom, methyl, ethyl, hydroxymethyl and hydroxyethyl are preferred, hydrogen atom, methyl and ethyl are more preferred, and hydrogen atom is most preferred.

$R^2$ and $R^5$ are each independently a saturated or unsaturated hydrocarbon radical of 1 to 24 carbon atoms. Specific examples of $R^2$ and $R^5$ include alkylene groups such as methylene, ethylene, trimethylene, tetramethylene, pentamethylene, hexamethylene, dodecylene and octadecylene; cycloalkylene groups such as cyclobutylene, cyclopentylene and cyclohexylene; hydroxyalkylene groups such as hydroxyethylene, hydroxytrimethylene, hydroxytetramethylene, hydroxypentamethylene, hydroxyhexamethylene; and alkenylene groups such as vinylene, propenylene, butenylene, pentenylene, hexenylene, tridecenylene, tetradecenylene, hexadecenylene, octadecenylene; and the like. Other specific examples thereof include azaalkylene and azaalkenylene groups such as azatetramethylene and azapentamethylene; oxaalkylene and oxaalkenylene groups such as oxatrimethylene, oxatetramethylene and oxapentamethylene; and thioalkylene and thioalkenylene groups such as thiotetramethylene and thiopentamethylene.

Among them, as $R^2$ and $R^5$, alkylene, hydroxyalkylene and alkenylene groups of 1 to 18 carbon atoms are preferred. As $R^2$, alkylene and hydroxyalkylene groups of 1 to 5 carbon atoms are more preferred. As $R^5$, alkylene and hydroxyalkylene groups of 1 to 5 carbon atoms; and alkylene, hydroxyalkylene, and alkenylene groups of 12 or 18 carbon atoms are more preferred. In particular, as $R^2$, trimethylene is most preferred, and as $R^5$, methylene, ethylene, dodecylene and octadecylene are most preferred.

$R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom. Specific examples of $R^3$ and $R^4$ include alkyl groups such as methyl, ethyl, propyl, butyl, pentyl, hexyl, dodecyl and octadecyl; cycloalkyl groups such as cyclobutyl, cyclopentyl and cyclohexyl; hydroxyalkyl groups such as hydroxymethyl, hydroxyethyl, hydroxypropyl, hydroxybutyl, hydroxypentyl, hydroxyhexyl, hydroxydodecyl and hydroxyoctadecyl; and alkenyl groups such as propenyl, butenyl, pentenyl, hexenyl, heptenyl, tridecenyl, tetradecenyl, hexadecenyl and octadecenyl; and the like. Other specific examples thereof include azaalkyl and azaalkenyl groups such as azapropyl, azatetramethyl, azapentyl and azahexyl; oxaalkyl and oxaalkenyl groups such as oxaethyl, oxapropyl, oxatetramethy, oxapentyl, oxahexyl, oxaheptyl, oxaoctyl; and thioalkyl and thioalkenyl groups such as thiotetramethyl, thiopentamethyl, thio hexyl, thioheptyl and thiooctamthyl.

Among them, alkyl, hydroxyalkyl and alkenyl groups of 1 to 18 carbon atoms are preferred. More specifically, alkyl and hydroxyalkyl groups of 1 to 6 carbon atoms; and alkyl and alkenyl groups of 12 or 18 carbon atoms are more preferred, methyl, ethyl, propyl, dodecyl, octadecyl and octadecenyl are most preferred.

When $R^3$ and $R^4$ are bonded together to form a six members ring containing nitrogen atom, that is, a six members ring containing nitrogen atom which bonded by $R^3$ and $R^4$ each is formed, a ring formed by various groupes above-described is preferred. The ring may contain the other atoms than the nitrogen atom. Piperazine ring, piperidine ring and morphorine ring are more preferred, and morphorine ring is most preferred.

On the other hand, it is preferable that $R^1$ is a hydrogen atom, $R^2$ is a saturated hydrocarbon radical of 1 to 5 carbon atoms, $R^5$ is a saturated hydrocarbon radical of 1 to 5 carbon atoms or a saturated or an unsaturated hydrocarbon radical of 12 or 18, and $R^3$ and $R^4$ are each independently a saturated hydrocarbon radical of 1 to 6 carbon atoms in formulas (1) and (2).

It is preferable that the polymer of the present invention contains, in the molecule, 1 mol % or more of at least one repeating unit selected from the group consisting of repeating units represented by the formulas (1) and (2), and further contains, in the molecule, 99 mol % or less of at least one repeating unit selected from the group consisting of repeating units represented by the following formulas (3) and (4).

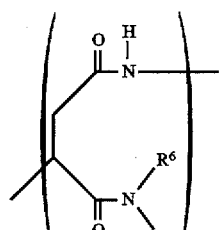

(3)

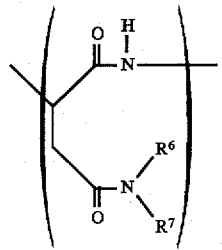

(4)

where $R^6$ and $R^7$ are each independently a hydrogen atom, or a saturated or unsaturated hydrocarbon radical of 1 to 24 carbon atoms in which $R^6$ and $R^7$ may be bonded together to form a six members ring containing nitrogen atom.

When the polymer of the present invention contains repeating units having a hydrophobic group as a pendant group shown by formulas (3) and (4), the effect of hairdressing properties (in particular, excellent both set-keeping capacity in a highly humid state) is further remarkable. It is preferable that $R^6$ and $R^7$ are each independently a hydrogen atom, or a saturated or unsaturated hydrocarbon radical of 4 to 18 carbon atoms in formulas (3) and (4).

Specific examples of $R^6$ and $R^7$ in formulas (3) and (4) are the same as that above-described as examples (and six members rings) of $R^3$ and $R^4$ in formulas (1) and (2), except that, as $R^6$ and $R^7$ in formulas (3) and (4), it is preferable that one of $R^6$ and $R^7$ is a hydrogen atom, and the other is an alkyl, hydroxyalkyl, alkenyl or oxaalkyl group of 7 to 18 carbon atoms, more preferably, butyl, isobutyl, hexyl, dodecyl, oxahexyl, oxadodecyl, octadecyl or octadecenyl.

It is preferable that the polymer of the present invention contains, in the molecule, 1 mol % or more of at least one repeating unit selected from the group consisting of repeating units represented by the formulas (1) and (2), and, as the rest, further contains, in the molecule, 99 mol % or less of at least one repeating unit selected from the group consisting of repeating units represented by the following formulas (5) to (9), while the repeating units of (3) and (4).

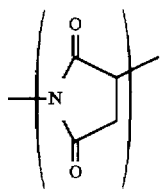
(5)

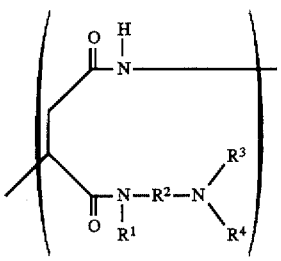
(6)

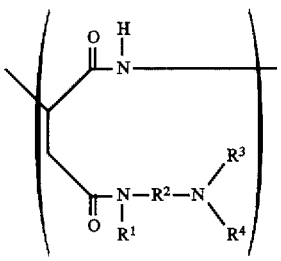
(7)

where $R^1$ is a hydrogen atom or a lower hydrocarbon radical of 1 to 6 carbon atoms, $R^2$ is a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom;

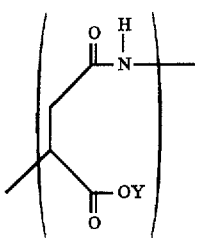
(8)

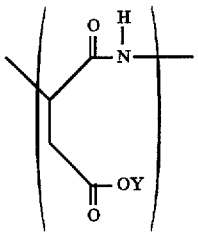
(9)

where Y is a hydrogen atom, an alkali metal atom or an alkaline earth metal atom.

It is preferable that $R^1$ is a hydrogen atom, $R^2$ is a saturated hydrocarbon radical of 1 to 5 carbon atoms, and $R^3$ and $R^4$ are each independently a saturated hydrocarbon radical of 1 to 6 carbon atoms or a saturated or unsaturated hydrocarbon radical of 12 or 18 in formulas (6) and (7).

Specific examples of $R^1$, $R^2$, $R^3$ and $R^4$ in formulas (6) and (7) are the same-as those above-described as examples (and six members rings) of $R^1$, $R^2$, $R^3$ and $R^4$ in formulas (1) and (2), except that, preferable examples of $R^3$ and $R^4$ in formulas (6) and (7) include hydrogen atom.

Specific examples of Y in formulas (8) and (9) include hydrogen atom; alkali metal atoms such as sodium, lithium, potassium; alkaline earth metal atoms such as calcium, barium, magunesium; and the like. Among them, hydrogen atom, sodium, potassium, calcium and magunesium are preferred.

It is preferable that the polymer of the present invention contains, in the molecule, 1 mol % or more of at least one repeating unit selected from the group consisting of repeating units represented by the formulas (1) and (2), and, as the rest, further contains, in the molecule, at least one repeating unit selected from the group consisting of repeating units represented by the following formulas (10) and (11), while the repeating units of (3) and (4).

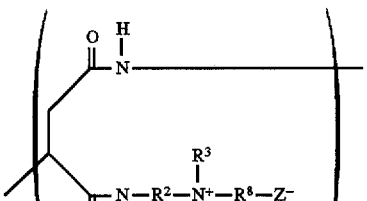
(10)

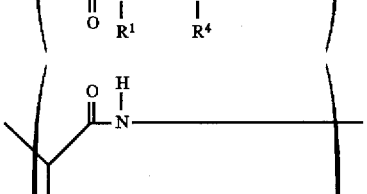
(11)

where $R^1$ is a hydrogen atom or a lower hydrocarbon radical of 1 to 6 carbon atoms, $R^2$ is a saturated or unsaturated hydrocarbon radical of 1 to 24 carbon atoms, $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, $R^8$ is a hydrogen atom, or a saturated or unsaturated hydrocarbon radical of 1 to 24 carbon atoms, and $Z^-$ is an anion derived from an organic or inorganic acid.

Specific examples of $R^1$, $R^2$ $R^3$ and $R^4$ in formulas (10) and (11) are the same as that above-described as examples (and six members rings) of $R^1$, $R^2$ $R^3$ and $R^4$ in formulas (1) and (2). Specific examples of $R^8$ in formulas (10) and (11) are the same as that above-described as examples of $R^3$ and $R^4$ in formulas (1) and (2). However, preferable examples of $R^3$, $R^4$ and $R^8$ in formulas (10) and (11) include a hydrogen atom.

It is preferable that $R^1$ is a hydrogen atom, $R^2$ is a saturated hydrocarbon radical of 1 to 5 carbon atoms, and $R^3$ and $R^4$ are each independently a saturated hydrocarbon radical of 1 to 6 carbon atoms, $R^8$ is a saturated hydrocarbon radical of 1 to 5 carbon atoms or a saturated or unsaturated hydrocarbon radical of 12 or 18 in formulas (10) and (11).

$Z^-$ is an anion derived from an organic or inorganic acid. Specific examples of $Z^-$ include anions derived from an inorganic acid such as $OH^-$, $Cl^-$, $Br^-$, $F^-$, $I^-$, $CO_3^-$, $PO_3^-$, $SO_4^{2-}$; and anions derived from an organic acid such as aliphatic carboanion, aromatic carboanion, aliphatic sulphoanion, aromatic sulphoanion; and the like.

No particular limitation is placed on the ratio of α-repeating units to β-repeating units present in the molecule of the polyaspartic acid derivatives of the present invention. For example, only one type of repeating units may be present, or both types of repeating units may be present in admixture.

In the polyaspartic acid derivatives of the present invention, the proportion of the repeating units of formula (1) and/or formula (2) (hereinafter referred to as "amphoteric ion structure units") is in the range of 1 to 100 mol %. The polyaspartic acid derivatives of the present invention can contain the other repeating units than amphoteric ion structure units without spoiling the effect of the present invention. As the other repeating units than amphoteric ion structure units, at least one repeating unit selected from the group consisting of repeating units represented by the formulas (3) and (11).

In particular, when it contains at least one repeating unit selected from the group consisting of repeating units represented by the formulas (3) and (4) (hereinafter referred to as "hydrophobic structure units"), the effect of set-keeping capacity in a highly humid state is further remarkable. It is preferable that the proportion of the other units such as units of formulas (6) to (11) is about 50 mol % or less for substancially preventing to spoil the effect of set-keeping capacity while it depends the kinds.

In the polyaspartic acid derivatives of the present invention, the solubility in a solvent can be controlled by controlling the proportion of amphoteric ion structure units and repeating units of formulas (3) to (11). Especially, it can be controlled by controlling the proportion of hydrophobic structure units and the numbers of carbon atoms of $R^6$ and $R^7$ in formulas (3) and (4). In general, resins soluble in water, water/ethanol or ethanol are preferred in view of hairdressing properties and practise in uses such as hair-treating agents.

In the polyaspartic acid derivatives of the present invention, the following embodiments [a] to [g] are preferred because they are soluble in water or water/ethanol while keeping the good hairdressing properties.

[a] Hydrophobic structure units of 1 to 5 carbon atoms are in 15 to 90 mole %, amphoteric ion structure units are in 10 to 85 mole %, and the other units are selected from units of formulas (5) to (11) if there are contained in.

[b] Hydrophobic structure units of 6 to 10 carbon atoms are in 5 to 80 mole %, amphoteric ion structure units are in 20 to 95 mole %, and the other units are selected from units of formulas (5) to (11) if there are contained in.

[c] Hydrophobic structure units of 11 to 18 carbon atoms are in 1 to 35 mole %, amphoteric ion structure units are in 65 to 99 mole %, and the other units are selected from units of formulas (5) to (11) if there are contained in.

[d] Hydrophobic structure units of 1 to 5 carbon atoms are in 15 to 90 mole %, hydrophobic structure units of 6 to 10 carbon atoms are in 5 to 80 mole %, amphoteric ion structure units are in 10 to 80 mole %, and the other units are selected from units of formulas (5) to (11) if there are contained in.

[e] Hydrophobic structure units of 1 to 5 carbon atoms are in 15 to 90 mole %, hydrophobic structure units of 11 to 18 carbon atoms are in 1 to 35 mole %, amphoteric ion structure units are in 10 to 84 mole %, and the other units are selected from units of formulas (5) to (11) if there are contained in.

[f] Hydrophobic structure units of 6 to 10 carbon atoms are in 5 to 80 mole %, amphoteric ion structure units are in 20 to 94 mole %, and the other units are selected from units of formulas (5) to (11) if there are contained in.

[g] Hydrophobic structure units of 1 to 5 carbon atoms are in 15 to 90 mole %, hydrophobic structure units of 6 to 10 carbon atoms are in 5 to 80 mole %, hydrophobic structure units of 11 to 18 carbon atoms are in 1 to 35 mole %, amphoteric ion structure units are in 10 to 79 mole %, and the other units are selected from units of formulas (5) to (11) if there are contained in.

In the polyaspartic acid derivatives of the present invention, the following embodiments [h] to [n] are preferred because they are soluble in ethanol while keeping the good hairdressing properties.

[h] Hydrophobic structure units of 1 to 5 carbon atoms are in 50 to 95 mole %, amphoteric ion structure units are in 5 to 50 mole %, and the other units are selected from units of formulas (5) to (11) if there are contained in.

[i] Hydrophobic structure units of 6 to 10 carbon atoms are in 20 to 99 mole %, amphoteric ion structure units are in 1 to 80 mole %, and the other units are selected from units of formulas (5) to (11) if there are contained in.

[j] Hydrophobic structure units of 11 to 18 carbon atoms are in 10 to 40 mole %, amphoteric ion structure units are in 60 to 90 mole %, and the other units are selected from units of formulas (5) to (11) if there are contained in.

[k] Hydrophobic structure units of 1 to 5 carbon atoms are in 50 to 95 mole %, hydrophobic structure units of 6 to 10 carbon atoms are in 20 to 99 mole %, amphoteric ion structure units are in 1 to 30 mole %, and the other units are selected from units of formulas (5) to (11) if there are contained in.

[l] Hydrophobic structure units of 1 to 5 carbon atoms are in 50 to 95 mole %, hydrophobic structure units of 11 to 18 carbon atoms are in 10 to 40 mole %, amphoteric ion structure units are in 5 to 40 mole %, and the other units are selected from units of formulas (5) to (11) if there are contained in.

[m] Hydrophobic structure units of 6 to 10 carbon atoms are in 20 to 99 mole %, hydrophobic structure units of 11 to 18 carbon atoms are in 10 to 40 mole %, amphoteric ion structure units are in 1 to 70 mole %, and the other units are selected from units of formulas (5) to (11) if there are contained in.

[n] Hydrophobic structure units of 1 to 5 carbon atoms are in 50 to 95 mole %, hydrophobic structure units of 6 to 10 carbon atoms are in 20 to 99 mole %, hydrophobic structure units of 11 to 18 carbon atoms are in 10 to 40 mole %, amphoteric ion structure units are in 1 to 20 mole %, and the other units are selected from units of formulas (5) to (11) if there are contained in.

No particular limitation is placed on the mode of arrangement of the repeating units constituting the polyaspartic acid derivatives of the present invention. In the case of copolymers, they may be random copolymers, alternating copolymers, block copolymers or graft copolymers. The polymers may be linear, macrocyclic, branched, stellate or three-dimensional network structured. The "polyaspartic acids" may include a polymer obtained by peptide condensation of amino acid.

In the polyaspartic acid derivatives of the present invention, no particular limitation is placed on the average molecular weight thereof if a desired effects can substantially appear. However, when it is expressed in terms of weight-average molecular weight as measured by gel permeation chromatography (hereinafter referred to as GPC), for example, in a chloroform solvent system, the polyaspartic acid derivatives of the present invention may generally have a weight-average molecular weight of 5,000 to 5,00,000, preferably 7,000 to 4,000,000, more preferably 8,000 to 3,500,000 and most preferably 10,000 to 2,000,000. By choosing this weight-average molecular weight so as to be equal to or greater than a specific value (generally 5,000, preferably 7,000, more preferably 8,000 and most preferably 10,000), the polyaspartic acid derivatives produce more excellent effects, for example, in that an improvement in the hair-setting power of the resulting hair-treating composition, an improvement in the moisture retention capacity and feel of the resulting humectant composition, and an improvement in the dispersion capacity and conditioning effect of the resulting cleansing composition can be achieved. On the other hand, by choosing this weight-average molecular weight so as to be equal to or less than a specific value (generally 5,000,000, preferably 4,000,000, more preferably 3,500,000 and most preferably 2,000,000), the polyaspartic acid derivatives produce more excellent effects, for example, in that an improvement in solvent solubility and an improvement in handling due to a reduction in solution viscosity can be achieved.

The average number of all repeating units in the polyaspartic acid derivatives of the present invention is, preferably, in the range of 10 to 5,000. The average number depends on the starting polysuccinimide.

[Processes for the Preparation of polymer (polyaspartic acid derivatives)]

No particular limitation is placed on the method of the preparation of the above-described polyaspartic acid derivatives. However, the above-described polyaspartic acid derivatives can be readily and satisfactorily prepared by employing processes in accordance with the present invention, i.e., a process in which polysuccimide is reacted with amines in the presence or absence of a basic catalyst and the resulting product is made amphoteric by reaction with a halogenated organic acid, or a process in which polysuccimide is reacted with an amine having an amphoteric ion in the presence or absence of a basic catalyst. The processes of the present invention will be more specifically described hereinbelow.

The polysuccinimide used as the starting material in the processes for the preparation of polyaspartic acid derivatives is represented by formula (12)

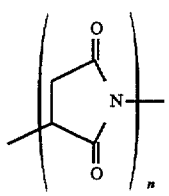

(12)

This polysuccinimide can be prepared according to any of various well-known processes. For example, a process for the condensation of aspartic acid by heating it at 200° C. for 2–3 hours is disclosed in J. Amer. Chem. Soc., 80, 3361 (1958), and a process for the preparation of a high-molecular-weight polysuccinimide by using 85% phosphoric acid as the catalyst and carrying out the reaction in a thin film by means of a rotary evaporator is disclosed in Japanese Patent Publication No. 20638/'73. Moreover, U.S. Pat. No. 5,057,597 discloses an industrial process for the preparation of polysuccinimide in which polysuccinimide is further condensed in a fluidized bed by the application of heat. When polysuccinimide having a higher molecular weight is needed, polysuccinimide prepared by any of the above-described processes may further be treated with a condensing agent such as dicyclohexylcarbodiimide.

No particular limitation is placed on the molecular weight of polysuccinimide if a desired effects substantially appear. The average number (n) of the repeating units of the polysuccinimide is preferably in the range of 10 to 5,000. In terms of molecular weight, the weight-average molecular weight as measured by GPC may generally be in the range of 5,000 to 500,000, preferably 7,000 to 400,000, more preferably 9,000 to 300,000 and most preferably 10,000 to 200,000. By choosing this weight-average molecular weight so as to be equal to or greater than a specific value (generally 5,000, preferably 7,000, more preferably 9,000 and most preferably 10,000), the polysuccinimide causes an increase in the molecular weight of the resulting polyaspartic acid derivative and hence produces more excellent effect in the above-described various respects. On the other hand, by choosing this weight-average molecular weight so as to be equal to or less than a specific value (generally 500,000, preferably 400,000, more preferably 300,000 and most preferably 200,000), the polysuccinimide produces more excellent effect, for example, in that an improvement in solubility in the reaction solvent and a reduction in reaction viscosity can be achieved.

As the organic solvent used in the processes of the present invention, there may be used any organic solvent that can dissolve at least one of polysuccinimide and amines or salts thereof. However, in order to accelerate the reaction, it is preferable to use an organic solvent which can dissolve both of polysuccinimide and amines or salts thereof. Specific examples of the organic solvent include aprotic organic solvents such as N,N-dimethylformamide (DMF), N,N-dimethylacetamide (DMAc), N,N'-dimethylimidazolidinone (DMI), N-methylpyrrolidone (NMP), N-imidazolidine, dimethyl sulfoxide (DMSO) and sulfolane; and mixed solvents consisting essentially of these solvents and also containing other solvents. Among them, solvents consisting essentially of DMF and DMSO are preferred.

It is preferable that the raw materials (i.e., polysuccinimide and amines or salts thereof) and reaction solvent used have previously been freed of water, for example, by drying. Since the raw materials used are all hygroscopic, it frequently happens that they usually contain several percent of water. If a large amount of water is present, side reaction will occur during the reaction, making it impossible to obtain a polyaspartic acid derivative having the desired structure. The amount of water contained in the reaction system composed of the raw materials and the solvent should preferably be less than 18 parts by weight, more preferably less than 10 parts by weight, still more preferably less than 5 parts by weight and most preferably less than 1 parts by weight, per 100 parts by weight of the polysuccinimide charged.

In one process of the present invention, the polysuccinimide of formula (12) is reacted with at least one compound (hereinafter referred to as the "diamine") selected from the group consisting amines of formula (13)

(13)

where $R^1$ is a hydrogen atom or a lower hydrocarbon radical of 1 to 6 carbon atoms, $R^2$ is a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, and salts thereof.

Specific examples of $R^1$ in formula (13) are the same as that above-described as examples of $R^1$ in formulas (1) and (2), except that, as $R^1$ in formula (13), hydrogen atom, methyl, ethyl and propyl are more preferred, and hydrogen atom is most preferred. Specific examples of $R^2$ in formula (13) are the same as that above-described as examples of $R^2$ in formulas (1) and (2). Specific examples of $R^3$ and $R^4$ in formula (13) are the same as that above-described as examples (and six members rings) of $R^3$ and $R^4$ in formulas (1) and (2), except that preferable examples of $R^3$ and $R^4$ in formula (13) include hydrogen atom.

Specific examples of the diamine include N,N-dimethyl-1,2-ethylenediamine, N,N-bis(2-hydroxyethyl)ethylenediamine, N,N-diethyl-1,2-ethanediamine, N,N-dipropyl-1,2-ethanediamine, N,N-diisopropyl-1,2-ethanediamine, N,N-t-butylethylenediamine, N-ethyl-N-β-hydroxyethylethylenediamine, N,N-diisobutyl-1,2-ethanediamine, N,N-dibutyl-1,2-ethanediamine, N-ethyl-N-n-butylethylenediamine, 2-(methyl-N-butylamino)ethylamine, N2,N2-dimethyl-1,2-propanediamine, N2,N2-diethyl-1,2-propanediamine, N1,N1-di-n-propyl-1,2-propanediamine, N1,N1-dimethyl-1,2-propanediamine, N,N-dimethyl-1,3-propanediamine, N,N-diethyl-1,3-propanediamine, N,N-dibutyl-1,3-propanediamine, N,N,2,2-tetramethyl-1,3-propanediamine, diethanolaminopropylamine, 1-amino-3-diethylamino-2-propanol, 2-amino-2-methyl-3-hexanol, N,N-dimethyl-1,4-butanediamine, N,N-diethyl-1,4-butanediamine, N,N-diisopropyl-1,4-butanediamine, N1,N1-diethyl-1,4-pentanediamine, N,N-dimethyl-1,5-pentanediamine, N,N-diethyl-1,5-pentanediamine, N,N-diisopropyl-1,5-pentanediamine, N,N-diisobutyl-1,5-pentanediamine, N,N-dibutyl-1,6-hexanediamine, N,N-dimethyl-1,6-hexanediamine, N,N-dimethyl-1,7-heptanediamine, N,N-diethyl-1,7-heptanediamine, N1,N9-dimethyl-10-hydroxyoctadecanediamine, N1,N9-diethyl-10-hydroxyoctadecanediamine, N1,N9-diethanol-10-hydroxyoctadecanediamine and N,N-diethyl-2-butene-1,4-diamine. In addition, they also include amines having an oxaalkylene group (e.g., dimethylaminoethoxypropylamine) and salts thereof; and amines having an azaalkylene group [e.g., 3-amino-3'-dimethylamino-N-methyldipropylamine and N-(dimethylaminoethyl)ethylenediamine] and salts thereof.

In the other process of the present invention, the starting polysuccinimide is reacted with at least one compound (hereinafter referred to as the "amphoteric amine") selected from the group consisting of amines containing amphoteric ion of formula (15)

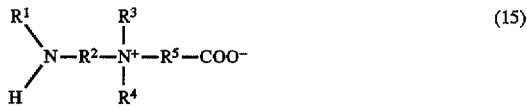
(15)

where $R^1$ is a hydrogen atom or a lower hydrocarbon radical of 1 to 6 carbon atoms, $R^2$ and $R^5$ are each independently a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, and salts thereof.

Specific examples of $R^1$ in formula (15) are the same as that above-described as examples of $R^1$ in formulas (1) and (2), except that, as $R^1$ in formula (13), hydrogen atom, methyl, ethyl and propyl are more preferred, and hydrogen atom is most preferred. Specific examples of $R^2$ and $R^5$ in formula (15) are the same as that above-described as examples of $R^2$ and $R^5$ in formulas (1) and (2). Specific examples of $R^3$ and $R^4$ in formula (15) are the same as that above-described as examples (and six members rings) of $R^3$ and $R^4$ in formulas (1) and (2), except that, preferable examples of $R^3$ and $R^4$ in formula (13) include hydrogen atom.

No particular limitation is placed on the types of the diamine and the amphoteric amine, provided that the desired reaction rate can be substantially secured. They may be either in free form or in the form of a mineral acid salt such as hydrochloride or sulfate. However, it is generally preferable from the viewpoint of reaction rate that they are in free form.

The amount of diamine and/or amphoteric amine used may be suitably determined so as to be in the range of 0.1 to 10 times the number of moles of the imide ring of the polysuccinimide, depending on the proportion of amphoteric ions in the desired polyaspartic acid derivative. Specifically, as the ratio of the amine or salt thereof to the polysuccinimide is increased, the molar proportion of amphoteric ions in the resulting polyaspartic acid derivative becomes higher. Moreover, as the diamine and/or amphoteric amine used for the reaction become bulkier, their reaction with the polysuccinimide tends to slow down. Consequently, when a bulky diamine and/or a bulky amphoteric amine are to be reacted, the reaction can be accelerated by using them in an amount larger than the desired proportion of amphoteric ions. However, if the amount of diamine and/or amphoteric amine reacted is excessively large relative to the imide ring of the polysuccinimide, the basicity of the reaction system will become so high that the main chain of the polysuccinimide may be broken. Generally speaking, therefore, the amount of diamine and/or amphoteric amine used for the reaction is preferably in the range of 0.01 to 10 times, more preferably 0.07 to 2 times, the number of moles of the imide ring of the polysuccinimide.

No particular limitation is placed on the concentrations of the polysuccinimide and the diamine and/or amphoteric amine in the reaction system, provided that the progress of the reaction can be substantially maintained. The concentration of the reaction system is determined on the basis of the concentration of the polysuccinimide. Generally, the concentration of the polysuccinimide is chosen within the range of 1 to 50% by weight. Although the concentration of the starting polysuccinimide may be chosen within the range of 1 to 50% by weight so as to be the optimum for the diamine and/or amphoteric amine used, it is generally preferable to use a concentration of 5 to 30% by weight.

In the processes of the present invention, the reaction of the polysuccinimide with the diamine and/or amphoteric amine proceeds without using any catalyst. However, a basic catalyst may be used as required. Specific examples of the basic catalyst include aliphatic tertiary amines such as trimethylamine, triethylamine, tripropylamine, tributylamine, diisopropylethylamine (DIEA), triethanolamine and triethylenediamine (DABCO); alicyclic tertiary amines such as N-methylmorpholine; aromatic tertiary amines such as dimethylaniline and diethylaniline; and tetramethylguanidine. These basic catalysts may be used alone or in combination. No particular limitation is placed on the amount of basic catalyst used, provided that the reaction can be substantially accelerated. The amount of basic catalysts used is generally in the range of 0 to 2 times the number of moles of the diamine and/or amphoteric amine. When the diamine and/or amphoteric amine are mineral acid salts, a base is further added in an amount required to neutralize the mineral acid.

The reaction temperature may be suitably determined according to the diamine and/or amphoteric amine used. Generally speaking, as the diamine and/or amphoteric amine becomes bulkier, they tend to be less soluble in the solvent owing to a reduction in freezing point. Consequently, the reaction with a bulky diamine and/or a bulky amphoteric amine can be accelerated by raising the reaction temperature. However, unduly high reaction temperatures are undesirable because the polysuccinimide may undergo side reactions with impurities present in the reaction system and the diamine and/or amphoteric amine may undergo changes in nature. Unduly low reaction temperatures are also undesirable because the progress of the reaction becomes slow. Generally speaking, the reaction temperature is preferably in the range of 0° to 150° C., more preferably 0° to 100° C. and still more preferably 20° to 80° C.

In the process of the present invention wherein the starting polysuccinimide is reacted with the diamine of formula (13), the amine groups dangling as pendant groups are converted into quaternary ammonium groups and thereby made amphoteric. Specifically, the resulting product is further reacted with a halogenated fatty acid salt (hereinafter referred to as the "fatty acid salt") of formula (14)

$$L—R^5—COOM \quad (14)$$

where L is a halogen atom, $R^5$ is a saturated or unsaturated hydrocarbon radical of 1 to 24 carbon atoms, and M is a hydrogen atom, an alkali metal atom or an alkaline earth metal atom.

It is preferable that $R^5$ is a saturated or unsaturated hydrocarbon radical of 1 to 18 carbon atoms. Specific examples of $R^5$ in formula (14) are the same as that above-described as examples of $R^5$ in formulas (1) and (2).

Specific examples of the fatty acid salt include potassium monochloroacetate, sodium monochloroacetate, potassium monobromoacetate, sodium monobromoacetate, sodium monofluoroacetate, potassium monofluoroacetate, sodium monoiodoacetate, potassium monoiodoacetate, potassium monochloropropionate, sodium monochloropropionate, potassium monobromopropionate, sodium monobromopropionate, sodium monofluoropropionate, potassium monofluoropropionate, sodium monoiodopropionate and potassium monoiodopropionate. Among them, potassium monochloroacetate, sodium monochloroacetate, potassium monochloropropionate, sodium monochloropropionate and the like are preferred.

As the fatty acid salt, the above-enumerated fatty acid salts may be directly used. Alternatively, there may also be used products obtained, for example, by neutralizing a monochloroacetate with one or more compounds selected from ammonia, lithium hydroxide, sodium hydroxide, potassium hydroxide, mono-, di- or triethanolamine, mono-, di- or tripropanolamine, aminomethylpropanol, aminoethylpropanol, aminomethylpropanediol, benzylamine, morpholine, laurylamine and cycloalkylamine. In view of the solubility of the halogenated fatty acid salt used for amphoterization and the ease of removal of the resulting salt, potassium salts are preferred and potassium monochloroacetate is more preferred.

Furthermore, it is preferable to make the resulting product cationic by reaction with at least one of halogenated ester of formula (17), and thereafter it amphoterized by hydrolysis. The method for cationization are disclosed latter.

$$L—R^8—COOR^9 \quad (17)$$

where $R^8$ and $R^9$ are each independently a saturated or unsaturated hydrocarbon radical of 1 to 24 carbon atoms.

Specific examples of halogenated ester (halogenated fattyester) of formula (17) include methyl monochloroacetate, ethyl monochloroacetate, propyl monochloroacetate, dodecyl monochloroacetate, octadecyl monochloroacetate, octadecenyl monochloroacetate, methyl monobromoacetate, ethyl monobromoacetate, methyl monofluoroacetate, ethyl monofluoroacetate, methyl monoiodoacetate, ethyl monoiodoacetate, methyl monochloropropionate, ethyl monochloropropionate, methyl monofluoropropionate, ethyl monofluoropropionate, methyl monoiodopropionate, ethyl monoiodopropionate. Among them, methyl monochloroacetate, ethyl monochloroacetate, methyl monochloropropionate and ethyl monochloropropionate are preferred, and methyl monochloroacetate and ethyl monochloroacetate are more preferred.

The solvent used for this amphoterization may be one which can substantially dissolve at least one of the reaction product of polysuccinimide with the diamine (hereinafter referred to as the diamine ring-opened product) and the aforesaid fatty acid salt. However, in consideration of the progress of the reaction, it is preferable to use a solvent which can substantially dissolve both the diamine ring-opened product and the fatty acid salt. Specific examples of the solvent include distilled water; aprotic organic solvents such as DMF, DMAc, DMI, DMSO and sulfolane; alcoholic organic solvents such as methanol, ethanol, n-propanol and isopropyl alcohol; and halogenated organic solvents such as chloromethane, dichloromethane, trichloromethane, tetrachloromethane and o-dichlorobenzene. These solvents may be used alone or in combination. Among them, methanol, ethanol, chloroform and methanol/chloroform solvent mixtures are preferred, for example, because they can dissolve the diamine ring-opened product and the fatty acid salt with substantial ease.

No particular limitation is placed on the amount of fatty acid salt used for amphoterization, provided that it can dissolve in the solvent and/or it can accelerate the reaction significantly. It may be suitably determined according to the molar amount of amphoteric ions present in the desired polyaspartic acid derivative and/or the molar amount of diamine used for synthesis of the diamine ring-opened product. Since the fatty acid salt used for amphoterization in unnecessarily large amounts may make it difficult to remove the resulting salt, the fatty acid salt is generally used in an amount equal to about 0.1 to 10 times, preferably 0.1 to 2 times, the number of moles the diamine used for synthesis of the diamine derivative.

As the concentration of the reaction system used in the amphoterization reaction, the concentration of the diamine ring-opened product is generally in the range of 1 to 50% by weight and preferably 5 to 30% by weight.

In the amphoterization reaction, the reaction temperature is chosen within the range of 0° to 150° C., and it may be suitably determined according to the solvent used. However, if the reaction temperature is unduly high, the diamine ring-opened product may undergo side reactions with impurities present in the reaction system and/or changes in nature. Generally speaking, therefore, the reaction temperature is preferably in the range of about 0° to 100° C. and more preferably 20° to 80° C.

No particular limitation is placed on the method for isolating the polyaspartic acid derivative from the reaction mixture after completion of the reaction, provided that the reaction product can be substantially isolated at a desired purity. Generally, there may be employed any of various well-known and commonly used isolation techniques such as concentration, recrystallization and reprecipitation. One exemplary procedure is such that, after completion of the reaction, an excess of a solvent (e.g., methyl alcohol, ethyl alcohol, isopropyl alcohol, acetone or hexane) is added to the reaction mixture having the reaction product dissolved therein at an appropriate temperature, and the resulting precipitate of the reaction product is isolated by decantation, filtration or suction filtration, thoroughly washed with a solvent incapable of dissolving the precipitate, and then dried. Another exemplary procedure is such that, after completion of the reaction, the reaction mixture having the reaction product dissolved therein is added to an excess of the aforesaid solvent at an appropriate temperature, and the resulting precipitate of the reaction product is isolated, washed and dried in the same manner as described above.

The solvent used in excess preferably comprises a solvent with which the excess or unreacted amine can be easily washed off. Specific examples thereof include acetone, methanol, ethanol, isopropanol, ethyl acetate, hexane, diethyl ether, tetrahydrofuran, chloroform, toluene and solvent mixtures thereof. Among them, acetone, methanol, ethanol, hexane, chloroform and an acetone/hexane solvent mixture are preferred.

As to the order of isolation, the reaction product may be isolated in the above-described manner after the polysuccinimide is reacted with the diamine and/or amphoteric amine and, when the diamine is used, the resulting product is made amphoteric by reaction with the fatty acid salt. Alternatively, the reaction product may be once isolated in the above-described manner after the polysuccinimide is reacted with the diamine and/or amphoteric amine. And, when the diamine is used, this reaction product is made amphoteric by reaction with the fatty acid salt, and the resulting product is isolated again in the above-described manner. However, the polysuccinimide and unreacted diamine, though in slight amounts, remain in the reaction system and a salt is formed during amphoterization. In view of these facts, it is generally preferable from the viewpoint of the purity of the resulting polyaspartic acid derivative that, when the diamine is used, the reaction product is once isolated after the polysuccinimide is reacted with the diamine, this reaction product is made amphoteric, and the resulting product is isolated again.

When a suitable amphoterization solvent is selected in the processes of the present invention, the resulting inorganic salt by-product (i.e., a sodium halide or a potassium halide) separates out as a precipitate (which does not always settle) in the reaction mixture having undergone the amphoterization reaction, and is then removed. No particular limitation is placed on the method for removing this inorganic salt by-product, provided that the inorganic salt by-product can be substantially removed to a desired purity. Generally, there may be employed any of various well-known removal techniques for use in solid-liquid separation, such as centrifugation and filtration. One exemplary procedure is such that, after completion of the reaction, the precipitated inorganic salt by-product is removed by centrifugation, decantation, filtration or suction filtration at an appropriate temperature.

After the inorganic salt by-product has been removed in this manner, the reaction mixture may still contain a small amount (about 0.1 to 1% by weight) of inorganic salt by-product. In this case, the inorganic salt by-product can be fully removed by treating the filtered reaction mixture with an ion-exchange resin, for example, in a batch or flow process. Thus, its ash content can be reduced to 0.1% by weight or less.

After the reaction mixture has been freed of the inorganic salt by-product or treated with an ion-exchange resin in the above-described manner, the resulting polyaspartic acid derivative solution is preferably adjusted to a concentration of 10 to 60% by weight and may be directly used for various purposes in the state dissolved in the solvent. Alternatively, after the reaction mixture has been freed of the inorganic salt by-product or treated with an ion-exchange resin, the solvent may be removed to recover the polyaspartic acid derivative in solid form. Thereafter, this product can be used by diluting it with a solvent or the like according to various purposes.

In the process of the present invention, it is preferred to use at least one compound selected from the group consisting of amines of formula (16)

where $R^6$ and $R^7$ are each independently a hydrogen atom, or a saturated or unsaturated hydrocarbon radical of 1 to 24 carbon atoms in which $R^6$ and $R^7$ may bonded together to form a six members ring containing nitrogen atom, and salts thereof (hereinafter referred to as the "hydrophobic amine") for the reaction.

The hydrophobic amine more excellent effects in that an improvement in hair-setting power under high-temperature and high-humidity conditions can be achieved. It is preferable that $R^6$ and $R^7$ are each independently a saturated or unsaturated hydrocarbon radical of 4 to 18 carbon atoms in formulas (3) and (4).

Specific examples of $R^6$ and $R^7$ in formula (16) are the same as that above-described as examples (and six members rings) of $R^6$ and $R^7$ in formulas (3) and (4).

Specific examples of the hydrophobic amine include alkylamines such as methylamine, ethylamine, propylamine, butylamine, pentylamine, hexylamine, heptylamine, octylamine, nonylamine, decylamine, dodecylamine, tetradecylamine, hexadecylamine, octadecylamine, octadecenylamine, and eicosyldecylamine; hydroxyalkylamines such as hydroxymethylamine, 2-aminoethanol, hydroxypropylamine, hydroxybutylamine, 2,2- aminoethoxyethanol, 3-(2-ethylhexyloxy)propylamine, N-aminoethylethanolamine, hydroxypentylamine, hydroxyhexylamine, hydroxyoctylamine, hydroxydecylamine, hydroxydodecylamine, hydroxytetradecylamine, hydroxyhexadecylamine, hydroxyoctadecylamine and hydroxyeicosylamine; alkenylamines such as hydroxyalkenylamines, hexenylamine, octynylamine, decenylamine, dodecenylamine, tetradecenylamine, hexadecenylamine, octadecenylamine and eicosenylamine; and cycloalkylamines such as cyclobutylamine, cyclopentylamine, cyclohexylamine, cycloheptylamine, cyclohexylmethylamine, cyclohexylethylamine and cyclohexylbutylamine. In addition, they also include azaalkylamines, azaalkenylamines; thioalkylamines, thioalkenylamines; oxaalkylamines and oxaalkenylamines; amino alkylic acids such as amino caproic acid and 11-aminoundecanoic acid. Furthermore, they also include bioamines such as cystamin, cysteamine, spermidine, spermine, norepinephrine; amino acids such as azaserine, glycine, asparagine, 4-aminobutylic acid, β-alanine, arginine, ornithine, glutamine, creatine, sarcosine, cystine, cytosine, taurine, hydroxylysine, lysine and rationine, and amino acid esters thereof.

Among them, methylamine, ethylamine, propylamine, butylamine, pentylamine, hexylamine, octylamine, dodecylamine, tetradecylamine, hexadecylamine, octadecylamine, octadecenylamine, 2-aminoethanol, hydroxypropylamine, hydroxybutylamine, 2,2-aminoethoxyethanol, 3-(2-ethylhexyloxy)propylamine, N-aminoethylethanolamine, hydroxyhexylamine, hydroxyoctylamine, hydroxydodecylamine, cyclobutylamine, cyclopentylamine, cyclohexylamine and cycloheptylamine; bioamines such as cystamin and cysteamine; and amino acids such as glycine, asparagine, 4-aminobutylic acid, β-alanine, arginine, ornithine, glutamine, cystine, cytosine, taurine, hydroxylysine and lysine, and amino acid esters thereof are preferred.

Furthermore, propylamine, butylamine, hexylamine, octylamine, dodecylamine, octadecylamine, octadecenylamine, 2-aminoethanol, hydroxypropylamine, hydroxybutylamine, 2,2-aminoethoxyethanol, 3-(2-ethylhexyloxy)propylamine and N-aminoethylethanolamine; bioamines such as cystamin and cysteamine; and amino acids such as glycine, asparagine, 4-aminobutylic acid, β-alanine, arginine, ornithine, glutamine, cystine, taurine, hydroxylysine and lysine, and amino acid esters thereof are preferred.

The hydrophobic amine may be either in free form or in the form of a mineral acid salt such as hydrochloride or sulfate. However, it is generally preferable from the viewpoint of reaction rate that the hydrophobic amine is in free form.

The amount of hydrophobic amine used may be suitably determined so as to be in the range of 0.1 to 10 times the number of moles of the imide ring of the polysuccinimide, depending on the proportion of the hydrophobic amine in the desired polyaspartic acid derivative. Specifically, as the ratio of the hydrophobic amine to the polysuccinimide is increased, the molar proportion of the hydrophobic amine in the resulting polyaspartic acid derivative becomes higher. Moreover, as the hydrophobic amine used for the reaction become bulkier, its reaction with the polysuccinimide tends to slow down. Consequently, when a bulky hydrophobic amine is to be reacted, the reaction can be accelerated by using it in an amount larger than the desired molar proportion of the hydrophobic amine or a salt thereof. However, if the amount of hydrophobic amine reacted is excessively large relative to the imide ring of the polysuccinimide, the basicity of the reaction system will become so high that the main chain of the polysuccinimide may be broken. Generally speaking, therefore, the amount of hydrophobic amine used for the reaction is preferably in the range of 0.1 to 5 times, more preferably 0.1 to 2 times, the number of moles of the imide ring of the starting polysuccinimide.

As to the concentration of the reaction system for the reaction of the polysuccinimide with the hydrophobic amine, the type and amount of the basic catalyst, and the reaction temperature, the same description as previously given for the diamine and/or amphoteric amine also applies well in this case.

The reaction of the polysuccinimide with the hydrophobic amine, and the reaction of the polysuccinimide with the diamine may be carried out either in any desired order or at the same time. However, when the reaction rate is taken into consideration, the reaction tends to slow down as the diamine and the hydrophobic amine become sterically bulkier (e.g., they increase in the number of carbon atoms or they comprise secondary amines rather than primary amines). Generally speaking, it is preferable to compare the diamine with the hydrophobic amine and react the one having more carbon atoms or being sterically bulkier preferentially, because this speeds up the reaction with the polysuccinimide.

After reaction of polysuccinimide with diamines, halogenated alkyl or halogenated ester of formula (17) (hereinafter referred to as the "esters") can be used for cationization by quadrivalent of amine. Before reaction of polysuccinimide with diamines, the diamines may be cationized by the esters, then it can be used for the reaction with polysuccinimide.

As the esters, the above-enumerated fatty acid esters may be directly used. Alternatively, there may also be used products obtained, for example, by esterization of fatty acids with catalysts such as sulfuric acid, hydrochloric acid, thionyl chloride and trifluoroacetate. For the reaction, the other halogenated alkyls than that of formula (17) can be used.

The solvent used for this cationization may be one which can substantially dissolve at least one of the reaction product of polysuccinimide with the diamine (diamine ring-opened product) and the aforesaid esters. However, in consideration of the progress of the reaction, it is preferable to use a solvent which can substantially dissolve both the diamine ring-opened product and the fatty acid ester. Specific examples of the solvent include distilled water; aprotic organic solvents such as DMF, DMAc, DMI, DMSO and sulfolane; alcoholic organic solvents such as methanol, ethanol, n-propanol and isopropyl alcohol; and halogenated organic solvents such as chloromethane, dichloromethane, trichloromethane, tetrachloromethane and o-dichlorobenzene. These solvents may be used alone or in combination. Among them, methanol, ethanol, chloroform and methanol/chloroform solvent mixtures are preferred, for example, because they can dissolve the diamine ring-opened product and the fatty acid salt with substantial ease.

The halogenated esters and halogenated alkyl used for cationization is generally used in an amount equal to about 0.1 to 10 times, preferably 0.1 to 2 times, the number of moles the diamine used for synthesis of the derivative. As the concentration of the reaction system used in the cationization reaction, the concentration of the diamine ring-opened product is generally in the range of 1 to 50% by weight and preferably 5 to 30% by weight.

In the cationization reaction, the reaction temperature is chosen within the range of 0° to 150° C., and it may be suitably determined according to the solvent used. However, if the reaction temperature is unduly high, the diamine ring-opened product may undergo side reactions with impurities present in the reaction system and/or changes in nature. Generally speaking, therefore, the reaction temperature is preferably in the range of about 0° to 100° C. and more preferably 20° to 80° C.

In the processes of the present invention, when the diamine, amphoteric amine and hydrophobic amine (hereinafter referred to as the "amines") are used in a total amount of less than 1 mole per mole of the imide rings of the polysuccinimide, unreacted imide rings generally remain in the polyaspartic acid derivative. In such a case, some of the imide rings of the polysuccinimide may be opened with the aid of another material having active hydrogen (hereinafter referred to as the "active hydrogen material"), before, after or during the reaction of the polysuccinimide with the amines. The active hydrogen material may be any compound that can open the imide ring, and specific examples thereof include ammonia, amines and water. These active hydrogen materials may be used alone or in combination. Specific examples of the amines include organic bases such as ethanolamine, triethylamine, triethanolamine, N-methylmorpholine, dibutylamine and diisopropylethylamine. When the imide rings of the polysuccinimide are to be opened with the aid of water, they can also be opened by alkali hydrolysis using an aqueous solution of a base. No particular limitation is placed on the alkaline compound used in the alkali hydrolysis reaction, provided that the imide rings present in the molecule of the polysuccinimide can be opened to a desired degree without reducing the molecular weight of the polysuccinimide significantly. Specific examples of the base used include alkali metal hydroxides such as sodium hydroxide and potassium hydroxide; and metal carbonates such as sodium carbonate and potassium carbonate. These bases may be used alone or in combination, and anation, and are preferably added in the form of an aqueous solution. The amount of active hydrogen material used may be suitably determined according to the desired degree of ring opening and the number of moles of imide rings present in the polysuccinimide.

No particular limitation is placed on the solvent used for the opening of unreacted imide rings, provided that it can substantially dissolve at least one of the polyaspartic acid derivative having unreacted imide rings and the active hydrogen material. In consideration of the progress of the reaction, it is generally preferable to use a solvent which can dissolve both of them. Specific examples of the solvent include distilled water; aprotic organic solvents such as DMI, DMSO and sulfolane; alcoholic organic solvents such as methanol, ethanol, n-propanol and isopropyl alcohol; halogenated organic solvents such as chloromethane, dichloromethane, trichloromethane, tetrachloromethane and o-dichlorobenzene; and other organic solvents such as acetone and hexane. These solvents may be used alone or in combination. Among them, distilled water, acetone, hexane, chloroform, DMI, DMSO, sulfolane and mixtures thereof are preferred because they can dissolve both the polyaspartic acid derivative and the active hydrogen material with substantial ease.

No particular limitation is placed on the concentration of the active hydrogen material, provided that the imide rings of the polysuccinimide can be opened to a desired degree without reducing the molecular weight of the starting polysuccinimide significantly. When the imide rings of the polysuccinimide are opened, unduly low concentrations of the active hydrogen material may cause a reduction in the ring opening efficiency of the imide rings, and unduly high concentrations of the active hydrogen material may cause a reduction in molecular weight owing to a braking of the main and/or side chains of the polysuccinimide or the main and/or side chains of the reaction product of the polysuccinimide with the amines. Generally speaking, the concentration of the used is preferably in the range of 0.01 to 5 normal, more preferably 0.1 to 3 normal, based on the solvent.

The reaction temperature for ring opening reaction with the active hydrogen material may be suitably determined according to the active hydrogen material used. However, unduly high temperatures may cause a reduction in molecular weight owing to a braking of the main and/or side chains of the polysuccinimide or the main and/or side chains of the reaction product of the polysuccinimide with the amines, or may induce side reaction with impurities present in the reaction system or the side reaction of active hydrogen with the reaction product of the polysuccinimide with the amines. Accordingly, it is preferable to use a reaction temperature of 0° to 80° C.

[Applications of Polyaspartic Acid Derivatives]

The polyaspartic acid derivatives of the present invention can be suitably used in hair-treating compositions and cosmetic compositions. These compositions are characterized in that they are expected to exhibit excellent hairdressing properties (in particular, excellent set-keeping capacity in a highly humid state), good biocompatibility with the living body, and low mutagenicity during use and in that they decompose easily after being used or dumped. Moreover, they have excellent hair care effects, for example, in that they exhibit excellent moisture retention properties, impart natural smoothness to the hair, and make up for polypeptide chains lost by hair washing or the like.

Hair-treating compositions and cosmetic compositions containing such a polyaspartic acid derivative can be prepared by mixing the derivative with other desired ingredients and stirring the resulting mixture according to any well-known technique. When the polyaspartic acid derivative of the present invention is obtained in the form of a solution, it may be used for the preparation of these compositions, either as such, or after removal of the solvent, or after isolation of the polyaspartic acid derivative. When the solution is used as such, it is preferable that the solvent comprises ethanol or an ethanol-containing solvent mixture. These polyaspartic acid derivatives may be used alone or in admixture of two or more.

The hair-treating compositions comprehend so-called hair cosmetics and hairdressings, and specific examples thereof include milky lotions, hair mousses, hair gels, hair sprays, hair tonics, hair creams, hair oils, split hair coatings, brushing aids, treatment foams, blow styling agents, styling foams, styling lotions, styling gels, hair liquids, pomades, stick pomades, shampoos, dandruff-removing shampoos, rinse/conditioners, hair treatments, temporary hair dyes, semipermanent hair dyes, permanent hair dyes, hair bleaches, permanent wave agents and hair tonics. Specific examples of the cosmetics include milky lotions, emulsions, creams, cleansing creams, face powders, lipsticks, toilet waters, lotions, wet tissue, manicures, pedicures, humectants, packs, mousses, shaving creams, after-shaving lotions, deodorants and smell removers.

As used herein, the terms "cosmetic", "hair cosmetic", "hairdressing", "hairdressing spray" and "hairdressing resin" comprehend, for example, types and articles described in "Textbook for the 26th Course in Cosmetic Technology for Incoming Employees" (cosponsored by the Tokyo Society of Cosmetic Industry and the Tokyo Society of Cosmetic Engineers and sponsored by the Japanese Society of Cosmetic Industry; July, 1984; Asahi Seimei Hall), pages 34 and 35, "Table—Types of Cosmetics and Range of Efficacy", as well as cosmetics and quasi drugs described in the same textbook, page 64, "Classification of Hair Cosmetics". By showing the cited reference and the range of citation clearly, all the matters given therein are intended to form part of the disclosures of the specification of the present application. In the light of the disclosures given in the specification of the present application, those skilled in the art will be able to derive such matters directly and uniquely by reference to the shown range of citation.

In the hair-treating compositions and cosmetic compositions, no particular limitation is placed on the ingredients other than the polyaspartic acid derivative (including, for example, additives, emulsifiers and compounding ingredients), provided that the desired effects can be produced. Specific examples thereof include alcohols, neutralizers, pH regulators, perfumes, stabilizers, surfactants, emulsifiers, colorants, pigments, UV-shielding ceramic particles, thickeners, extenders, humectants, bactericides, bacteriostats, preservatives, antiseptics, high polymeric silicone compounds, anionic, cationic, nonionic and amphoteric polymeric compounds used for hair-treating agents. Their amounts added may be suitably chosen to such an extent that these ingredients do not produce undesirable effects.

Now, the present invention is more specifically described hereinbelow in connection with especially preferred applications including gel-like hairdressing compositions, humectant compositions, cleansing compositions, hairdressing spray compositions, hairdressing resin compositions and hair dye compositions.

Gel-like hairdressing compositions containing a polyaspartic acid derivative in accordance with the present invention preferably comprise the polyaspartic acid derivative, a gel-forming base material, and a solvent consisting essentially of water and/or a lower alcohol.

In conventional gel-like hairdressing compositions, a nonionic resin such as vinylpyrrolidone polymer and vinylpyrrolidone/vinyl acetate copolymer has been used as resin component. However, these gel-like hairdressing compositions form a hard film on the hair and hence tend to undergo flaking. On the other hand, the film becomes very soft under high-temperature and high-humidity conditions, so that the set of the hair tends to be disordered. In contrast, gel-like hairdressing compositions containing a polyaspartic acid derivative in accordance with the present invention have excellent properties. That is, they exhibit excellent hairdressing properties, give a good gloss to the dressed hair, have good biodegradability and high safety for the living body, impart a natural softness and a good gloss to the hair, and keep the hair in a well-set state.

In these gel-like hairdressing compositions, any of various well-known gel-forming base materials may be used. Specific examples thereof include crosslinked carboxyvinyl polymers and cellulose derivatives. Especially preferred are crosslinked carboxyvinyl polymers. Crosslinked carboxyvinyl polymers can be prepared, for example, by crosslinkingly polymerizing a monomer consisting essentially of an unsaturated carboxylic acid such as acrylic acid, methacrylic acid, itaconic acid or maleic acid, in the presence of a multifunctional compound such as ethylene glycol diacrylate, divinylbenzene, a polyallyl compounds or a polyepoxide. Crosslinked carboxyvinyl polymers of this type are commercially available, for example, under the trade names of Carbopol (a product of B. F. Goodrich Co.), HIVISWAKO (a product of Wako Pure Chemical Industries Ltd.) and Lebra Gel (a product of Guardian Chemical Co.). These crosslinked carboxyvinyl polymers may be used alone or in admixture of two or more. When a crosslinked carboxyvinyl polymer is used as the gel-forming base material, it is desirably be used in the form of a salt which has been partially or completely neutralized with a suitable alkali.

The solvent used in the gel-like hairdressing compositions comprises a solvent consisting essentially of water and/or a lower alcohol, and may contain a relatively small amount of a hydrophilic solvent such as ethylene glycol, ethyl cellosolve, dioxane or methyl acetate. Specific examples of the lower alcohol include methanol, ethanol and isopropanol. Especially preferred are water, a water/ethanol solvent mixture and a water/isopropanol solvent mixture.

The proportion of the polyaspartic acid derivative in the gel-like hairdressing compositions is preferably in the range of about 0.1 to 20% by weight, more preferably about 0.2 to 10% by weight, based on the total amount of the composition. By choosing its proportion so as to be equal to or greater than a specific value (preferably 0.1% by weight and more preferably 0.2% by weight), the resulting gel-like hairdressing composition produces more excellent effects, for example, in that excellent hairdressing performance can be achieved. On the other hand, by choosing its proportion so as to be equal to or less than a specific value (preferably 20% by weight and more preferably 10% by weight), the resulting gel-like hairdressing composition produces more excellent effects, for example, in that a feeling of stiffness and flaking can be prevented. The proportion of the gel-forming base material is preferably in the range of 0.1 to 10% by weight, more preferably 0.2 to 5% by weight, based on the total amount of the composition. The proportion of the solvent is preferably in the range of 70 to 99.8% by weight.

In addition to the above-described three ingredients, the gel-like hairdressing compositions can further contain various additives as required. Specific examples thereof include additives used for purposes of softening, lubrication, lustering and the like, such as lanolin, lanolin derivatives, glycerin, glycerin derivatives, isopropyl myristate, oleyl alcohol, dibutyl phthalate, silicone derivatives, polyethylene glycol, polyethylene glycol derivatives and pantothenyl alcohol. Moreover, they can also contain well-known additives such as surfactants, perfumes, colorants, antiseptics and pigments. Furthermore, various other polymers may also be added to such an extent as not to detract from the performance of the gel-like hairdressing compositions.

The gel-like hairdressing compositions can usually be prepared by first dissolving the gel-forming base material in the solvent to cause gelation thereof, and then adding the polyaspartic acid derivative thereto either as such or in the form of a solution in the solvent. Alternatively, they can also be prepared by dissolving the gel-forming base material and the polyaspartic acid derivative in the solvent and then subjecting the resulting solution to gelation and pH adjustment. Gelation may be accomplished according to any well-known technique. For example, when a crosslinked carboxyvinyl polymer is used as the gel-forming base material, gelation and pH adjustment can be accomplished by neutralizing the carboxyl groups partially or completely with a base. Specific examples of the base used include alkanolamines such as 2-amino-2-methyl-1-propanol, 2-amino-2-methyl-1,3-propanediol, triethanolamine and diisopropanolamine; alkali metal hydroxides such as sodium hydroxide and potassium hydroxide; basic amino acids such as arginine and lysine; and ammonia. Among them, 2-amino-2-methyl-1-propanol, diisopropanolamine, sodium hydroxide and the like are preferred.

Humectant compositions containing a polyaspartic acid derivative in accordance with the present invention desirably comprise the polyaspartic acid derivative and various common ingredients for use in cosmetics, to such an extent as not to detract from the effects of the present invention.

Conventional water-soluble humectants for use in cosmetics include polyhydric alcohols such as glycerin and polyethylene glycol; low-molecular-weight compounds such as sodium lactate and sodium pyrrolidonecarboxylate; acid mucopolysaccharides such as hyaluronic acid and chondroitin sulfate; collagen; and carrageenan. However, polyhydric alcohols are problematic in that the resulting product tends to show stickiness and give an unpleasant feeling. Moreover, low-molecular-weight compounds have the disadvantage that their moisture-retaining effect is poor. Furthermore, acid mucopolysaccharides are expensive. In contrast, humectant compositions containing a polyaspartic acid derivative in accordance with the present invention does not involve such problems. Specifically, they are less irritant to the skin and hair, have an excellent moisture-retaining effect, impart moistness to the skin and hair, and give a pleasant feeling owing to little stickiness even under high-humidity conditions. Moreover, these humectant compositions also have an anti-static effect and thereby prevent dust and the like from adhering to the skin to which the cosmetic has been applied. Moreover, when they are applied to the hair, they can keep the hair in good order and thereby prevent the hair from loosening. Accordingly, these humectant compositions are particularly useful in such applications as cosmetics and external preparations.

The products in which these humectant compositions can be incorporated include, for example, face washes such as face-washing creams, face-washing foam, toilet soaps and cleansing creams; toilet waters such as common lotions, after-shaving lotions, hand lotions, sunburn lotions and anti-sunburn lotions; creams and milky lotions such as massage creams, moisture creams, shaving creams, hand creams and anti-sunburn creams; basic cosmetics such as packs; hair cosmetics such as shampoos, rinses, hair foams, hair sprays, set lotions, hair liquids, hair dyes and hair tonics; finishing cosmetics such as face powders, foundations, lipsticks and eye shadows; and body shampoos. When these humecrant compositions are incorporated in external preparations, no particular limitation is placed on the types of the external preparations. Specific examples thereof include external preparations containing analgesics, disinfectants, antiperspirants, depilatories, antibiotics, vitamins and hormones.

The proportion of the polyaspartic acid derivative of the present invention in the humectant compositions is preferably in the range of 0.01 to 30% by weight, more preferably 0.1 to 10% by weight, based on the total amount of the composition. Moreover, other humectants may be used in combination with the polyaspartic acid derivative of the present invention.

These humectant compositions can further contain other common ingredients for use in cosmetics and the like, to such an extent as not to detract from the effects of the present invention. Specific examples thereof include surfactants such as alkyl ether sulfates, polyoxyethylene alkyl ether sulfates, α-olefinsulfonic acid salts, monoalkylammonium salts, sorbitan fatty acid esters, fatty acid alkanolamides and alkyldimethylaminoacetic acid betaine; oily materials such as higher alcohols, fatty acids, silicone derivatives, castor oil, coconut oil, squalane and beeswax; foaming agents such as fatty acid soaps; cationic polymers such as cationized cellulose derivatives and cationized guar gum; thickeners such as carboxyvinyl polymers and polyvinyl pyrrolidone; water-soluble polymers such as methylcellulose, polyvinyl alcohol and polyethylene glycol; anti-dandruff agents such as zinc pyrithione and sulfur; iridescent agents such as higher fatty acid glycol esters and metallic soaps; ultraviolet absorbers such as p-aminobenzoic acid and benzophenone derivatives; chelating agents such as EDTA and citric acid; bactericides such as p-hydroxybenzoic acid esters; antiseptics such as parabens; pH regulators such as citric acid and triethanolamine; plasticizers; pigments such as talc, kaolin, silica powder, barium sulfate and titanium dioxide; and other additives such as antioxidants, physiologically active substances, plant extracts, perfumes and colorants.

The humectant compositions can be prepared by mixing a polyaspartic acid derivative in accordance with the present invention with other desired ingredient and stirring the resulting mixture according to any well-known technique. No particular limitation is placed on the form of the humectant compositions, and they may be in the form of a liquid, cream, solid, powder or the like.

Cleansing compositions containing a polyaspartic acid derivative in accordance with the present invention desirably comprise the polyaspartic acid derivative, a surfactant and water-insoluble additives. Generally, cleansing compositions contain water-insoluble additives such as anti-dandruff agents, iridescent agents and pigments. In conventional cleansing compositions, polymeric compounds such as sodium polyacrylate, polyethylene oxide, polyvinyl pyrrolidone and cationized cellulose ether are incorporated in order to impart dispersion stability to such additives. However, even if these polymeric compounds are used, the conventional cleansing compositions are still problematic in that the stability of the dispersion is insufficient, the water-insoluble ingredients may undergo secondary agglomeration, and the choice of surfactants is limited. In contrast, cleansing compositions containing a polyaspartic acid derivative in accordance with the present invention does not involve such problems. Specifically, the more or less irritation caused by the anionic surfactant or the like constituting the chief ingredient of the cleansing compositions is unexpectedly reduced, so that they exert a milder action on the skin and the hair. Moreover, they exhibit excellent dispersion capacity for the aforesaid water-insoluble additives, and give a pleasant feeling and an excellent conditioning effect.

Specific examples of the cleansing compositions include shampoos, rinses, hair treatments, skin cleansers (e.g., body shampoos, face-washing foams, hand soaps and toilet soaps), kitchen cleaners and household cleaners.

The proportion of the polyaspartic acid derivative of the present invention in the cleansing compositions is preferably in the range of 0.01 to 20% by weight, more preferably 0.1 to 10% by weight, based on the total amount of the composition.

It is desirable that these cleansing compositions contain an anionic surfactant as the chief surfactant. No particular limitation is placed on the type of the anionic surfactant used. Specific examples thereof include alkyl ether sulfuric ester salts, polyoxyethylene alkyl ether sulfates, polyoxyethylene fatty acid monoethanolamide sulfates, alkylbenzenesulfonic acid salts, α-olefinsulfonic acid salts, lignin sulfonate, alkyl sulfosuccininate salts, fatty acid amide sulfosuccininates, higher fatty acid salts, polyoxyethylene alkyl ether acetates, N-acylglutamic acid salts, N-acylaspartic acid salts, N-acylsarcosine salts, N-acyl-β- alanine salts and monoalkyl phosphate salts. These anionic surfactants may be used alone or in combination. Specific examples of the base component include alkali metals such as sodium and potassium; alkaline earth metals such as magnesium; inorganic amines such as ammonia; organic amines such as monoethanolamine, diethanolamine and triethanolamine; and basic amino acids such as lysine and arginine.

The cleansing compositions can further contain other ingredients to such an extent as not to detract from the effects of the present invention. Specific examples thereof include cationic surfactants such as dimethyl polysiloxane and monoalkylammonium salts; nonionic surfactants such as fatty acid alkanolamides, polyoxyethylene hardened castor oil, alkyl polyglycosides and sucrose fatty acid esters; amphoteric surfactants such as N-alkylsulfobetaine, alkylaminoacetic acid betaine, acylamide propylbetaine and imidazolinium betaine; cationic polymers such as cationized cellulose derivatives, cationized guar gum, diallyl quaternary ammonium salt/acrylamide copolymer, quaternary polyvinyl pyrrolidone derivatives and methacryl-based amphoteric/cationic polymers; foaming agents such as higher fatty acids and higher alcohols; humectants such as glycerin, ethylene glycol, propylene glycol and sorbitol; emulsifiers such as glyceryl monostearate, sorbitan monopalmitate and polyoxyethylene cetyl ether; oily materials such as silicone oil, silicone derivatives, squalane, olive oil, castor oil and polyethylene glycol fatty acid esters; iridescent agents such as styrene polymer and diethylene glycol distearate; anti-dandruff agents such as zinc pyrithione; bactericides such as p-hydroxybenzoic acid esters; antiseptics; antioxidants; thickeners; ultraviolet absorbers such as benzophenone derivatives; pH regulators such as citric acid; pigments; and perfumes.

The cleansing compositions can be prepared by mixing a polyaspartic acid derivative in accordance with the present invention with other desired ingredient and stirring the resulting mixture according to any well-known technique. No particular limitation is placed on the form of the cleansing compositions, and they may be in the form of a liquid, cream, mousse, gel, solid, powder or the like.

Hairdressing spray compositions containing a polyaspartic acid derivative in accordance with the present invention preferably comprise the polyaspartic acid derivative, a solvent and a propellant. In recent years, aerosol sprays using, as propellant, a hydrocarbon (e.g., propane or butane) in place of halogenated hydrocarbons are increasing because of the problem of environmental protection. In such sprays, however, the presence of the hydrocarbon causes a reduction in the solubility of the polymer in the polymer solution (using an alcohol or the like as solvent), so that the solution may become in homogeneous and/or the polymer may separate out. In this situation, the spray forms a non-uniform film and/or causes a clogging of the valve. In contrast, hairdressing spray compositions containing a polyaspartic acid derivative in accordance with the present invention do not involve such problems and are hence suitable for use as new types of hairdressing aerosol sprays.

The solvent used in these hairdressing spray compositions serves to dilute the polyaspartic acid derivative or a solution thereof. For this purpose, it is desirable to use a solvent consisting essentially of water and/or a lower alcohol. In particular, a solvent selected from lower alcohols and mixtures thereof is preferred. This solvent may contain a relatively small amount of a hydrophilic solvent such as ethylene glycol, ethyl cellosolve, dioxane or methyl acetate. Specific examples of the lower alcohols include methanol, ethanol, propanol, isopropanol, 1-methoxypropanol and mixtures thereof, and they may contain water. Especially preferred are ethanol, an ethanol/isopropanol solvent mixture, water, a water/ethanol solvent mixture and a water/isopropanol solvent mixture.

Specific examples of the propellant used in these hairdressing spray compositions include propane, n-butane, isobutane, 2-dimethylpropane, isopentane and dimethyl ether. Moreover, hydrocarbons, chlorinated hydrocarbons, fluorocarbons, Freons, water, nitrogen, LPG, LNG, low-boiling organic liquids, carbon dioxide, inert gases and the like are also useful. Among them, liquefied gases of propane, n-butane, isobutane, 2,2-dimethylpropane, isopentane, dimethyl ether and mixtures thereof are preferred. These propellants may be used in combination with fluorinated hydrocarbons (e.g., difluorodichloromethane and fluorotrichloromethane), chlorinated hydrocarbons (e.g., methylene chloride), nitrogen, carbon dioxide and the like. An especially preferred propellant is a mixture of liquefied petroleum gas (composed of propane, n-butane and isobutane) and dimethyl ether.

Specific examples of fluorocarbons include Freons of the CFC series, such as CFC-11, CFC-12, CFC-113 and CFC-114. However, these conventional chlorofluorocarbons (CFCs) are destructive to the ozone layer and, therefore, their use is regulated. Accordingly, it is desirable to properly use new propellants and spraying techniques which conform to the regulations and clear the standards for environmental protection. Specific examples of substitutes for the aforesaid chlorofluorocarbons (CFCs) include hydrochlorofluorocarbons (HCFCs) and hydrofluorocarbons (HFCs). More specifically, they include HCFC-141b, HCFC-142b, HCFC-141b/142b, HFC-134a, HFC-143a, HCFC-22, HFC-32, CFC-1113, HFC-32, HFC-125, HCFC-124, HFC-125/HCFC-124, HFC-125, HFC-152a, HCFC-123 and HFC-4310.

In the hairdressing spray compositions, the polyaspartic acid derivative of the present invention is preferably used in an amount of 0.1 to 20% by weight, more preferably 0.5 to 15% by weight, based on the total amount of the composition. By choosing its amount used so as to be equal to or greater than a specific value (preferably 0.1% by weight and more preferably 0.5% by weight), the resulting hairdressing spray composition produces more excellent effects, for example, in that an improvement in hair-setting power can be achieved. On the other hand, by choosing its amount used so as to be equal to or less than a specific value (preferably 20% by weight and more preferably 15% by weight), the resulting hairdressing spray composition produces more excellent effects in that a feeling of stiffness and flaking can be prevented. The solvent is preferably used in an amount of 10 to 99.8% by weight, more preferably 10 to 89.5% by weight and most preferably 20 to 85% by weight, based on the total amount of the composition. By choosing its amount used so as to be equal to or greater than a specific value (preferably 10% by weight and most preferably 20% by weight), the resulting hairdressing spray composition produces more excellent effects, for example, in that a disagreeable feeling such as stiffness can be prevented. On the other hand, by choosing its amount used so as to be equal to or less than a specific value (preferably 99.8% by weight, more preferably 89.5% by weight and most preferably 85% by weight), the resulting hair-dressing spray composition produces more excellent effects, for example, in that an improvement in the drying rate of the applied spray can be achieved. The propellant is preferably used in an amount of 10 to 75% by weight, more preferably 15 to 65% by weight By choosing its amount used so as to be equal to or greater than a specific value (preferably 10% by weight and more preferably 15% by weight), the resulting hair-dressing spray composition produces more excellent effects, for example, in that a finer spray can be formed and an improvement in the drying rate of the applied spray can be achieved. On the other hand, by choosing its amount used so as to be equal to or less than a specific value (preferably 75% by weight and more preferably 65% by weight), the resulting hair-dressing spray composition produces more excellent effects in that an improvement in uniformity of application to the hair can be achieved as a result of moderate decrease in drying rate.

If necessary, the hairdressing spray compositions can further contain various well-known additives and assistants for use in hair cosmetics, to such an extent as not to detract from the effects of the present invention. Specific examples thereof include esters (e.g., isopropyl myristate and phthalic acid esters), polyhydric alcohols (e.g., glycerin, glycerin derivatives and polyethylene glycol), silicone compounds, oils (e.g., paraffin and squalane), lanolin, lanolin derivatives, isopropyl myristate, oleyl alcohol, dibutyl phthalate, pantothenyl alcohol, cationic, anionic, amphoteric and nonionic surfactants, cationic, anionic and nonionic hairdressing resins, water-soluble polymeric compounds and derivatives thereof, chelating agents, antioxidants, colorants (e.g., dyes, coatings and pigments), UV absorbers, antiseptics and perfumes. Moreover, various other polymers may also be added to such an extent as not to detract from the performance of the hairdressing spray compositions.

The hairdressing spray compositions may also be prepared in the form of a solution, a homogeneous dispersion or an inhomogeneous dispersion, provided that they do not cause a clogging of the valve. These hairdressing spray compositions can be obtained by packing the above-described three ingredients into spray containers according to any well-known technique. For example, the polyaspartic acid derivative or a salt thereof can be used as a spray by diluting it with a solvent, placing it in a container, and charging a propellant thereinto under pressure.

Hairdressing resin compositions containing a polyaspartic acid derivative in accordance with the present invention preferably comprise the polyaspartic acid derivative and a solvent. If it is tried to use conventionally known amphoteric ion-containing resins and anionic resins in the form of a hairdressing spray of the non-gas type (i.e., the type using no propellant), the size of the sprayed droplets is coarse, so that it is difficult to apply them uniformly to the hair. Consequently, such hairdressing sprays tend to have insufficient hair-setting power, undergo flaking, give an unnatural feel, and cause a clogging of the valve. In contrast, hair-dressing resin compositions containing a polyaspartic acid derivative in accordance with the present invention do not involve such problems and exhibit excellent hairdressing properties.

The solvent used in the hairdressing spray compositions desirably comprises water and/or a hydrophilic solvent. As used herein, the term "hydrophilic solvent" means any organic solvent having a solubility of not less than 10 g/100 g water (25° C.). Specific examples of the hydrophilic solvent include aliphatic mono- to tetrahydric alcohols such as methyl alcohol, ethyl alcohol, n-propyl alcohol, isopropyl alcohol, 1-methoxypropanol, ethylene glycol and diethylene glycol. Moreover, they also include methyl cellosolve, ethyl cellosolve, butyl cellosolve, dioxane, methyl acetate and dimethyl formamide. These hydrophilic solvents may be used alone or in admixture, and may be mixed with water. Among them, ethyl alcohol, n-propyl alcohol, isopropyl alcohol, a water/ethanol solvent mixture, a water/isopropanol solvent mixture and the like are preferred.

The proportion of the polyaspartic acid derivative in the hairdressing resin compositions is preferably in the range of about 0.1 to 20% by weight, more preferably about 0.5 to 15% by weight, based on the total amount of the composition. By choosing its proportion so as to be equal to or greater than a specific value (preferably 0.1% by weight and more preferably 0.5% by weight), the resulting hairdressing resin composition produces more excellent effects, for example, in that excellent hairdressing performance can be achieved. On the other hand, by choosing its proportion so as to be equal to or less than a specific value (preferably 20% by weight and more preferably 15% by weight), the resulting hairdressing resin composition produces more excellent effects, for example, in that a feeling of stiffness and flaking can be prevented.

In order to prepare the hairdressing resin compositions in the form of a hairdressing spray of the non-gas type, various additives and the like are usually incorporated therein. In such a case, various well-known additives and assistants for use in hair cosmetics may be added as required, to such an extent as not to detract from the effects of the present invention. Specific examples thereof include esters (e.g., isopropyl myristate and phthalic acid esters), polyhydric alcohols (e.g., glycerin, glycerin derivatives and polyethylene glycol), silicone compounds, oils (e.g., paraffin and squalane), lanolin, lanolin derivatives, isopropyl myristate, oleyl alcohol, dibutyl phthalate, pantothenyl alcohol, cationic, anionic, amphoteric and nonionic surfactants, cationic, anionic and nonionic hairdressing resins, water-soluble polymeric compounds and derivatives thereof, chelating agents, antioxidants, colorants (e.g., dyes, coatings and pigments), UV absorbers, antiseptics, perfumes and hair tonics. Moreover, various other polymers may also be added to such an extent as not to detract from the performance of the hairdressing resin compositions of the present invention.

Furthermore, the hairdressing resin compositions may also be prepared in the form of a solution, a homogeneous dispersion or an inhomogeneous dispersion, provided that they do not cause a clogging of the valve.

Hair dye compositions containing a polyaspartic acid derivative in accordance with the present invention preferably comprise the polyaspartic acid derivative, a pigment, and a solvent consisting essentially of water and/or a lower alcohol. In conventional hair dye compositions using a pigment as colorant and a resin as sticking agent, the resin generally comprises an anionic acrylic resin neutralized with an alkanolamine, an amphoteric ion-containing resin or the like. However, these resins for use in hair dyes do not have sufficient safety for the living body and hardly decompose under natural environmental conditions. Moreover, hairdressing compositions using a nonionic resin such as vinylpyrrolidone polymer or vinylpyrrolidone/vinyl acetate copolymer form a hard film on the hair and hence tend to undergo flaking. On the other hand, the film becomes very soft under high-temperature and high-humidity conditions, so that the set of the hair tends to be disordered. In contrast, hair dye compositions containing a polyaspartic acid derivative in accordance with the present invention do not involve such problems and are expected to exhibit excellent hairdressing properties, give a good gloss to the dyed hair, and have good biodegradability and high safety for the living body. Moreover, since the pigment is effectively dispersed by the action of the polyaspartic acid derivative, the pigment does not precipitate but remains in a stably dispersed state for a long period of time. Furthermore, a certain degree of hairdressing properties can be imparted to the dyed hair.

In the hair dye compositions, any of various well-known pigments can be used. Specific examples thereof include inorganic pigments such as carbon black, talc, kaolin, mica and titanium oxide; and organic pigments such as Red No. 202, Red No. 204, Red No. 205, Red No. 206, Red No. 219, Red No. 228, Yellow No. 205, Red No. 404, Orange No. 401, Yellow No. 401 and Blue No. 404. These pigments may be used alone or in admixture of two or more. If necessary, acid dyes such as Red No. 3, Red No. 104, Red No. 105, Yellow No. 4, Yellow No. 5, Green No. 3, Blue No. 1, Blue No. 2, Red No. 201, Red No. 225, Orange No. 207, Yellow No. 202, Green No. 205, Blue No. 203, Red No. 502, Orange No. 402 and Black No. 401 may be added thereto.

The solvent used in the hair dye compositions desirably comprises a solvent consisting essentially of water and/or a lower alcohol. This solvent may contain a relatively small amount of a hydrophilic solvent such as ethylene glycol, ethyl cellosolve, dioxane or methyl acetate. Specific examples of the lower alcohol include methanol, ethanol, propanol and isopropanol. Especially preferred are water, a water/ethanol solvent mixture and a water/isopropanol solvent mixture.

The proportion of the polyaspartic acid derivative in the hair dye compositions is preferably in the range of about 0.1 to 20% by weight, more preferably about 0.2 to 10% by weight, based on the total amount of the composition. By choosing its proportion so as to be equal to or greater than a specific value (preferably 0.1% by weight and more preferably 0.2% by weight), the resulting hair dye composition produces more excellent effects, for example, in that excellent hairdressing performance can be achieved. On the other hand, by choosing its proportion so as to be equal to or less than a specific value (preferably 20% by weight and more preferably 10% by weight), the resulting hair dye composition produces more excellent effects, for example, in that a feeling of stiffness and flaking can be prevented. The proportion of the pigment may be suitably determined according to the desired hair-dyeing power of the hair dye composition. Generally speaking, its proportion is preferably in the range of 0.1 to 10% by weight, more preferably 0.5 to 5% by weight, based on the total amount of the composition. By choosing its proportion so as to be equal to or greater than a specific value (preferably 0.1% by weight and more preferably 0.5% by weight), the resulting hair dye composition produces more excellent effects, for example, in that excellent hair-dyeing performance can be achieved. On the other hand, by choosing its proportion so as to be equal to or less than a specific value (preferably 10% by weight and more preferably 5% by weight), the resulting hair dye composition produces more excellent effects, for example, in that the dyed hair is glossy and smooth to the touch.

In addition to the above-described ingredients, the hair dye compositions can further contain various additives as required. Specific examples thereof include additives used for purposes of softening, lubrication, lustering and the like, such as lanolin, lanolin derivatives, glycerin, glycerin derivatives, isopropyl myristate, oleyl alcohol, dibutyl phthalate, silicone derivatives, polyethylene glycol, polyethylene glycol derivatives and pantothenyl alcohol. Moreover, they can also contain well-known additives such as surfactants, perfumes, colorants, antiseptics and gelling agents. Furthermore, various other polymers may also be added to such an extent as not to detract from the performance of the hair dye compositions.

These hair dye compositions can be prepared by dissolving or dispersing the polyaspartic acid derivative and the pigment in the solvent. In these hair dye compositions, the polyaspartic acid derivative of the present invention has the effect of dispersing the pigment stably in the composition. Consequently, the pigment in these hair dye compositions can remain in a stably dispersed state for a long period of time.

The subject matter of the present invention is more specifically explained with reference to the following examples and comparative examples. However, the examples and preparation examples given below and the above-described various embodiments are intended to facilitate the understanding of the subject matter of the present invention and are not to be construed to limit the technical scope of the present invention.

[Evaluation Procedures]

The evaluation procedures employed in the examples and comparative examples are given below.

(1) Evaluation of the weight-average molecular weight of the polysuccinimide

Using polystyrene as the standard substance, the weight-average molecular weight (hereinafter referred to as Mw) of the starting polysuccinimide was evaluated by GPC under the following conditions.

(GPC in a DMF system)
Apparatus: Jasco Corp. 880-PU
Detector: Shodex RID-300
Column: Shodex KD-804+KD-80M
Solvent: 0.01M LiBr/DMF
Concentration: 0.5% by weight
Amount injected: 20 µl
Flow rate: 1.0 ml/min (2) Evaluation of the weight-average molecular weight of the polyaspartic acid derivative The Mw of the polyaspartic acid derivative was evaluated by GPC under the following conditions. As the standard substance, polyethylene oxide was used for GPC in an aqueous system and polystyrene for GPC in a chloroform system.

(GPC in an aqueous system)
Apparatus: Jasco Corp. 880-PU
Detector: Jasco Corp. 830-RI
Column: Shodex OHpak B-804
Solvent: 0.1M KCl/water-methanol (8:2) solvent mixture
Concentration: 0.5% by weight
Amount injected: 20 µl
Flow rate: 0.4 ml/min (GPC in a chloroform system)
Apparatus & detector: Shodex GPC System-11
Column: Shodex K-805L
Solvent: Chloroform
Concentration: 0.5% by weight
Amount injected: 20 µl
Flow rate: 1.0 ml/min (3) Nuclear magnetic resonance spectra (NMR spectra)

After samples of the polyaspartic acid derivative were dissolved in deuterated dimethyl sulfoxide (dDMSO), or deuterated chloroform ($CDCl_3$), deuterated methanol ($CD_3OD$) or a deuterated chloroform/deuterated methanol mixture, or heavy water, its $^1$H-NMR spectrum (90 MHz), $^1$H-NMR spectrum (400 MHz) and $^{13}$C-NMR spectrum (400 MHz) were measured, respectively, by means of nuclear magnetic resonance measuring apparatus (Models FX-90 and EX-400; manufactured by Jeol Ltd.).

(4) IR analysis

IR analysis (infrared spectroscopic analysis) was made in the usual manner.

(5) Solubility

At 10% concentration, solubility of polymer in solvents of ethanol or ethanol/water mixture was rated as follows (as ethanol/water mixture, three types of 7/3, 5/5 and 3/7 were used):

In ethanol:
o, It was dissolved;
Δ, It was dissolved after heating;
X, It was not dissolved;

In ethanol/water:
o, It was dissolved (there is at least one of the mixture dissolving it);
Δ, It was dissolved after heating (there is at least one of the mixture dissolving it after heating);
X, It was not dissolved;

(6) Curl retention test 2 g of hair bundle having a length of 25 cm was washed with a 0.25 wt. % aqueous solution of sodium lauryl sulfate and dried. It was soaked in a 3 wt. % aqueous polymer solution [in water/ethanol mixture or ethanol]. Thereafter, the hair bundle was strongly squeezed between fingers five times to remove any excess polymer solution, wound around a rod having a diameter of 1.4 cm, fastened in place with rubber bands, and dried at 50° C. for 2 hours. The dried hair bundle was gently removed from the rod and suspended in a thermohygrostatic chamber maintained at 30° C. and 90% relative humidity. After 5 hours, the length of the curl was measured and the degree of curl retention (%) was calculated according to the following equation.

Curl retention (%)=[$(L-L_n)/(L-L_0)$]×100 where L is the original length (cm) of the hair bundle, $L_0$ is the length (cm) of the curl at time 0, and $L_n$ is the length (cm) of the curl after n hours.

(7) Flaking

Hair bundle was curled in the same manner as described for the evaluation of curl retention. The amount of resin flaked off by combing the curled hair bundle as rated as follows:
o, little resin was flaked off;
Δ, a little resin was flaked off;
X, much resin was flaked off or the hair felt very sticky.

(8) Feel

Hair bundle was curled in the same manner as described for the evaluation of curl retention. By touching the curled hair bundle with the hand, its feel was rated as follows:
o, the hair bundle was soft and pleasant to the touch;
Δ, the hair bundle was somewhat stiff or sticky;
X, the hair bundle was very stiff or sticky.

(9) Gloss

Hair bundle was curled in the same manner as described for the evaluation of curl retention. By observing the curled hair bundle, its gloss was rated as follows:
o, the hair bundle had a good gloss;
Δ, the hair bundle had some gloss;
X, the hair bundle had no gloss.

(10) Orderliness

Hair bundle was curled in the same manner as described for the evaluation of curl retention. Its orderliness was rated as follows:
o, the hair bundle was in good order;
Δ, the hair bundle was in rather good order;
X, the hair bundle was not in order.

(11) Overall evaluation

Based on the solubility, curl retention test, flaking, feel, gloss and orderliness, the overall evaluation was rated as follows:

X, Against (There is two or more marks X );
Δ, Favor (There is one or more marks X );
☐, Good; (There is no mark X and three or more marks Δ);
o, Excellent (There is no mark X , and one or two mark Δ, and curl retention is 40% or more);
◉, Most excellent (All marks are o, and curl retention is 70% or more);

The used amounts of polymer disclosed herein are numbers of moles of the repeating structure units if there is no specific mention. (In case of copolymers, they are numbers of moles of the repeating units based on the average molecular weight.)

[1] Examples Concerning Polyaspartic Acid Derivatives

EXAMPLE 1

(1) Reaction

A separable flask fitted with a stirrer, a heater, a thermometer and a nitrogen line was used as a reactor and the reaction system was fully stirred during the reaction. As the starting material, there was used polysuccinimide (having a Mw of 81,000 as measured by GPC in a DMF system) which had been fully dried by heating to 60° C. under reduced pressure. 19.4 g (0.2 mol) of this polysuccinimide (hereinafter referred to as PSI) was dissolved in 60 g of DMF at room temperature, and 9.3 g (0.05 mol) of n-laurylamine was added dropwise thereto. The DMF used as the reaction solvent had been dried with molecular sieves and by blowing dry nitrogen gas thereinto, and the water content in the reaction system was kept at 800 ppm or less during the reaction.

After completion of the addition, the reaction was carried out for 4 hours with the internal temperature of the reactor maintained at 60° C. After completion of the reaction with n-laurylamine, the reactor was cooled. When the internal temperature was 40° C. or below, 18.4 g (0.18 mol) of N,N-dimethyl-1,3-propanediamine was added dropwise and the reaction was continued at room temperature for another 4 hours. After completion of the reaction, the reaction mixture was subjected to the following isolation procedure.

(2) Isolation

The above reaction mixture was poured into 800 ml of a stirred acetone/hexane (5:2) solvent mixture which was a poor solvent for the resulting polyaspartic acid derivative, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative was isolated by drying the filter cake in a stream of hot air at 60° C. Its yield was 41.8 g (95%). The polyaspartic acid derivative was subjected to the following amphoterization reaction.

(3) Amphoterization reaction

A separable flask fitted with a stirrer, a heater, a thermometer and a nitrogen line was used as a reactor. 33.0 g (average repeating structure units 0.15 mol) of the above-isolated polyaspartic acid derivative was dissolved in 150 ml of ethanol at room temperature and charged into the reactor. Then, potassium monochloroacetate in an amount equal to 0.9 time the number of moles (0.135 mol) of the above-isolated polyaspartic acid derivative was added to the flask. After completion of the addition, the resulting mixture was reacted for another 14 hours under reflux in a stream of nitrogen. After completion of the reaction, the reaction mixture was concentrated to about 70 ml and filtered by suction to separate the precipitate. The separated precipitate was subjected to the following isolation procedure.

(4) Isolation after amphoterization

The above reaction mixture was poured into 700 ml of a stirred acetone/hexane (5:2) solvent mixture which was a poor solvent for the resulting polyaspartic acid derivative having amphoteric ions, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative having amphoteric ions was isolated by drying the filter cake in a stream of hot air at 60° C. Its yield was 34.3 g (97.0%). The polyaspartic acid derivative having amphoteric ions was subjected to the evaluations.

(5) Evaluation of the weight-average molecular weight

The product after the above amphoterization reaction was evaluated by GPC under the aqueous system. The average molecular weight (Mw) was 33,400.

EXAMPLE 2

(1) Reaction

A separable flask fitted with a stirrer, a heater, a thermometer and a nitrogen line was used as a reactor and the reaction system was fully stirred during the reaction. Starting PSI (having a Mw of 81,000 as measured by GPC in a DMF system) which had been fully dried by heating to 60° C. under reduced pressure. 19.4 g (0.2 mol) of PSI was dissolved in 60 g of DMF at room temperature, and 18.5 g (0.1 mol) of n-laurylamine was added dropwise thereto. The DMF used as the reaction solvent had been dried with molecular sieves and by blowing dry nitrogen gas thereinto, and the water content in the reaction system was kept at 800 ppm or less during the reaction.

After completion of the addition, the reaction was carried out for 4 hours with the internal temperature of the reactor maintained at 60° C. After completion of the reaction with n-laurylamine, the reactor was cooled. When the internal temperature was 40° C. or below, 12.3 g (0.12 mol) of N,N-dimethyl-1,3-propane diamine was added dropwise and the reaction was continued 40° C. for another 4 hours. After completion of the reaction, the reaction mixture was subjected to the following isolation procedure.

(2) Isolation

The above reaction mixture was poured into 800 ml of a stirred acetone/hexane (5:2) solvent mixture which was a poor solvent for the resulting polyaspartic acid derivative, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative was isolated by drying the filter cake in a stream of hot air at 60° C. Its yield was 46.7 g (97%). The polyaspartic acid derivative was subjected to the following amphoterization reaction.

(3) Amphoterization reaction

A separable flask fitted with a stirrer, a heater, a thermometer and a nitrogen line was used as a reactor. 36.1 g (average repeating structure units 0.15 mol) of the above-isolated polyaspartic acid derivative was dissolved in 150 ml of ethanol/chloroform (5:3) at room temperature and charged into the reactor. Then, potassium monochloroacetate in an amount equal to 0.6 time the number of moles (0.09 mol) of the above-isolated polyaspartic acid derivative was added to the flask. After completion of the addition, the resulting mixture was reacted for another 14 hours under reflux in a stream of nitrogen. After completion of the reaction, the reaction mixture was concentrated to about 70 ml and filtered by suction to separate the precipitate. The separated precipitate was subjected to the following isolation procedure.

(4) Isolation after amphoterization

The above reaction mixture was poured into 800 ml of a stirred acetone/hexane (5:1) solvent mixture which was a poor solvent for the resulting polyaspartic acid derivative having amphoteric ions, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative having amphoteric ions was isolated by drying the filter cake in a stream of hot air at 60° C. Its yield was 40.6 g (95.0%). The polyaspartic acid derivative having amphoteric ions was subjected to the evaluations.

(5) Evaluation of the weight-average molecular weight

The product after the above amphoterization reaction was evaluated by GPC under the aqueous system and under the chloroform system. The average molecular weight (Mw) were 119,000 (aqueous system) and 1,642,000 (chloroform system).

EXAMPLE 3

(1) Reaction

A separable flask fitted with a stirrer, a heater, a thermometer and a nitrogen line was used as a reactor and the reaction system was fully stirred during the reaction. Starting PSI (having a Mw of 156,000 as measured by GPC in a DMF system) which had been fully dried by heating to 60° C. under reduced pressure. 19.4 g (0.2 mol) of PSI was dissolved in 60 g of DMF at room temperature, and 18.5 g (0.1 mol) of n-laurylamine was added dropwise thereto. The DMF used as the reaction solvent had been dried with molecular sieves and by blowing dry nitrogen gas thereinto, and the water content in the reaction system was kept at 800 ppm or less during the reaction After completion of the addition, the reaction was carried out for 4 hours with the internal temperature of the reactor maintained at 60° C. After completion of the reaction with n-laurylamine, the reactor was cooled. When the internal temperature was 40° C. or below, 12.3 g (0.12 mol) of N,N-dimethyl-1,3-propanediamine was added dropwise and the reaction was continued 40° C. for another 4 hours. After completion of the reaction, the reaction mixture was subjected to the following isolation procedure.

(2) Isolation

The above reaction mixture was poured into 800 ml of a stirred acetone/hexane (5:2) solvent mixture which was a poor solvent for the resulting polyaspartic acid derivative, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative was isolated by drying the filter cake in a stream of hot air at 60° C. Its yield was 47.2 g (98%). The polyaspartic acid derivative was subjected to the following amphoterization reaction.

(3) Amphoterization reaction

A separable flask fitted with a stirrer, a heater, a thermometer and a nitrogen line was used as a reactor. 36.1 g (average repeating structure units 0.15 mol) of the above-isolated polyaspartic acid derivative was dissolved in 150 ml of ethanol/chloroform (6:4) at room temperature and charged into the reactor. Then, potassium monochloroacetate in an amount equal to 0.6 time the number of moles (0.09 mol) of the above-isolated polyaspartic acid derivative was added to the flask. After completion of the addition, the resulting mixture was reacted for another 14 hours under reflux in a stream of nitrogen. After completion of the reaction, the reaction mixture was concentrated to about 70 ml and filtered by suction to separate the precipitate. The separated precipitate was subjected to the following isolation procedure.

(4) Isolation after amphoterization

The above reaction mixture was poured into 700 ml of a stirred acetone/hexane (5:2) solvent mixture which was a poor solvent for the resulting polyaspartic acid derivative having amphoteric ions, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative having amphoteric ions was isolated by drying the filter cake in a stream of hot air at 60° C. Its yield was 40.1 g (99.0%). The polyaspartic acid derivative having amphoteric ions was subjected to the evaluations.

(5) Evaluation of the weight-average molecular weight

The product after the above amphoterization reaction was evaluated by GPC under the chloroform system. The average molecular weight (Mw) were 53,600.

When the $^1$H-NMR spectrum of the resulting polyaspartic acid derivatives (hereinafter referred to as n-laurylamine amphoteric derivatives) obtained in Examples 1 to 3 were recorded, the following peaks were detected (CDCl$_3$/CD$_3$OD=1/1).

0.9 ppm (C$\underline{H}_3$—, n-laurylamine)
1.2–1.4 ppm (CH$_3$—(C$\underline{H}_2$)$_9$—, n-laurylamine)
1.5 ppm (—C$\underline{H}_2$—CH$_2$—NH—, n-laurylamine)
2.0 ppm (—C$\underline{H}_2$—CH$_2$—N$^+$—, amphoteric ion)
2.6–3.0 ppm (—C$\underline{H}_2$—, ring-opened PSI)
3.1–3.4 ppm (—N$^+$—(C$\underline{H}_3$)$_2$—, amphoteric ion; —CONH—C$\underline{H}_2$—, amphoteric ion; —CONH—C$\underline{H}_2$—, n-laurylamine)
3.6 ppm (—N$^+$—C$\underline{H}_2$COO$^-$, amphoteric ion)
3.8 ppm (C$\underline{H}_2$—N$^+$—, amphoteric ion)
4.5 ppm (—C$\underline{H}$—, ring-opened PSI)

Since a peak (at 5.1 ppm) characteristic of the methine proton of PSI was not detected, it is presumed that no unreacted PSI repeating unit was present in the resulting n-laurylamine amphoteric derivatives. Moreover, since a peak (at 1.8 ppm) characteristic of the [—CH$_2$—CH$_2$—CH$_2$—N(CH$_3$)$_2$] protons of dimethylaminopropylamine was not detected, it is believed that all the dimethylaminopropylamine was made amphoteric.

When the $^{13}$C-NMR spectrum of the resulting n-laurylamine amphoteric derivatives were recorded, the following peaks were detected (CDCl$_3$/CD$_3$OD=1/1).

14 ppm (C$\underline{H}_3$—, n-laurylamine)
23.0 ppm (CH$_3$—C$\underline{H}_2$—, n-laurylamine; C$\underline{H}_2$—CH$_2$—N$^+$—, amphoteric ion)
26.7 ppm (CONH—(CH$_2$)$_2$—C$\underline{H}_2$—, n-laurylamine)
30 ppm (CONH—CH$_2$—C$\underline{H}_2$—, n-laurylamine)
32.2 ppm (CH$_3$—CH$_2$—C$\underline{H}_2$—, n-laurylamine)
36.4–38.4 ppm (—C$\underline{H}_2$—, ring-opened PSI)
40.2 ppm (CONH—C$\underline{H}_2$—, n-laurylamine)
43 ppm (CONH—C$\underline{H}_2$—, amphoteric ion)
52 ppm (—N$^+$—(C$\underline{H}_3$)$_2$—, amphoteric ion)
60.4–65.8 ppm (—C$\underline{H}_2$N$^+$(CH$_3$)—C$\underline{H}_2$—, amphoteric ion)
168 ppm (—CH$_2$—C$\underline{\text{C}}$OO$^-$, amphoteric ion)

When the IR spectrum of the resulting n-laurylamine amphoteric derivatives were recorded, the following peaks were detected.

1660 cm$^{-1}$, 1540 cm$^{-1}$ (absorption by the amide group of the ring-opened PSI)

Since a peak (at 1750 cm$^{-1}$) characteristic of the imide ring of PSI was not detected, it is presumed that no unreacted PSI repeating unit was present in the resulting n-laurylamine amphoteric derivatives.

EXAMPLE 4

(1) Reaction

A separable flask fitted with a stirrer, a heater, a thermometer and a nitrogen line was used as a reactor and the reaction system was fully stirred during the reaction. Starting PSI (having a Mw of 81,000 as measured by GPC in a DMF system) which had been fully dried by heating to 60° C. under reduced pressure. 19.4 g (0.2 mol) of PSI was dissolved in 60 g of DMF at room temperature, and 9.2 g (0.034 mol) of n-stearylamine was added thereto. The DMF used as the reaction solvent had been dried with molecular sieves and by blowing dry nitrogen gas thereinto, and the water content in the reaction system was kept at 800 ppm or less during the reaction.

After completion of the addition, the reaction was carried out for 4 hours with the internal temperature of the reactor maintained at 60° C. After completion of the reaction with n-stearylamine, the reactor was cooled. When the internal temperature was 40° C. or below, 20.4 g (0.2 mol) of N,N-dimethyl-1,3-propanediamine was added dropwise and the reaction was continued at 40° C. for another 4 hours. After completion of the reaction, the reaction mixture was subjected to the following isolation procedure.

(2) Isolation

The above reaction mixture was poured into 800 ml of a stirred acetone/hexane (5:2) solvent mixture which was a poor solvent for the resulting polyaspartic acid derivative, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative was isolated by drying the filter cake in a stream of hot air at 60° C. Its yield was 43.7 g (96%). The polyaspartic acid derivative so isolated was subjected to the following amphoterization reaction.

(3) Amphoterization reaction

A separable flask fitted with a stirrer, a heater, a thermometer and a nitrogen line was used as a reactor. 36.1 g (average repeating structure units 0.15 mol) of the above-isolated polyaspartic acid derivative was dissolved in 150 ml of ethanol at room temperature and charged into the reactor. Then, potassium monochloroacetate in an amount equal to 1 time the number of moles (0.15 mol) of the above-isolated polyaspartic acid derivative was added to the flask. After completion of the addition, the resulting mixture was reacted for another 14 hours under reflux in a stream of nitrogen. After completion of the reaction, the reaction mixture was concentrated to about 70 ml and filtered by suction to separate the precipitate. The separated precipitate was subjected to the following isolation procedure.

(4) Isolation after amphoterization

The above reaction mixture was poured into 700 ml of a stirred acetone/hexane (5:3) solvent mixture which was a poor solvent for the resulting polyaspartic acid derivative having amphoteric ions, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative having amphoteric ions was isolated by drying the filter cake in a stream of hot air at 60° C. Its yield was 39.3 g (95.0%). The polyaspartic acid derivative having amphoteric ions was subjected to the evaluations.

(5) Evaluation of the weight-average molecular weight

The product after the above amphoterization reaction was evaluated by GPC under the chloroform system. The average molecular weight (Mw) were 2,000,000.

EXAMPLE 5

(1) Reaction

A separable flask fitted with a stirrer, a heater, a thermometer and a nitrogen line was used as a reactor and the reaction system was fully stirred during the reaction. Starting PSI (having a Mw of 77,000 as measured by GPC in a DMF system) which had been fully dried by heating to 60° C. under reduced pressure. 19.4 g (0.2 mol) of PSI was dissolved in 60 g of DMF at room temperature, and 13.5 g (0.05 mol) of n-stearylamine was added dropwise thereto. The DMF used as the reaction solvent had been dried with molecular sieves and by blowing dry nitrogen gas thereinto, and the water content in the reaction system was kept at 800 ppm or less during the reaction.

After completion of the addition, the reaction was carried out for 4 hours with the internal temperature of the reactor maintained at 60° C. After completion of the reaction with n-stearylamine, the reactor was cooled. When the internal temperature was 40° C. or below, 18.4 g (0.18 mol) of N,N-dimethyl-1,3-propanediamine was added dropwise and the reaction was continued at 40° C. for another 4 hours. After completion of the reaction, the reaction mixture was subjected to the following isolation procedure.

(2) Isolation

The above reaction mixture was poured into 800 ml of a stirred acetone/hexane (5:2) solvent mixture which was a poor solvent for the resulting polyaspartic acid derivative, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative was isolated by drying the filter cake in a stream of hot air at 60° C. Its yield was 45.3 g (94%). The polyaspartic acid derivative was subjected to the following amphoterization reaction.

(3) Amphoterization reaction

A separable flask fitted with a stirrer, a heater, a thermometer and a nitrogen line was used as a reactor. 36.2 g (average repeating structure units 0.15 mol) of the above-isolated polyaspartic acid derivative was dissolved in 150 ml of ethanol/chloroform (1:1) at room temperature and charged into the reactor. Then, potassium monochloroacetate in an amount equal to 0.9 time the number of moles (0.135 mol) of the above-isolated polyaspartic acid derivative was added to the flask. After completion of the addition, the resulting mixture was reacted for another 14 hours under reflux in a stream of nitrogen. After completion of the reaction, the reaction mixture was concentrated to about 70 ml and filtered by suction to separate the precipitate. The separated precipitate was subjected to the following isolation procedure.

(4) Isolation after amphoterization

The above reaction mixture was poured into 700 ml of a stirred acetone which was a poor solvent for the resulting polyaspartic acid derivative having amphoteric ions, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the polyaspartic acid derivative having amphoteric ions was isolated by drying the filter cake in a stream of hot air at 60° C. Its yield was 41.0 g (96.0%). The polyaspartic acid derivative having amphoteric ions was subjected to the evaluations.

(5) Evaluation of the weight-average molecular weight

The product after the above amphoterization was evaluated by GPC under the chloroform system. The average molecular weight (Mw) were 2,429,200.

When the $^1$H-NMR spectrum of the resulting polyaspartic acid derivatives (hereinafter referred to as n-stearylamine amphoteric derivatives) obtained in Examples 4 and 5 were recorded, the following peaks were detected ($CDCl_3$/$CD_3OD$=1/1).

0.9 ppm ($C\underline{H}_3$—, n-stearylamine)
1.1–1.7 ppm ($CH_3$—($C\underline{H}_2$)$_{16}$—, n-stearylamine)
2.0 ppm (—$C\underline{H}_2$—$CH_2$—$N^+$—, amphoteric ion)
2.6–3.0 ppm (—$C\underline{H}_2$—, ring-opened PSI)
3.1–3.4 ppm (—$N^+$—($C\underline{H}_3$)$_2$—, amphoteric ion; —$CONH$—$C\underline{H}_2$—, amphoteric ion; —$CONH$—$C\underline{H}_2$—, n-stearylamine)
3.6 ppm (—$N^+$—$C\underline{H}_2COO^-$, amphoteric ion)
3.8 ppm ($C\underline{H}_2$—$N^+$—, amphoteric ion)
4.5 ppm (—$C\underline{H}$—, ring-opened PSI)

Since a peak (at 5.1 ppm) characteristic of the methine proton of PSI was not detected, it is presumed that no unreacted PSI repeating unit was present in the resulting n-stearylamine amphoteric derivatives. Moreover, since a peak (at 1.8 ppm) characteristic of the [—$CH_2$—$CH_2$—$CH_2$—$N(CH_3)_2$] protons of dimethylaminopropylamine was not detect, it is believed that all the dimethylaminopropylamine was made amphoteric.

When the $^{13}$C-NMR spectrum of the resulting n-stearylamine amphoteric derivatives were recorded, the following peaks were detected ($CDCl_3$/$CD_3OD$=1/1).

14 ppm ($\underline{C}H_3$—, n-stearylamine)
23.0 ppm ($CH_3$—$\underline{C}H_2$—, n-stearylamine; $\underline{C}H_2$—$CH_2$—$N^+$—, amphoteric ion)
26.7 ppm ($CONH$—($CH_2$)$_2$—$\underline{C}H_2$—, n-stearylamine)
30 ppm ($CONH$—$CH_2$—$\underline{C}H_2$—, n-stearylamine)
32.2 ppm ($CH_3$—$CH_2$—$\underline{C}H_2$, n-stearylamine)
36.4–38.4 ppm (—$\underline{C}H_2$—, ring-opened PSI)
40.2 ppm ($CONH$—$\underline{C}H_2$—, n-stearylamine)
43 ppm ($CONH$—$\underline{C}H_2$, amphoteric ion)
52 ppm (—$N^+$—($\underline{C}H_3$)$_2$, amphoteric ion)
60.4–65.8 ppm (—$\underline{C}H_2N^+$($CH_3$)$_2$—$\underline{C}H_2$—, amphoteric ion)
168 ppm (—$CH_2$—$\underline{C}OO^-$, amphoteric ion)

When the IR spectrum of the resulting n-stearylamine amphoteric derivatives were recorded, the following peaks were detected.

1660 cm$^{-1}$, 1540 cm$^{-1}$ (absorption by the amide group of the ring-opened PSI)

Since a peak (at 1750 cm$^{-1}$) characteristic of the imide ring of PSI was not detected, it is presumed that no unreacted PSI repeating unit was present in the resulting n-stearylamine amphoteric derivatives.

[Reaction and isolation in Examples 6 to 45]

In Examples 6 to 45, the same procedures as described in steps (1) to (4) of Example 1 were repeated, except that the molecular weight of PSI, the types of the diamines and hydrophobic amines used, the proportions of these amines to PSI and reaction temperature were altered as shown in Tables 1 to 3.

[Evaluation of Examples 1 to 45]

The polyaspartic acid derivatives obtained in Examples 1 to 45 were evaluated according to the previously described procedures. The results thus obtained are shown in Tables 5 to 7.

[Comparative Example 1]

(1) Reaction

The same reactor as described in Example 1 was used, and the reaction system was fully stirred during the reaction. Starting PSI (having a Mw of 81,000 as measured by GPC in a DMF system) which had been fully dried by heating to 60° C. under reduced pressure. 19.4 g (0.2 mol) of PSI was dissolved in 60 g of DMF at room temperature, and 7.4 g (0.04 mol) of n-laurylamine was added dropwise thereto. After completion of the addition, the reaction was carried out for 4 hours with the internal temperature of the reactor maintained at 60° C. After completion of the reaction, the reaction mixture was subjected to the following isolation procedure.

(2) Isolation

The above reaction mixture was poured into 800 ml of stirred methanol which was a poor solvent for the resulting polyaspartic acid derivative (hereinafter referred to as LA derivative), thereby precipitating the derivative. This suspension was filtered by suction, so that the LA derivative was separated as filter cake. Moreover, this filter cake was dispersed in the aforesaid poor solvent and the resulting suspension was stirred and filtered by suction. The LA derivative was thoroughly washed by repeating this procedure several times. Thereafter, the resulting LA derivative was isolated by drying the filter cake in a stream of hot air at 60° C. Its yield was 25.2 g (94%) and its Mw was 33,000 as measured by GPC in a DMF system.

(3) Hydrolysis reaction

Using the same reactor as described in Example 1, 20.1 g (0.15 mol) of the above-isolated LA derivative was suspended in 150 ml of distilled water. To this suspension, 60 ml of a 2N aqueous solution of sodium hydroxide was slowly added dropwise at room temperature with care taken to keep the pH of the reaction system within the range of 9 to 12. After completion of the addition, the reaction mixture was subjected to the following isolation procedure.

(4) Isolation of the hydrolyzate

The above reaction mixture was poured into 800 ml of stirred acetone which was a poor solvent for the resulting LA derivative hydrolyzate, thereby precipitating the derivative hydrolyzate. This suspension was filtered by suction, so that the derivative hydrolyzate was separated as filter cake. Moreover, this filter cake was dispersed in the aforesaid poor solvent and the resulting suspension was stirred and filtered by suction. The LA derivative hydrolyzate was thoroughly washed by repeating this procedure several times. Thereafter, the resulting LA derivative hydrolyzate was isolated by drying the filter cake in a stream of hot air at 60° C. Its yield was 20.2 g (98%) and its Mw was 38,200 as measured by GPC in an aqueous system. The resulting LA derivative hydrolyzate was subjected to the evaluations.

[Comparative Example 2]

(1) Reaction

The same reactor as described in Example 1 was used, and the reaction system was fully stirred during the reaction. Starting PSI o(having a Mw of 81,000 as measured by GPC in a DMF system) which had been fully dried by heating to 60° C. under reduced pressure. 11.7 g (0.12 mol) of PSI was dissolved in 125 g of DMF at room temperature, and the resulting solution was added dropwise to a suspension of 1.85 g (0.024 mol) of cysteamine in 75 ml of DMF. After completion of the addition, the reaction was carried out at room temperature for 24 hours. After completion of the reaction, the reaction mixture was subjected to the following isolation procedure.

(2) Isolation

Since the above reaction mixture gelled upon completion of the reaction and was highly viscous, its viscosity was reduced by the addition of 50 ml of DMF. Then, the reaction mixture was poured into 600 ml of stirred ethanol which was a poor solvent for the resulting polyaspartic acid derivative (hereinafter referred to as CA derivative), thereby precipitating the derivative. This CA derivative suspension was filtered by suction, so that the resulting CA derivative was separated as filter cake. Moreover, this filter cake was dispersed in the aforesaid poor solvent and the resulting suspension was stirred and filtered by suction. The CA derivative was thoroughly washed by repeating this procedure several times. Thereafter, the resulting CA derivative was isolated by drying the filter cake in a stream of hot air at 60° C. Its yield was 13.2 g (98%). The resulting CA derivative was subjected to the following hydrolysis reaction.

(3) Evaluation of the weight-average molecular weight

The CA derivative was evaluated by GPC under the DMF system. Mw were 124,000.

(4) IR analysis

When the IR spectrum of the resulting CA derivative was recorded, the following peaks were detected. 1750 cm$^{-1}$ (absorption by the imide ring of PSI) 1650 cm$^{-1}$, 1540 cm$^{-1}$ (absorption by the amide group of the ring-opened PSI)

As a result, it is presumed that unreacted PSI repeating units remained in the resulting CA derivative.

(5) Hydrolysis reaction 5.0 g (0.044 mol) of the CA derivative obtained in the above step (1) was suspended in 50 ml of distilled water, and 17.7 ml of 2N sodium hydroxide was added dropwise thereto at room temperature. This addition was slowly performed with care taken to keep the pH of the reaction system within the range of 9 to 12. Since the reaction mixture gelled during the reaction, 50 ml of distilled water was added thereto so as to facilitate stirring. After completion of the addition, the reaction mixture was freeze-dried to obtain 5.72 g of powder in a 90% yield.

(6) IR analysis

When the IR spectrum of the resulting CA derivative hydrolyzate was recorded, the following peaks were detected.

1650 cm$^{-1}$, 1540 cm$^{-1}$ (absorption by the amide group of the ring-opened PSI)

As a result, it is presumed that no unreacted PSI repeating unit remained in the resulting CA derivative hydrolyzate.

[Comparative Example 3]

(1) Reaction

The same reactor as described in Example 1 was used, and the reaction system was fully stirred during the reaction. Starting PSI (having a Mw of 81,000 as measured by GPC in a DMF system) which had been fully dried by heating to 60° C. under reduced pressure. 19.4 g (0.2 mol) of PSI was dissolved in 60 g of DMF at room temperature, and 20.4 g (0.2 mol) of N,N-dimethyl-1,3-propanediamine was added dropwise therein. After completion of the addition, the reaction was continued at room temperature for 4 hours. DMF used as the reaction solvent had been dried with molecular sieves and by blowing dry nitrogen gas thereinto, and the water content in the reaction system was kept at 800 ppm or less during the reaction. After completion of the reaction, the reaction mixture was subjected to the following isolation procedure.

(2) Isolation

The above reaction mixture was poured into 800 ml of stirred acetone/hexane (5:3) which was a poor solvent for the resulting polyaspartic acid derivative, thereby precipitating the derivative. This suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the resulting polyaspartic acid derivative was isolated by drying the filter cake in a stream of hot air at 60° C. Its yield was 38.3 g (96%)

[Comparative Example 4]

(1) Reaction

The same reactor as described in Example 1 was used, and the reaction system was fully stirred during the reaction. Starting PSI (having a Mw of 81,000 as measured by GPC in a DMF system) which had been fully dried by heating to 60° C. under reduced pressure. 19.4 g (0.2 mol) of PSI was suspended in 300 ml of distilled water, and 100 ml of 2N sodium hydroxide was added dropwise thereto at room temperature. This addition was slowly performed with care taken to keep the pH of the reaction system within the range of 9 to 12. After completion of the addition, it was subjected to the following isolation procedure.

(2) Isolation

The reaction mixture was concentrated to about 150 ml by suction filtrate, and poured stirred 800 ml of ethanol, thereby precipitating the sodium salt of polyaspartic acid (hereinafter referred to as PAsp-Na). The resulting PAsp-Na was filtered by suction, so that the derivative was separated as filter cake. Moreover, this filter cake was dispersed in the aforesaid poor solvent and the resulting suspension was stirred and filtered by suction. The resulting PAsp-Na was thoroughly washed by repeating this procedure several times. Thereafter, the resulting PAsp-Na was isolated by drying the filter cake in a stream of hot air at 60° C. Its yield was 27.1 g (99%) and its Mw was 124,000 as measured by GPC in a water system.

[Comparative Example 5]

(1) Reaction

The same reactor as described in Example 1 was used, and the reaction system was fully stirred during the reaction. Starting PSI (having a Mw of 81,000 as measured by GPC in a DMF system) which had been fully dried by heating to 60° C. under reduced pressure. 19.4 g (0.2 mol) of PSI was dissolved in 60 g of DMF at room temperature, and 9.3 g (0.05 mol) of n-laurylamine was added dropwise thereto. The DMF used as the reaction solvent had been dried with molecular sieves and by blowing dry nitrogen gas thereinto, and the water content in the reaction system was kept at 800 ppm or less during the reaction.

After completion of the addition, the reaction was carried out for 4 hours with the internal temperature of the reactor maintained at 60° C. After completion of the reaction with n-laurylamine, the reactor was cooled. When the internal temperature was 40° C. or below, 18.4 g (0.18 mol) of N,N-dimethyl-1,3-propanediamine was added dropwise and the reaction was continued at room temperature for another 4 hours. After completion of the reaction, the reaction mixture was subjected to the following isolation procedure.

(2) Isolation

The above reaction mixture was poured into 800 ml of a stirred acetone/hexane (5:2) solvent mixture which was a poor solvent for the resulting polyaspartic acid derivative, thereby precipitating the derivative. This derivative suspension was filtered by suction, so that the derivative was separated as filter cake. Moreover, this filter cake was dispersed in the aforesaid poor solvent and the resulting suspension was stirred and filtered by suction. The derivative was thoroughly washed by repeating this procedure several times. Thereafter, the resulting polyaspartic acid derivative was isolated by drying the filter cake in a stream of hot air at 60° C. Its yield was 40.5 g (92%).

Comparative Examples 1 to 5 were evaluated according to the same procedures as in Examples 1 to 45, and the results thus obtained are shown in Table 4.

TABLE 1

| | | | | | Reaction | | | | | | | | |
|---|---|---|---|---|---|---|---|---|---|---|---|---|---|
| | | Hydrophobic amines | | | Amines *1 | | | Amphoterizing agent*2 | | Products Composition (mol %) | | | |
| Ex. | PSI | Type | mol % /PSI | temp °C. | Type | mol % /PSI | temp °C. | Type | mol % /PSI | Hydrophobic group | | Ampho-teric | Others *3 |
| 6 | 96,000 | — | — | — | DAP | 50 | r.t. | CK | 60 | — | | 50 | PSI 50 |
| 7 | 96,000 | — | — | — | DAP | 120 | r.t. | CNa | 120 | — | | 100 | — |
| 8 | 91,000 | Diethylamine | 25 | r.t. | DAP | 90 | r.t. | CK | 90 | Diethyl group | 25 | 75 | — |
| 9 | 91,000 | Ethanolamine | 25 | r.t. | DAP | 90 | r.t. | CNa | 90 | Ethanol group | 25 | 75 | — |
| 10 | 80,000 | Diethanolamine | 25 | r.t. | DAP | 90 | r.t. | CNa | 90 | Diethanol group | 25 | 75 | — |
| 11 | 90,000 | n-Propylamine | 70 | r.t. | DAP | 36 | r.t. | CNa | 36 | n-Propyl group | 70 | 30 | — |

TABLE 1-continued

| | | Hydrophobic amines | | | Reaction Amines *1 | | | Amphoterizing agent*2 | | Products Composition (mol %) | | | |
|---|---|---|---|---|---|---|---|---|---|---|---|---|---|
| Ex. | PSI | Type | mol %/PSI | temp °C. | Type | mol %/PSI | temp °C. | Type | mol %/PSI | Hydrophobic group | | Amphoteric | Others *3 |
| 12 | 88,000 | Isopropylamine | 50 | r.t. | DAP | 60 | r.t. | CNa | 60 | Isopropyl group | 50 | 50 | — |
| 13 | 88,000 | Cyclohexylamine | 25 | r.t. | DAP | 90 | r.t. | CNa | 90 | Cyclohexylgroup | 25 | 75 | — |
| 14 | 88,000 | sec-Butylamine | 60 | r.t. | DAP | 5 | r.t. | CK | 5 | sec-Butyl group | 60 | 5 | PSI 35 |
| 15 | 88,000 | tert-Butylamine | 16 | r.t. | DAP | 100 | r.t. | CK | 100 | tert-Butyl group | 16 | 84 | — |
| 16 | 91,000 | n-Butylamine | 25 | r.t. | DAP | 90 | r.t. | CNa | 90 | n-Butyl group | 25 | 75 | — |
| 17 | 81,000 | n-Butylamine | 70 | r.t. | DAP | 36 | r.t. | CNa | 36 | n-Butyl group | 70 | 30 | — |
| 18 | 90,000 | 3-(2-Ethylhexyloxy)propylamine | 25 | r.t. | DAP | 90 | r.t. | CK | 90 | 3-(2-Ethylhexyloxy) plopyl group | 25 | 75 | — |
| 19 | 91,000 | Hexylamine | 25 | r.t. | DAP | 90 | r.t. | CK | 90 | Hexyl group | 25 | 75 | — |
| 20 | 90,000 | Hexylamine | 95 | r.t. | DAP | 6 | r.t. | CK | 6 | Hexyl group | 95 | 5 | — |
| 21 | 55,000 | n-Octylamine | 25 | r.t. | DAP | 75 | r.t. | CK | 90 | Octyl group | 25 | 75 | — |
| 22 | 81,000 | n-Laurylamine | 25 | 60 | DAP | 90 | r.t. | CK | 5 | N-Lauryl group | 25 | 5 | Dimethylaminopropyl group 70 |
| 23 | 77,000 | n-Laurylamine | 25 | 60 | DMEA | 90 | r.t. | CK | 90 | n-Lauryl group | 25 | 75 | — |
| 24 | 77,000 | n-Laurylamine | 25 | 60 | DBPA | 90 | r.t. | CK | 90 | n-Lauryl group | 25 | 75 | — |

*[1]DAP, Dimethylaminopropylamine (N,N-Dimethyl-1,3-propanediamine); DMEA, Dimethylaminoethylamine (N,N-Dimethyl-1,2-ethyldiamine); DBPA, Dibutylaminopropylamine (N,N-Dibutyl-1,3-propanediamine).
*[2]CK, Potassium chloroacetate; CNa, Sodium chloroacetate.
*[3]PSI, Polysuccinimide.

TABLE 2

| | | Hydrophobic amines | | | Reaction Amines *1 | | | Amphoterizing agent*2 | | Products Composition (mol %) | | | |
|---|---|---|---|---|---|---|---|---|---|---|---|---|---|
| Ex. | PSI | Type | mol %/PSI | temp °C. | Type | mol %/PSI | temp °C. | Type | mol %/PSI | Hydrophobic group | | Amphoteric | Others *3 |
| 25 | 81,000 | n-Laurylamine | 40 | 60 | DAP | 72 | 40 | CK | 50 | n-Lauryl group | 40 | 50 | Dimethylaminopropyl group 10 |
| 26 | 56,000 | n-Laurylamine Hexylamine | 50 20 | 60 40 | DAP | 36 | 40 | CK | 36 | n-Lauryl group Hexyl group | 50 20 | 30 | — |
| 27 | 80,000 | n-Stearylamine n-Laurylamine | 10 25 | 60 60 | DAP | 78 | 40 | CK | 78 | n-Stearyl group n-Lauryl group | 10 25 | 65 | — |
| 28 | 100,000 | n-Stearylamine | 15 | 60 | DAP | 102 | 40 | CK | 6 | n-Stearyl group | 15 | 5 | Dimethylaminopropyl group 80 |
| 29 | 56,000 | n-Stearylamine | 15 | 60 | DAP | 102 | 40 | CNa | 102 | n-Stearyl group | 15 | 85 | — |
| 30 | 100,000 | n-Stearylamine | 15 | 60 | DAP | 102 | 40 | CK | 102 | n-Stearyl group | 15 | 85 | — |
| 31 | 56,000 | n-Oleylamine | 15 | 60 | DAP | 102 | 40 | CK | 102 | Oleyl group | 15 | 85 | — |
| 32 | 55,000 | n-Stearylamine n-Propylamine | 15 10 | 60 40 | DAP | 90 | 40 | CNa | 90 | n-Stearyl group n-Propyl group | 15 10 | 75 | — |
| 33 | 55,000 | n-Stearylamine Hexylamine | 15 10 | 60 40 | DAP | 90 | 40 | CK | 90 | n-Stearyl group Hexyl group | 15 10 | 75 | — |
| 34 | 55,000 | n-Stearylamine | 20 | 60 | DAP | 96 | 40 | CK | 40 | n-Stearyl group | 20 | 40 | Dimethylaminopropyl group 80 |
| 35 | 56,000 | n-Stearylamine Hexylamine Ethanolamine | 20 10 20 | 60 40 40 | DAP | 60 | 40 | CK | 60 | n-Stearyl group Hexyl group Ethanol group | 20 10 20 | 50 | |
| 36 | 10,000 | n-Stearylamine Ethanolamine | 25 25 | 60 40 | DAP | 60 | 40 | CK | 60 | n-Stearyl group Ethanol group | 25 25 | 50 | — |

*[1]DAP, Dimethylaminopropylamine (N,N-Dimethyl-1,3-propanediamine);
*[2]CK, Potassium chloroacetate; CNa, Sodium chloroacetate.

TABLE 3

| | | Reaction | | | | | | | | Products Composition (mol %) | | |
|---|---|---|---|---|---|---|---|---|---|---|---|---|
| | | Hydrophobic amines | | | | Amines *1 | | | Amphoterizing agent*2 | | | |
| Ex. | PSI | Type | mol % /PSI | temp °C. | Type | mol % /PSI | temp °C. | Type | mol % /PSI | Hydrophobic group | Amphoteric | Others *3 |
| 37 | 80,000 | n-Stearylamine Ethanolamine | 25 25 | 60 40 | DAP | 60 | 40 | CK | 60 | n-Stearyl group 25 Ethanol group 25 | 50 | — |
| 38 | 55,000 | n-Stearylamine Glycinemethyl amine | 25 25 | 60 40 | DAP | 60 | 40 | CK | 60 | n-Stearyl group 25 Glycinemethyl ester residue 25 | 50 | — |
| 39 | 80,000 | n-Stearylamine N-Aminomethyl ethanol amine | 25 25 | 60 40 | DAP | 60 | 40 | CK | 60 | n-Stearyl group 25 N-Aminomethyl ethanol group 25 | 50 | — |
| 40 | 55,000 | n-Stearylamine 2-(2-Aminoethoxy)ethanol | 25 25 | 60 40 | DAP | 60 | 40 | CK | 60 | n-Stearylgroup 25 2-(2-Aminoethoxy) ethanol group 25 | 50 | — |
| 41 | 55,000 | Oleylamine | 25 | 60 | DAP | 90 | 40 | CK | 90 | Oleyl group 25 | 75 | — |
| 42 | 55,000 | Oleylamine n-Laurylamine | 25 10 | 60 60 | DAP | 78 | 40 | CK | 78 | Oleyl group 25 n-Lauryl group 10 | 65 | — |
| 43 | 77,000 | n-Stearylamine | 30 | 60 | DAP | 84 | 40 | CK | 84 | n-Stearyl group 30 | 70 | — |
| 44 | 55,000 | n-Stearylamine | 30 | 60 | DAP | 84 | 40 | CK | 30 | n-Stearyl group 30 | 40 | Dimethylamino propyl group 30 |
| 45 | 55,000 | Oleylamine | 40 | 60 | DAP | 84 | 40 | CK | 30 | Oleyl group 40 | 30 | Dimethylamino propyl group 30 |

*¹DAP, Dimethylaminopropylamine (N,N-Dimethyl-1,3-propanediamine).
*²CK, Potassium chloroacetate.

TABLE 4

| | Composition (mol %) | | | | Solubility | | Curl retention (%) | Evaluation of function | | | | Overall evaluation |
|---|---|---|---|---|---|---|---|---|---|---|---|---|
| Com Ex. | Hydrophobic group | | Others*¹ | | Ethanol | Ethanol /water | | Flaking | Feel | Gloss | Orderliness | |
| 1 | n-Lauryl group | 25 | Pasp-Na | 80 | × | Δ | 43 | × | × | ○ | ○ | × |
| 2 | Cysteamine resisdue | 25 | Pasp-Na | 80 | × | Δ | 28 | × | × | Δ | Δ | × |
| 3 | — | | Dimethylaminopropyl group | 100 | ○ | ○ | 32 | ○ | × | × | × | × |
| 4 | — | | Pasp-Na | 100 | × | × | 15 | ○ | × | × | × | × |
| 5 | n-Lauryl group | 25 | Dimethylaminopropyl group | 75 | × | ○ | 21 | Δ | × | ○ | ○ | × |

*¹Pasp-Na, sodium salt of polyaspartic acid.

TABLE 5

| | Composition (mol %) | | | | | Solubility | | Curl retention (%) | Evaluation of function | | | | Overall evaluation |
|---|---|---|---|---|---|---|---|---|---|---|---|---|---|
| Ex. | Hydrophobic group | | Amphoteric | Others*¹ | | Ethanol | Ethanol /water | | Flaking | Feel | Gloss | Orderliness | |
| 1 | n-Lauryl group | 25 | 75 | — | | ○ | ○ | 65 | ○ | ○ | Δ | ○ | ○ |
| 2 | n-Lauryl group | 50 | 50 | — | | Δ | Δ | 50 | Δ | ○ | ○ | ○ | □ |
| 3 | n-Lauryl group | 50 | 50 | — | | × | Δ | 60 | Δ | ○ | ○ | ○ | Δ |
| 4 | n-Stearyl group | 17 | 83 | — | | Δ | ○ | 78 | ○ | ○ | ○ | ○ | ○ |
| 5 | n-Stearyl group | 25 | 75 | — | | Δ | ○ | 80 | ○ | ○ | ○ | ○ | ○ |
| 6 | — | | 50 | PSI 50 | | × | ○ | 11 | Δ | Δ | Δ | Δ | Δ |
| 7 | — | | 100 | — | | × | ○ | 19 | ○ | Δ | Δ | ○ | Δ |
| 8 | Diethyl group | 25 | 75 | — | | × | ○ | 18 | ○ | Δ | Δ | Δ | Δ |
| 9 | Ethanol group | 25 | 75 | — | | ○ | ○ | 30 | ○ | Δ | Δ | Δ | □ |
| 10 | Diethanol group | 25 | 75 | — | | ○ | ○ | 31 | ○ | × | Δ | Δ | Δ |
| 11 | n-Propyl group | 70 | 75 | — | | ○ | ○ | 60 | ○ | ○ | Δ | ○ | ○ |
| 12 | Isopropyl group | 50 | 50 | — | | ○ | × | 55 | Δ | Δ | Δ | ○ | Δ |
| 13 | Cyclohexyl group | 25 | 75 | — | | × | ○ | 48 | ○ | ○ | Δ | ○ | Δ |

TABLE 5-continued

| | Composition (mol %) | | | Solubility | | Curl reten- | Evaluation of function | | | | Over-all |
|---|---|---|---|---|---|---|---|---|---|---|---|
| Ex. | Hydrophobic group | Ampho-teric | Others*[1] | Ethanol | Ethanol /water | tion (%) | Flak-ing | Feel | Gloss | Order-liness | evalu-ation |
| 14 | sec-Butyl group | 60 | 5 | PSI 35 | ○ | × | 56 | Δ | Δ | Δ | Δ | Δ |
| 15 | tert-Butyl group | 16 | 84 | — | × | ○ | 47 | ○ | Δ | Δ | ○ | Δ |

*[1]PSI, Polysuccinimide.

TABLE 6

| | Composition (mol %) | | | Solubility | | Curl reten- | Evaluation of function | | | | Over-all |
|---|---|---|---|---|---|---|---|---|---|---|---|
| Ex. | Hydrophobic group | Ampho-teric | Others | Ethanol | Ethanol /water | tion (%) | Flak-ing | Feel | Gloss | Order-liness | evalu-ation |
| 16 | n-Butyl group | 25 | 75 | — | ○ | ○ | 41 | ○ | Δ | Δ | ○ | ○ |
| 17 | n-Butyl group | 70 | 30 | — | × | ○ | 52 | ○ | Δ | Δ | ○ | Δ |
| 18 | 3-(2-Ethylhexyloxy)plopyl group | 25 | 75 | — | ○ | ○ | 42 | ○ | Δ | Δ | ○ | ○ |
| 19 | Hexyl group | 25 | 75 | — | ○ | ○ | 45 | ○ | Δ | Δ | ○ | ○ |
| 20 | Hexyl group | 75 | 5 | — | ○ | Δ | 99 | Δ | ○ | ○ | ○ | ○ |
| 21 | Octyl group | 25 | 75 | — | ○ | ○ | 70 | ○ | ○ | ○ | ○ | ◎ |
| 22 | n-Lauryl group | 25 | 5 | Dimethylamino propyl group 70 | ○ | × | 40 | Δ | ○ | ○ | ○ | Δ |
| 23 | n-Lauryl group | 25 | 75 | — | Δ | ○ | 66 | ○ | ○ | ○ | ○ | ○ |
| 24 | n-Lauryl group | 25 | 75 | — | ○ | ○ | 68 | ○ | ○ | ○ | ○ | ◎ |
| 25 | n-Lauryl group | 40 | 50 | Dimethylamino propyl group 10 | × | ○ | 82 | Δ | Δ | ○ | ○ | Δ |
| 26 | n-Lauryl group / Hexyl group | 50 / 20 | 30 | — | ○ | ○ | 84 | Δ | ○ | ○ | ○ | ○ |
| 27 | n-Stearyl group / n-Lauryl group | 10 / 25 | 65 | — | Δ | ○ | 60 | ○ | ○ | ○ | ○ | ○ |
| 28 | n-Stearyl group | 15 | 5 | Dimethylamino propyl group 80 | ○ | ○ | 72 | ○ | ○ | ○ | ○ | ◎ |
| 29 | n-Stearyl group | 15 | 85 | — | ○ | ○ | 59 | ○ | ○ | ○ | ○ | ○ |
| 30 | n-Stearyl group | 15 | 85 | — | Δ | ○ | 72 | ○ | ○ | ○ | ○ | ○ |
| 31 | Oleyl group | 15 | 85 | — | ○ | ○ | 89 | ○ | ○ | ○ | ○ | ◎ |
| 32 | n-Stearyl group / n-Propyl group | 15 / 10 | 75 | — | ○ | ○ | 88 | ○ | ○ | ○ | ○ | ◎ |
| 33 | n-Stearyl group / Hexyl group | 15 / 10 | 75 | — | ○ | ○ | 92 | ○ | ○ | ○ | ○ | ◎ |

TABLE 7

| | Composition (mol %) | | | Solubility | | Curl reten- | Evaluation of function | | | | Over-all |
|---|---|---|---|---|---|---|---|---|---|---|---|
| Ex. | Hydrophobic group | Ampho-teric | Others | Ethanol | Ethanol /water | tion (%) | Flak-ing | Feel | Gloss | Order-liness | evalu-ation |
| 34 | n-Stearyl group | 20 | 40 | Dimethylamino propyl group 40 | ○ | × | 90 | ○ | ○ | ◎ | ○ | Δ |
| 35 | n-Stearyl group / Hexyl group / Ethanol group | 20 / 10 / 20 | 50 | — | × | ○ | 52 | ○ | ○ | ◎ | ○ | Δ |
| 36 | n-Stearyl group / Ethanol group | 25 / 25 | 50 | — | × | Δ | 85 | Δ | Δ | ◎ | Δ | Δ |
| 37 | n-Stearyl group / Ethanol group | 25 / 25 | 50 | — | Δ | Δ | 92 | Δ | ○ | ◎ | ○ | □ |

TABLE 7-continued

| Ex. | Composition (mol %) Hydrophobic group | | Amphoteric | Others | Solubility Ethanol | Ethanol /water | Curl retention (%) | Evaluation of function Flaking | | Feel | Gloss | Orderliness | Overall evaluation |
|---|---|---|---|---|---|---|---|---|---|---|---|---|---|
| 38 | n-Stearyl group Glycinemethyl ester residue | 25 25 | 50 | — | × | ○ | 96 | ○ | ○ | ◎ | ○ | △ |
| 39 | n-Stearyl group N-Aminomethyl ethanol group | 25 25 | 50 | — | △ | △ | 92 | △ | ○ | ◎ | ○ | □ |
| 40 | n-Stearyl group 2-(2-Aminoethoxy) ethanol group | 25 25 | 50 | — | × | ○ | 97 | ○ | ○ | ◎ | ○ | △ |
| 41 | Oleyl group | 25 | 75 | — | ○ | ○ | 94 | ○ | ○ | ◎ | ○ | ◎ |
| 42 | Oleyl group n-Lauryl group | 25 10 | 65 | — | ○ | ○ | 99 | ○ | ○ | ◎ | ○ | ◎ |
| 43 | n-Stearyl group | 30 | 70 | — | △ | △ | 99 | △ | ○ | ◎ | ○ | □ |
| 44 | n-Stearyl group | 30 | 40 | Dimethylamino propyl group 30 | ○ | × | 95 | △ | ○ | ◎ | ○ | △ |
| 45 | Oleyl group | 40 | 30 | Dimethylamino propyl group 30 | × | △ | 71 | △ | ○ | ◎ | ○ | △ |

[2] Examples Concerning Application to Gel-like Hair dressing Compositions

The application of polyaspartic acid derivatives in accordance with the present invention to gel-like hairdressing compositions is explained with reference to the following examples.

[Preparation Example 2-1]

(Preparation of polyaspartic acid derivative BL25)

A separable flask fitted with a stirrer, a heater, a thermometer and a nitrogen line was used as a reactor and the reaction system was fully stirred during the reaction. As the starting material, there was used PSI (having a Mw of 81,000 as measured by GPC in a DMF system) which had been fully dried by heating to 60° C. under reduced pressure. 15 g (0.154 mol) of this PSI was dissolved in 100 g of DMF at room temperature, and 7.14 g (0.0386 mol; 25 mol % based on the imide ring of PSI) of n-laurylamine was added thereto. The DMF used as the reaction solvent had been dried with molecular sieves and by blowing dry nitrogen gas thereinto, and the water content in the reaction system was kept at 800 ppm or less during the reaction. The reaction was carried out for 4 hours with the internal temperature of the reactor maintained at 60° C. After completion of the reaction, the reactor was cooled. When the internal temperature was 40° C. or below, N,N-dimethyl-1,3-propanediamine was added dropwise in an amount corresponding to the remaining molar amount of the imide ring of PSI and the reaction was continued at room temperature for another 4 hours.

The above reaction mixture was poured into 800 ml of an acetone/hexane (5:2) solvent mixture to form a precipitate. This precipitate was recovered by suction filtration and further washed with the aforesaid solvent mixture several times. 15 g of the isolated polymer powder was dissolved in 100 ml of ethanol at room temperature and charged into the reactor. Then, 100 ml of an ethanolic solution of potassium monochloroacetate containing potassium monochloroacetate in an amount 10% greater than the molar amount of N,N-dimethyl-1,3-propanediamine added as above was added dropwise to the flask through a dropping funnel. After completion of the addition, the resulting mixture was reacted for another 10 hours under reflux in a stream of nitrogen. After completion of the reaction, the reaction mixture was concentrated to about 70 ml and filtered under pressure to remove the precipitate (i.e., inorganic salts).

The above reaction mixture was poured into 700 ml of an acetone/hexane (5:2) solvent mixture to form a precipitate. This precipitate was recovered by suction filtration, washed several times with the aforesaid solvent mixture, and vacuum-dried to obtain a white polymer powder. Its yield was 93%.

It was confirmed by NMR analysis that the resulting polymer was a polyaspartic acid derivative having about 75 mol % of a betaine structure and about 25 mol % of lauryl group. This polymer will hereinafter be abbreviated as BL25.

[Preparation Example 2-2]

(Preparation of polyaspartic acid derivative BL40)

A polyaspartic acid derivative having about 60 mol % of a betaine structure and about 40 mol % of lauryl group was prepared in the same manner as in Preparation Example 2-1, except that n-laurylamine was used in an amount of 40 mol % based on the imide ring of PSI. This polymer will hereinafter be abbreviated as BL40.

[Preparation Example 2-3]

(Preparation of polyaspartic acid derivative BS20)

A polyaspartic acid derivative having about 80 mol % of a betaine structure and about 20 mol % of stearyl group was prepared in the same manner as in Preparation Example 2-1, except that, in place of n-laurylamine, stearylamine was used in an amount of 20 mol % based on the imide ring of PSI. This polymer will hereinafter be abbreviated as BS20.

[Preparation Example 2-4]

(Preparation of polyaspartic acid derivative BT)

A polyaspartic acid derivative having 100 mol % of a betaine structure was prepared in the same manner as in Preparation Example 2-1, except that the step of reaction with n-laurylamine was omitted and N,N-dimethyl-1,3-propanediamine was used in an amount of 105% based on the imide ring of PSI. This polymer will hereinafter be abbreviated as BT.

[Example 2-1]

5 g of polyaspartic acid derivative BL25 obtained in Preparation Example 2-1 was dissolved in a purified water/ethanol (1:1) solvent mixture so as to give a concentration of 10%. On the other hand, 0.5 g of commercially available Carbopol 940 (trade name of a product of Goodrich Co.) as a gel-forming base material was dissolved in 47.7 g of purified water, and 1.8 g of a 10% aqueous solution of sodium hydroxide as a base was added thereto, followed by stirring. Then, the above water/ethanol solution of the polyaspartic acid derivative was added thereto and the resulting mixture was stirred well to obtain a gel-like hairdressing composition.

[Example 2-2]

3 g of polyaspartic acid derivative BL40 obtained in Preparation Example 2-2 was dissolved in a purified water/ethanol (1:1) solvent mixture so as to give a concentration of 10%. On the other hand, 2.0 g of the aforesaid Carbopol as a gel-forming base material was dissolved in 60.8 g of purified water, and 7.2 g of a 10% aqueous solution of sodium hydroxide as a base was added thereto, followed by stirring. Then, the above water/ethanol solution of the polyaspartic acid derivative was added thereto and the resulting mixture was stirred well to obtain a gel-like hairdressing composition.

[Example 2-3]

1 g of polyaspartic acid derivative BS20 obtained in Preparation Example 2-3 was dissolved in a purified water/ethanol (1:1) solvent mixture so as to give a concentration of 10%. On the other hand, 0.5 g of the aforesaid Carbopol as a gel-forming base material was dissolved in 87.7 g of purified water, and 1.8 g of a 10% aqueous solution of sodium hydroxide as a base was added thereto, followed by stirring. Then, the above water/ethanol solution of the polyaspartic acid derivative was added thereto and the resulting mixture was stirred well to obtain a gel-like hairdressing composition.

[Example 2-4]

10 g of polyaspartic acid derivative BT obtained in Preparation Example 2-4 was dissolved in purified water so as to give a concentration of 20%. On the other hand, 0.5 g of the aforesaid Carbopol as a gel-forming base material was dissolved in 47.7 g of purified water, and 1.8 g of a 10% aqueous solution of sodium hydroxide as a base was added thereto, followed by stirring. Then, the above aqueous solution of the polyaspartic acid derivative was added thereto and the resulting mixture was stirred well to obtain a gel-like hairdressing composition.

[Comparative Example 2-1]

0.5 g of the aforesaid Carbopol as a gel-forming base material was dissolved in 47.7 g of purified water, and 1.8 g of a 10% aqueous solution of sodium hydroxide as a base was added thereto, followed by stirring. Then, 50 g of a water/ethanol (1:1) solvent mixture was added thereto and the resulting mixture was stirred well to obtain a gel-like hairdressing composition.

[Comparative Example 2-2]

0.5 g of the aforesaid Carbopol as a gel-forming base material was dissolved in 90.7 g of purified water, and 1.8 g of a 10% aqueous solution of sodium hydroxide as a base was added thereto, followed by stirring. Then, 7 g of commercially available Diahold (trade name of a product of Mitsubishi Chemical Co., Ltd.; a 50% ethanolic solution of an acrylic polymer) as an anionic resin for use in hairdressings was added thereto and the resulting mixture was stirred well to obtain a hairdressing composition.

[Comparative Example 2-3]

5.0 g of powdered polyvinyl pyrrolidone as a nonionic resin for use in hairdressings was dissolved in purified water so as to give a concentration of 20%. On the other hand, 0.5 g of the aforesaid Carbopol as a gel-forming base material was dissolved in 47.7 g of water, and 1.8 g of a 10% aqueous solution of sodium hydroxide as a base was added thereto, followed by stirring. Then, the above aqueous solution of polyvinyl pyrrolidone was added thereto and the resulting mixture was stirred well to obtain a hairdressing composition.

[Comparative Example 2-4]

0.5 g of commercially available Carbopol 940 (trade name of a product of Goodrich Co.) as a gel-forming base material was dissolved in 87.7 g of purified water, and 1.8 g of a 10% aqueous solution of sodium hydroxide as a base was added thereto, followed by stirring. Then, 10 g of commercially available MERQUAT (trade name of a product of Merck & Co., Inc.; a 40% aqueous solution of a polymer of diallyldimethylammonium chloride) as a resin for use in cationic hairdressing agents was added thereto and the resulting mixture was stirred well to obtain a hairdressing composition.

The hairdressing compositions of Examples 2-1 to 2-4 and Comparative Examples 2-1 to 2-4 were evaluated according to the previously described procedures and the results thus obtained are shown in Tables 8 and 9.

As to curl retention, the following rating system was employed.

o, the degree of curl retention was 70% or greater;

Δ, the degree of curl retention was from 50% to less than 70%;

X, the degree of curl retention was less than 50%.

As to gel transparency, each hairdressing composition was placed in a glass bottle, and its transparency was examined by visual observation and rated as follows:

o, highly transparent;

Δ, slightly cloudy;

X, turbid.

TABLE 8

Examples 2-1 to 2-4

| Example | | | 2-1 | 2-2 | 2-3 | 2-4 |
|---|---|---|---|---|---|---|
| Composition | (A) | Polyaspartic acid derivative (g) | BL25 (5.0) | BL40 (3.0) | BS20 (1.0) | BT (10.0) |
| | (B) | Gel-forming base material (g) | Carbopol (0.5) | Carbopol (0.5) | Carbopol (2.0) | Carbopol (0.5) |
| | (C) | Solvent Purified (g) water | 70.2 | 74.3 | 92.2 | 87.7 |
| | | Ethanol | 22.5 | 13.5 | 4.5 | 0.0 |
| | Aqueous solution of sodium hydroxide (g) | | 1.8 | 7.2 | 1.8 | 1.8 |
| Results | Gel transparency | | ○ | ○ | Δ | ○ |
| | Curl retention | | ○ | ○ | ○ | Δ |
| | Flaking | | ○ | ○ | ○ | ○ |
| | Gloss | | ○ | ○ | ○ | ○ |
| Overall evaluation | | | ○ | ○ | ○ | ○ |

[Notes] Carbopol, Carbopoly 940 (manufactured by Goodrich Co.).

TABLE 9

| Comparative Example | | | 2-1 | 2-2 | 2-3 | 2-4 |
|---|---|---|---|---|---|---|
| Composition | (A) | Polyaspartic acid derivative (g) | — (0.0) | HR-200 (7.0) | PVPK-30 (5.0) | MERQUAT (10.0) |
| | (B) | Gel-forming base material (g) | Carbopol (0.5) | Carbopol (0.5) | Carbopol (0.5) | Carbopol (0.5) |
| | (C) | Solvent Purified (g) water | 72.7 | 90.7 | 92.7 | 87.7 |
| | | Ethanol | 25.0 | 0.0 | 0.0 | 0.0 |
| | Aqueous solution of sodium hydroxide (g) | | 1.8 | 1.8 | 1.8 | 1.8 |
| Results | Gel transparency | | ○ | × | ○ | × |
| | Curl retention | | × | Δ | × | × |
| | Flaking | | Δ | Δ | × | ○ |
| | Gloss | | × | × | × | × |
| Overall evaluation | | | × | × | × | × |

[Notes] Carbopol, Carbopol 940 (manufactured by Goodrich Co.); HR-200, Diahold HR-200; MERQUAT, MERQUAT 100.

[3] Examples Concerning Application to Humectant Compositions

The application of polyaspartic acid derivatives in accordance with the present invention to humectant compositions is explained with reference to the following examples.

[Preparation Example 3-1]

30 g of PSI having a Mw of 80,000 was dissolved in 100 g of DMF at room temperature, and 15 g of n-dodecylamine was added dropwise thereto. The resulting mixture was reacted at 60° C. for 5 hours with stirring. After completion of the reaction, 24 g of N,N-dimethyl-1,3-propanediamine was added dropwise thereto and the reaction was continued at room temperature for another 5 hours. The reaction mixture was poured into 500 ml of stirred acetone. The product was filtered off, washed and dried to obtain 63 g of a polymer. Then, 60 g of this polymer was dissolved in 400 ml of ethanol, and 400 ml of an ethanolic solution containing 32 g of potassium monochloroacetate was added dropwise thereto. The resulting mixture was reacted for 6 hours under reflux in a stream of nitrogen. After completion of the reaction, the reaction mixture was concentrated to about 300 ml and filtered to remove the precipitate. The filtrate was poured into 3 liters of a stirred acetone/hexane (8:2) solvent mixture. The product was filtered off, washed and dried to obtain 70 g of a polyaspartic acid derivative having amphoteric ions in a 92% yield.

[Preparation Example 3-2]

The procedure of Preparation Example 3-1 was repeated, except that 15 g of n-octadecylamine was used in place of n-dodecylamine. Thus, 65 g of a polyaspartic acid derivative having amphoteric ions was obtained in a 88% yield.

[Preparation Example 3-3]

The procedure of Preparation Example 3-1 was repeated, except that 20 g of N,N-dimethyl-1,2-ethanediamine was used in place of N,N-dimethyl-1,3-propanediamine. Thus, 68 g of a polyaspartic acid derivative having amphoteric ions was obtained in a 88% yield.

[Example 3-1]

A toilet lotion was prepared from 1.0% by weight of the polyaspartic acid derivative obtained in Preparation Example 3-1, 2.0% by weight of polyoxyethylene (20 moles added) sorbitan monolaurate, 1.0% by weight of polyoxyethylene (20 moles added) lauryl ether sulfate sodium, 8.0% by weight of ethanol, 5.0% by weight of glycerin, 4.0% by weight of propylene glycol, 0.2% by weight of citric acid and the balance purified water.

[Example 3-2]

A milky lotion was prepared from 2.0% by weight of the polyaspartic acid derivative obtained in Preparation Example 3-1, 2.0% by weight of polyoxyethylene (20 moles added) hardened castor oil, 1.0% by weight of coconut oil fatty acid monoglyceride, 7.0% by weight of oleic acid triglyceride, 3.0% by weight of glycerin, appropriate amounts of perfume and antiseptic, and the balance purified water.

[Example 3-3]

A hand cream was prepared from 3.0% by weight of the polyaspartic acid derivative obtained in Preparation Example 3-2, 20.0% by weight of vaseline, 7.0% by weight of cetanol, 1.0% by weight of polyoxyethylene (20 moles added) lauryl ether sulfate sodium, 1.0% by weight of sorbitan monostearate, appropriate amounts of perfume and antiseptic, and the balance purified water.

[Example 3-4]

A cleansing gel was prepared from 1.0% by weight of the polyaspartic acid derivative obtained in Preparation Example 3-3, 2.0% by weight of polyoxyethylene (15 moles added) nonyl phenyl ether, 0.5% by weight of triethanolamine, 0.5% by weight of methylparaben, 40.0% by weight of ethanol and the balance purified water.

[Comparative Example 3-1]

A toilet lotion was prepared in the same manner as described in Example 3-1, except that the polyaspartic acid derivative was not added.

[Comparative Example 3-2]

A milky lotion was prepared in the same manner as described in Example 3-2, except that the polyaspartic acid derivative was not added.

[Comparative Example 3-3]

A hand cream was prepared in the same manner as described in Example 3-3, except that 3.0% by weight of sodium polyaspartate was added in place of the polyaspartic acid derivative.

The humectant compositions of Examples 3-1 to 3-4 and Comparative Examples 3-1 to 3-3 were subjected to the following organoleptic test, and the results thus obtained are shown in Table 10.

(Organoleptic test)

The smoothness, moistness and stickiness of the skin to which each composition was applied was evaluated by 20 panel members. Each parameter was scored on the following three-grade basis and the average of the scores was calculated.

(1) Smoothness 3, very smooth; 2, rather smooth; 1, not smooth.

(2) Moistness 3, excellently moist; 2, ordinarily moist; 1, not moist.

(3) Stickiness 3, not sticky; 2, slightly sticky; 1, very sticky.

TABLE 10

Results of Evaluation in Examples 3-1 to 3-4 and Comparative Examples 3-1 to 3-3

| | Smoothness | Moistness | Stickiness |
|---|---|---|---|
| Example 3-1 | 2.5 | 2.7 | 2.8 |
| Comparative Example 3-1 | 2.1 | 1.8 | 2.8 |
| Example 3-2 | 2.6 | 2.8 | 2.8 |
| Comparative Example 3-2 | 2.0 | 2.0 | 2.7 |
| Example 3-3 | 2.6 | 2.8 | 2.7 |
| Comparative Example 3-3 | 2.4 | 2.3 | 2.5 |
| Example 3-4 | 2.8 | 2.8 | 2.7 |

[4] Examples Concerning Application to Cleansing Compositions

The application of polyaspartic acid derivatives in accordance with the present invention to cleansing compositions is explained with reference to the following examples.

[Preparation Example 4-1]

15 g of PSI having a Mw of 80,000 was dissolved in 50 g of DMF at room temperature, and 7.2 g of n-dodecylamine was added dropwise thereto. The resulting mixture was reacted at 60° C. for 4 hours with stirring. After completion of the reaction, 12 g of N,N-dimethyl-1,3-propanediamine was added dropwise thereto and the reaction was continued at room temperature for another 4 hours. The reaction mixture was poured into 200 ml of stirred acetone. The product was filtered off, washed and dried to obtain 31 g of a polymer. Then, 15 g of this polymer was dissolved in 100 ml of ethanol, and 100 ml of an ethanolic solution containing 8.1 g of potassium monochloroacetate was added dropwise thereto. The resulting mixture was reacted for 6 hours under reflux in a stream of nitrogen. After completion of the reaction, the reaction mixture was concentrated to about 70 ml and filtered to remove the precipitate. The filtrate was poured into 700 ml of a stirred acetone/hexane (8:2) solvent mixture. The product was filtered off, washed and dried to obtain 17 g of a polyaspartic acid derivative having amphoteric ions in a 90% yield.

[Preparation Example 4-2]

The procedure of Preparation Example 4-1 was repeated, except that 7.1 g of n-octadecylamine was used in place of n-dodecylamine. Thus, 18 g of a polyaspartic acid derivative having amphoteric ions was obtained in a 94% yield.

[Preparation Example 4-3]

The procedure of Preparation Example 4-1 was repeated, except that 10 g of N,N-dimethyl-1,2-ethanediamine was used in place of N,N-dimethyl-1,3-propanediamine. Thus, 17 g of a polyaspartic acid derivative having amphoteric ions was obtained in a 88% yield.

[Example 4-1]

A shampoo composition was prepared from 2.0% by weight of the polyaspartic acid derivative obtained in Preparation Example 4-1, 8.0% by weight of polyoxyethylene (20 moles added) lauryl ether sulfate sodium, 3.0% by weight of triethanolamine myristate, 2.0% by weight of coconut oil fatty acid diethanolamide, 5.0% by weight of glycerin, 1.0% by weight of diethylene glycol distearate, appropriate amounts of perfume and antiseptic, and the balance purified water.

[Example 4-2]

A body shampoo was prepared from 5.0% by weight of the polyaspartic acid derivative obtained in Preparation Example 4-1, 4.0% by weight of polyoxyethylene (20 moles added) lauryl ether sulfate sodium salt, 8.0% by weight of N-cocoylmethyltaurine sodium salt, 5.0% by weight of triethanolamine laurate, 5.0% by weight of coconut oil fatty acid diethanolamide, 3.0% by weight of glycerin, appropriate amounts of pigment and antiseptic, and the balance purified water.

[Example 4-3]

A face-washing foam was prepared from 3.0% by weight of the polyaspartic acid derivative obtained in Preparation Example 4-2, 8.0% by weight of sodium N-myristoylglutamate, 10.0% by weight of sodium monomyristylphosphate, 8.0% by weight of myristic acid, 6.0% by weight of stearic acid, 4.0% by weight of potassium hydroxide, 3.0% by weight of lauric acid diethanolamide, 10.0% by weight of glycerin, appropriate amounts of perfume and antiseptic, and the balance purified water.

[Example 4-4]

A kitchen cleaner was prepared from 5.0% by weight of the polyaspartic acid derivative obtained in Preparation Example 4-3, 15.0% by weight of polyoxyethylene (20 moles added) lauryl ether sulfate sodium salt, 4.0% by weight of coconut oil fatty acid diethanolamide, 0.1% by weight of methylparaben, appropriate amounts of perfume and antiseptic, and the balance purified water.

[Comparative Example 4-1]

A shampoo composition was prepared in the same manner as described in Example 4-1, except that the polyaspartic acid derivative was not used and polyoxyethylene lauryl ether sulfate sodium salt was added in an amount of 10.0% by weight.

[Comparative Example 4-2]

A body shampoo was prepared in the same manner as described in Example 4-2, except that the polyaspartic acid derivative was not used and polyoxyethylene lauryl ether sulfate sodium salt added was added in an amount of 9.0% by weight.

[Comparative Example 4-3]

A face-washing foam was prepared in the same manner as described in Example 4-3, except that the polyaspartic acid derivative was not added.

[Comparative Example 4-4]

A kitchen cleaner was prepared in the same manner as described in Example 4-4, except that the polyaspartic acid derivative was not added.

The cleansing compositions of Examples 4-1 to 4-4 and Comparative Examples 4-1 to 4-4 were evaluated according to the following procedures, and the results thus obtained are shown in Table 11.

(1) Irritation to the skin

According to Draze's method (OECD Guideline, No. 404), each composition was tested with 3 white rabbits. A solution having an active ingredient concentration of 5% by weight was applied to the rabbits. After a predetermined period of time, the skin was observed and scored. This Draze score was rated according to the following four-grade system.

⊙, minimal;
o, mild;
Δ, moderate;
X, severe.

(2) Dispersibility

After each composition was allowed to stand at 25° C. for one month, its appearance was observed and rated as follows:

o, the composition remained uniformly dispersed;
Δ, a small amount of precipitate was produced;
X, a large amount of precipitate was produced.

(3) Quality of foam 20 ml of an aqueous solution of each composition having an active ingredient concentration of 3% by weight was placed in a 50 ml sample bottle with a stopper. After the bottle was tightly stoppered and vigorously shaken 20 times, the resulting foam was observed and rated as follows:

o, the foam was fine and creamy;
Δ, the fineness of the foam was moderate;
X, the fineness of the foam was poor.

(4) Feel 1.0 g of each composition was taken in hands and washed off with water. Its feel was rated as follows:

o, very smooth;
Δ, somewhat less smooth;
X, not smooth.

TABLE 11

Results of Evaluation in Examples 4-1 to 4-4 and Comparative Examples 4-1 to 4-4

|  | Irritation to the skin | Dispersibility | Quality of foam | Feel |
| --- | --- | --- | --- | --- |
| Example 4-1 | ⊙ | o | o | o |
| Example 4-2 | ⊙ | o | o | o |
| Example 4-3 | ⊙ | o | o | o |
| Example 4-4 | ⊙ | o | o | o |
| Comparative Example 4-1 | o | Δ | Δ | Δ |
| Comparative Example 4-2 | o | Δ | Δ | X |
| Comparative Example 4-3 | o | o | o | Δ |
| Comparative Example 4-4 | Δ | o | Δ | X |

[5] Examples Concerning Application to Hairdressing Spray Compositions

The application of polyaspartic acid derivatives in accordance with the present invention to hairdressing spray compositions is explained with reference to the following examples.

[Preparation Example 5-1]

(Preparation of polyaspartic acid derivative BL25)

BL25 was obtained in the same manner as described in Preparation Example 2-1. Then, the resulting white powder of BL25 was dissolved in a purified water/ethanol (3:7) solvent mixture so as to give a concentration of 30%. Thus, there was obtained a solution of BL25.

[Preparation Example 5-2]

(Preparation of polyaspartic acid derivative BL40)

BL40 was obtained in the same manner as described in Preparation Example 2-2. Then, a solution of BL40 (in ethanol) was obtained in the same manner as described in Preparation Example 5-1.

[Preparation Example 5-3]

(Preparation of polyaspartic acid derivative BS20)

BS20 was obtained in the same manner as described in Preparation Example 2-3. Then, a solution of BS20 [in purified water/ethanol (3:7)] was obtained in the same manner as described in Preparation Example 5-1.

[Preparation Example 5-4]

(Preparation of polyaspartic acid derivative BS15/L10)

The procedure of Preparation Example 5-1 was repeated, except that, in place of n-laurylamine, stearylamine was first reacted in an amount of 15 mol % based on the imide ring of PSI and laurylamine was then reacted in an amount of 10 mol % based on the imide ring of PSI. Thus, a polyaspartic acid derivative having about 75 mol % of betaine, about 15 mol % of stearyl group and about 10 mol % of lauryl group was prepared. This polymer will hereinafter be abbreviated as BS15/L10. Then, a solution of BS15/L10 (in ethanol) was obtained in the same manner as described in Preparation Example 5-1.

[Preparation Example 5-5]

(Preparation of polyaspartic acid derivative BT)

BT was obtained in the same manner as described in Preparation Example 2-4. Then, a solution of BT [in purified water/ethanol (3:7)] was obtained in the same manner as described in Preparation Example 5-1.

[Example 5-1]

50 g of the solution of polyaspartic acid derivative BL25 obtained in Preparation Example 5-1 and 22 g of dehydrated ethanol were placed in a pressure spray bottle made of glass. Then, 20 g of a propellant comprising a mixture of propane, n-butane and isobutane in a weight ratio of 20:50:30 was charged into the spray bottle under pressure to obtain a spray sample.

[Examples 5-2 to 5-5]

Spray samples were obtained in the same manner as described in Example 5-1, except that the spray formulation was altered as shown in Table 12.

[Comparative Example 5-1]

A spray sample was obtained in the same manner as described in Example 5-1, except that Gantrez ES-225 (an anionic polymer sold by ISP, U.S.A.; neutralized with aminomethylpropanol by 20% of the theoretical amount and used as an ethanolic solution having an active ingredient concentration of 50%) being a currently used anion type commercial product was used and the spray formulation was altered as shown in Table 12.

[Comparative Example 5-2]

A spray sample was obtained in the same manner as described in Example 5-1, except that Amphomer (an amphoteric ion-containing polymer sold by GAF Corporation, U.S.A.; used after neutralization with aminomethylpropanol by 95% of the theoretical amount) being a currently used amphoteric ion type commercial product was used and the spray formulation was altered as shown in Table 16.

[Comparative Example 5-3]

A spray sample was obtained in the same manner as described in Example 5-1, except that Yukaformer AM-75 (manufactured by Mitsubishi Chemical Co., Ltd.) being a currently used amphoteric ion type commercial product was used and the spray formulation was altered as shown in Table 12.

The hairdressing spray compositions of Examples 5-1 to 5-5 and Comparative Examples 5-1 to 5-3 were evaluated according to the previously described procedures and the following procedures. The results thus obtained are shown in Table 13.

(1) Washability

The aforesaid glass plate was soaked in warm water (40° C.) containing 0.5% by weight of a commercially available shampoo. After one minute, the degree of dissolution of the film was rated as follows:

o, the film was dissolved;
Δ, only the surface of the film was dissolved;
X, the film was not dissolved.

(2) Film smoothness

Each spray sample was sprayed onto a glass plate for 3 seconds. After the glass plate was allowed to stand in an atmosphere having a temperature of 20° C. and a relative humidity (R.H.) of 60% for one day, the resulting film was evaluated by visual inspection and tactile sensation as follows:

o, smooth;
X, not smooth.

(3) Film hardness

The aforesaid glass plate was tested according to JIS 5400 to measure the pencil hardness of the film. The pencil hardness so measured was rated as follows:

o, F or less;
Δ, 2H to H;
X, 3H or greater.

(4) Hair-setting power

After straight hair having a length of 23 cm were washed with a 0.25 wt. % aqueous solution of sodium lauryl sulfate and dried, 2 g samples thereof were bundled. Each bundle of hair was sprayed with a spray sample for 10 seconds, wound around a curler having a diameter of 1.2 cm, and dried. Then, the bundle of hair was suspended in an atmosphere having a temperature of 30° C. and a relative humidity (R.H.) of 90%. After 5 hours, the degree of curl retention (%) was calculated according to the previously described equation and rated as follows:

o, the degree of curl retention was 70% or greater;
Δ, the degree of curl retention was from 50% to less than 70%;
X, the degree of curl retention was less than 50%.

TABLE 12

Examples 5-1 to 5-5 and Comparative Examples 5-1 to 5-3

Spray formulation (wt.%)

| | (A) Amphoteric ion containing resn (as active ingrediet) | | (B) Diluting solvent (ethanol/ water, and ethanol) | (C) Propellant |
|---|---|---|---|---|
| Ex. 5-1 | BL25 | 5 | 55 | 40 |
| Ex. 5-2 | BL40 | 3 | 57 | 40 |
| Ex. 5-3 | BS20 | 3 | 57 | 40 |
| Ex. 5-4 | BS15/L10 | 3 | 57 | 40 |
| Ex. 5-5 | BT | 8 | 52 | 40 |
| Com. Ex. 5-1 | Gantrez | 3 | 57 | 40 |
| Com. Ex. 5-2 | Amphomer | 3 | 57 | 40 |
| Com. Ex. 5-3 | Yukaformer AM-75 | 3 | 57 | 40 |

TABLE 13

Results of Evaluation in Examples 5-1 to 5-5 and Comparative Examples 5-1 to 5-3 Performance

| | Film | | | Hair-setting power | Flaking | Gloss | Feel |
|---|---|---|---|---|---|---|---|
| | Wash-ability | Smooth-ness | Hard-ness | | | | |
| Ex. 5-1 | ○ | ○ | ○ | △ | ○ | ○ | ○ |
| Ex. 5-2 | ○ | ○ | ○ | ○ | ○ | ○ | ○ |
| Ex. 5-3 | ○ | ○ | ○ | ○ | ○ | ○ | ○ |
| Ex. 5-4 | ○ | ○ | ○ | ○ | ○ | ○ | ○ |
| Ex. 5-5 | ○ | ○ | ○ | △ | ○ | △ | ○ |
| Com. Ex. 5-1 | × | ○ | × | ○ | × | △ | × |
| Com. Ex. 5-2 | × | ○ | × | ○ | × | △ | × |
| Com. Ex. 5-3 | × | ○ | △ | ○ | ○ | ○ | △ |

[6] Examples Concerning Application to Hairdressing Resin Compositions

The application of polyaspartic acid derivatives in accordance with the present invention to hairdressing resin compositions is explained with reference to the following examples.

[Preparation Example 6-1]

(Preparation of polyaspartic acid derivative BL25)

BL25 was obtained in the same manner as described in Preparation Example 2-1. Then, the resulting white powder of BL25 was dissolved in a purified water/ethanol (3:7) solvent mixture so as to give a concentration of 30%. Thus, there was obtained a solution of BL25.

[Preparation Example 6-2]

(Preparation of polyaspartic acid derivative BL40)

BL40 was obtained in the same manner as described in Preparation Example 2-2. Then, a solution of BL40 (in ethanol) was obtained in the same manner as described in Preparation Example 6-1.

[Preparation Example 6-3]

(Preparation of polyaspartic acid derivative BS20)

BS20 was obtained in the same manner as described in Preparation Example 2-3. Then, a solution of BS20 [in purified water/ethanol (3:7)] was obtained in the same manner as described in Preparation Example 6-1.

[Preparation Example 6-4]

(Preparation of polyaspartic acid derivative BS15/L10)

BS15/L10 was obtained in the same manner as described in Preparation Example 5-3. Then, a solution of BS15/L10 (in ethanol) was obtained in the same manner as described in Preparation Example 6-1.

[Preparation Example 6-5]

(Preparation of polyaspartic acid derivative BT)

BT was obtained in the same manner as described in Preparation Example 2-4. Then, a solution of BT [in purified water/ethanol (3:7)] was obtained in the same manner as described in Preparation Example 6-1.

[Example 6-1]

5 g of the solution of polyaspartic acid derivative BL25 obtained in Preparation Example 6-1 was diluted with ethanol to obtain a spray sample.

[Examples 6-2 to 6-5]

Spray samples were obtained in the same manner as described in Example 6-1, except that the type and amount of the amphoteric ion-containing resin used as the active ingredient were altered as shown in Table 14.

[Examples 6-6 and 6-7]

Spray samples were obtained in the same manner as described in Example 6-1, except that the amount of the amphoteric ion-containing resin used as the active ingredient was greatly varied as shown in Table 14.

[Comparative Example 6-1]

Gantrez ES-225 (an anionic polymer sold by GAF Corporation, U.S.A.), a currently used commercial product, was neutralized with aminomethylpropanol by 20% of the theoretical amount and then diluted with ethanol to obtain a spray sample.

[Comparative Example 6-2]

Amphomer (an amphoteric polymer sold by National Starch Co., U.S.A.), a currently used commercial product, was neutralized with aminomethylpropanol by 95% of the theoretical amount and then diluted with ethanol to obtain a spray sample.

[Comparative Example 6-3]

Yukaformer AM-75 (an amphoteric polymer sold by Mitsubishi Chemical Co., Ltd.), a currently used commercial product, was diluted with ethanol to obtain a spray sample.

The hairdressing resin compositions of Examples 6-1 to 6-7 and Comparative Examples 6-1 to 6-3 were evaluated according to the previously described procedures and the following procedures. The results thus obtained are shown in Table 14.

(1) Spray pattern

Each spray sample was charged into an accumulator type pump and sprayed once onto heat-sensitive paper from a distance of 30 cm. On the basis of the state of color development on the heat-sensitive paper, the resulting spray pattern was rated as follows:

o, the droplets of the spray were fine and evenly distributed;

Δ, the droplets of the spray were rather coarse and rather unevenly distributed in that the extent of the spray was rather limited and the density thereof was somewhat higher in the central region;

X, the droplets of the spray were coarse and unevenly distributed in that the extent of the spray was limited and the density thereof was higher in the central region.

(2) Clogging

Each spray sample was charged into an accumulator type pump and sprayed three times in a day. When the pump was allowed to stand for 3 days and sprayed again, the presence or absence of clogging was evaluated as follows:

o, the valve was not clogged;

X, the valve was clogged.

[Preparation Example 7-3]

(Preparation of polyaspartic acid derivative BS20)

BS20 was obtained in the same manner as described in Preparation Example 2-3.

[Preparation Example 7-4]

(Preparation of polyaspartic acid derivative BT)

BT was obtained in the same manner as described in Preparation Example 2-4.

[Example 7-1]

5 g of polyaspartic acid derivative BL25 obtained in Preparation Example 7-1 was dissolved in 92 g of a purified water/ethanol (1:1) solvent mixture. After the addition of 3 g of carbon black as a pigment, the resulting mixture was stirred and blended well to obtain a hair dye composition.

[Example 7-2]

2 g of polyaspartic acid derivative BL40 obtained in Preparation Example 7-2 was dissolved in 97 g of a purified

TABLE 14

Results of Evaluation in Examples 6-1 to 6-7 and Comparative Examples 6-1 to 6-3

| | Active ingredient | | Spray performance | | Film performance | | | Hairdressing performance | | | |
|---|---|---|---|---|---|---|---|---|---|---|---|
| | Type | wt. % | Pattern | Clogging | Washability | Smoothness | Hardness | Setting power | flaking | Gloss | Feel |
| Examples | | | | | | | | | | | |
| 6-1 | BL25 | 5 | O | O | O | O | O | Δ | O | O | O |
| 6-2 | BL40 | 3 | O | O | O | O | O | O | O | O | O |
| 6-3 | BS20 | 3 | O | O | O | O | O | O | O | O | O |
| 6-4 | BS15/L10 | 3 | O | O | O | O | O | O | O | O | O |
| 6-5 | BT | 9 | O | O | O | O | O | Δ | O | O | O |
| 6-6 | BL40 | 25 | Δ | Δ | Δ | O | O | O | × | O | Δ |
| 6-7 | BS15/L10 | 0.5 | O | O | O | O | O | × | O | Δ | O |
| Comparative Examples | | | | | | | | | | | |
| 6-1 | cantrez ES-25 | 3 | Δ | × | × | O | × | × | × | Δ | × |
| 6-2 | Amphomer | 3 | O | × | × | O | × | × | × | Δ | × |
| 6-3 | Yukaformer AM-75 | 3 | O | × | × | O | Δ | O | Δ | O | O |

[7] Examples Concerning Application to Hair Dye Compositions

[Preparation Example 7-1]

(Preparation of polyaspartic acid derivative BL25)

BL25 was obtained in the same manner as described in Preparation Example 2-1.

[Preparation Example 7-2]

(Preparation of polyaspartic acid derivative BL40)

BL40 was obtained in the same manner as described in Preparation Example 2-2.

water/ethanol (1:1) solvent mixture. After the addition of 1 g of carbon black as a pigment, the resulting mixture was stirred and blended well to obtain a hair dye composition.

[Example 7-3]

3 g of polyaspartic acid derivative BS20 obtained in Preparation Example 7-3 was dissolved in 97 g of a purified water/ethanol (1:1) solvent mixture. After the addition of 0.5 g of carbon black as a pigment, the resulting mixture was stirred and blended well to obtain a hair dye composition.

[Example 7-4]

10 g of polyaspartic acid derivative BT obtained in Preparation Example 7-4 was dissolved in 97 g of a purified water/ethanol (1:1) solvent mixture. After the addition of 1 g of carbon black as a pigment, the resulting mixture was stirred and blended well to obtain a hair dye composition.

[Comparative Example 7-1]

Instead of the polyaspartic acid derivatives, 7 g of commercially available Diahold (trade name of a product of Mitsubishi Chemical Co., Ltd.; a 50% ethanolic solution of an acrylic polymer) known as an anionic resin for use in hairdressings was dissolved in 93 g of a purified water/ethanol (1:1) solvent mixture. After the addition of 0.5 g of carbon black as a pigment, the resulting mixture was stirred and blended well to obtain a hair dye composition.

[Comparative Example 7-2]

Instead of the polyaspartic acid derivatives, 5.0 g of powdered polyvinyl pyrrolidone known as a nonionic resin for use in hairdressings was dissolved in 92 g of purified water. After the addition of 3 g of carbon black as a pigment, the resulting mixture was stirred and blended well to obtain a hair dye composition.

[Comparative Example 7-3]

Instead of the polyaspartic acid derivatives, 5 g of commercially available MERQUAT (trade name of a product of Merck & Co., Ltd.; a 40% aqueous solution of a polymer of diallyldimethylammonium chloride) known as a cationic resin for use in hairdressings was dissolved in 94 g of purified water. After the addition of 1 g of carbon black as a pigment, the resulting mixture was stirred and blended well to obtain a hair dye composition.

The hair dye compositions of Examples 7-1 to 7-4 and Comparative Examples 7-1 to 7-3 were evaluated according to the previously described procedures and the following procedures. The results thus obtained are shown in Tables 15 and 16.

(1) Dyeing properties and hair gloss

Hair dyed with each composition was curled in the same manner as described for the evaluation of curl retention. By observing the curled hair, its degree of dyeing and gloss were rated as follows:

○, the hair was dyed well and had a good gloss;
Δ, the hair was dyed well, but had a rather poor gloss;
X, the hair was not dyed well and had a poor gloss.

TABLE 16

Comparative Examples 7-1 to 7-3

| | Comparative Example | | 7-1 | 7-2 | 7-3 |
|---|---|---|---|---|---|
| Composition | (A) | Polyaspartic acid derivative (g) | HR-200 (7.0) | PVPK-30 (5.0) | MERQUAT (10.0) |
| | (B) | Pigment (g) | Carbon BL(0.5) | Carbon BL (3.0) | Carbon BL (1.0) |
| | (C) | Solvent (g) Purified water | 46.5 | 92.0 | 94.0 |
| | | Ethanol | 46.5 | 0 | 0 |
| Results | | Curl retention | Δ | × | × |
| | | Flaking | Δ | × | ○ |
| | | Gloss | × | × | × |
| Overall evaluation | | | × | × | × |

We claim:

1. A polymer containing, in the molecule, 1 mol % or more of at least one repeating unit selected from the group consisting of repeating units represented by the following formulas (1) and (2).

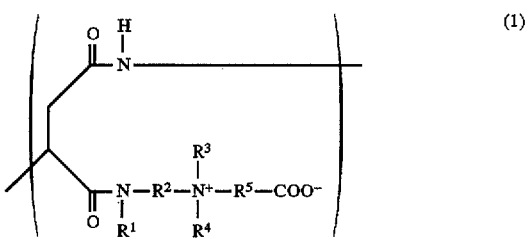

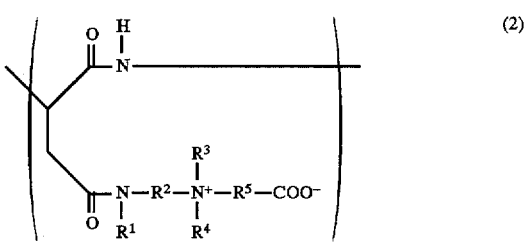

where $R^1$ is a hydrogen atom or a lower hydrocarbon radical of 1 to 6 carbon atoms, $R^2$ and $R^5$ are each independently a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom.

TABLE 15

| | Example | | 7-1 | 7-2 | 7-3 | 7-4 |
|---|---|---|---|---|---|---|
| Composition | (A) | Polyaspartic acid derivative (g) | BL25 (5.0) | BL40 (2.0) | BS20 (3.0) | BT (10.0) |
| | (B) | Pigment (g) | Carbon BL(3.0) | Carbon BL (1.0) | Carbon BL (0.5) | Carbon BL (1.0) |
| | (C) | Solvent (g) Purified water | 46.0 | 48.5 | 48.5 | 44.5 |
| | | Ethanol | 46.0 | 48.5 | 48.5 | 44.5 |
| Results | | Curl retention | ○ | ○ | ○ | Δ |
| | | Flaking | ○ | ○ | ○ | ○ |
| | | Gloss | ○ | ○ | ○ | ○ |
| Overall evaluation | | | ○ | ○ | ○ | ○ |

2. A polymer as claimed in claim 1 which further contains, in the molecule, 99 mol % or less of at least one repeating unit selected from the group consisting of repeating units represented by the following formulas (3) and (4).

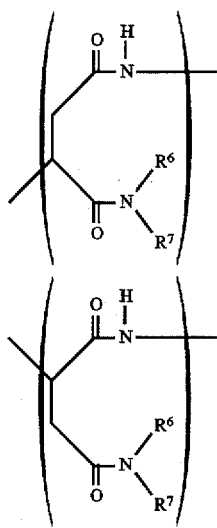
(3)

(4)

where $R^6$ and $R^7$ are each independently a hydrogen atom, or a saturated or unsaturated hydrocarbon radical of 1 to 24 carbon atoms in which $R^6$ and $R^7$ may be bonded together to form a six members ring containing nitrogen atom.

3. A polymer as claimed in claim 1 which further contains, in the molecule, 99 mol % or less of at least one repeating unit selected from the group consisting of repeating units represented by the following formulas (3) and (4), and the following formulas (5) to (9):

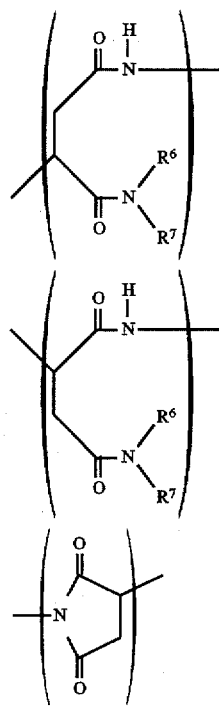
(3)

(4)

(5)

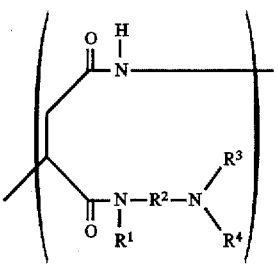
(6)

(7)

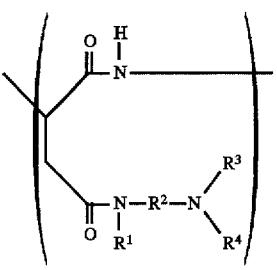

where $R^1$ is a hydrogen atom or a lower hydrocarbon radical of 1 to 6 carbon atoms, $R^2$ is a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom and where $R^6$ and $R^7$ are each independently a hydrogen atom, or a saturated or unsaturated hydrocarbon radical of 1 to 24 carbon atoms in which $R^6$ and $R^7$ may be bonded together to form a six members ring containing nitrogen atom;

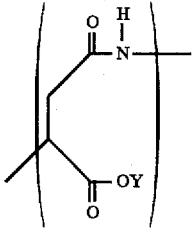
(8)

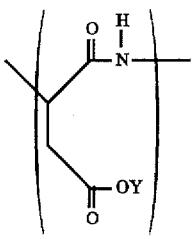
(9)

where Y is a hydrogen atom, an alkali metal atom or an alkaline earth metal atom.

4. A polymer as claimed in claim 1 which further contains, in the molecule, at least one repeating unit selected from the group consisting of repeating units represented by the following formulas (3) to (9), and the following formulas (10) and (11):

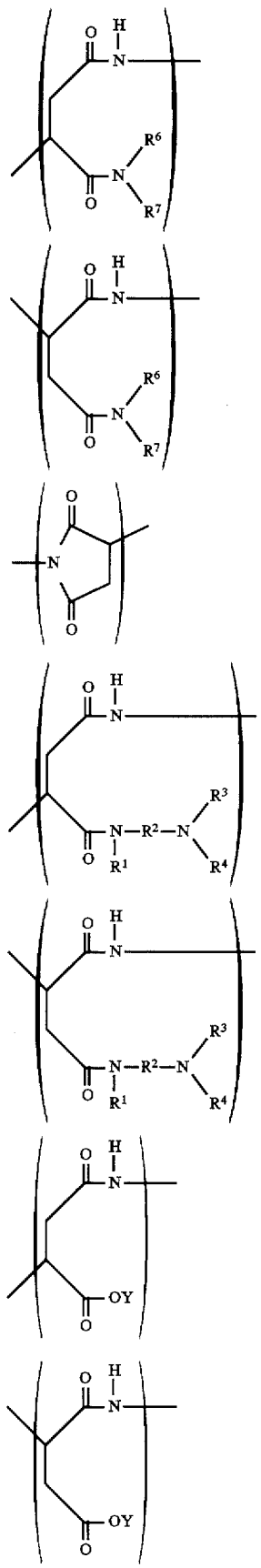
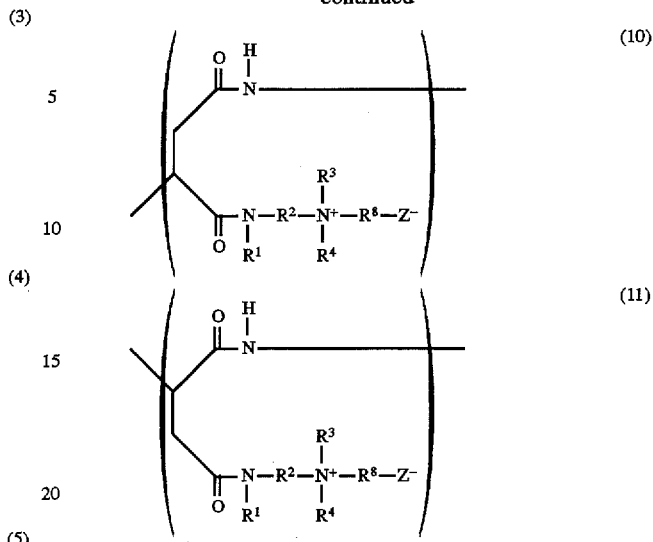

where $R^1$ is a hydrogen atom or a lower hydrocarbon radical of 1 to 6 carbon atoms, $R^2$ is a saturated or unsaturated hydrocarbon radical 1 to 24 carbon atoms, $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, $R^6$ and $R^7$ are each independently a hydrogen atom, or a saturated or unsaturated hydrocarbon radical or 1 to 24 carbon atoms in which $R^6$ and $R^7$ may be bonded together to form a six members ring containing nitrogen atom and $R^8$ is a hydrogen atom, or a saturated or unsaturated hydrocarbon radical of 1 to 24 carbon atoms, Y is a hydrogen atom, an alkali metal atom or an alkaline earth metal and $z^-$ is an anion derived from an organic or inorganic acid.

5. A polymer as claimed in claim 1 wherein $R^1$ is a hydrogen atom, $R^2$ is a saturated hydrocarbon radical of 1 to 5 carbon atoms, $R^5$ is a saturated hydrocarbon radical of 1 to 5 carbon atoms or a saturated or an unsaturated hydrocarbon radical of 12 or 18, and $R^3$ and $R^4$ are each independently a saturated hydrocarbon radical of 1 to 6 carbon atoms in formulas (1) and (2).

6. A polymer as claimed in claim 2 wherein $R^6$ and $R^7$ are each independently a hydrogen atom, or a saturated or unsaturated hydrocarbon radical of 4 to 18 carbon atoms in formulas (3) and (4).

7. A polymer as claimed in claim 3 wherein $R^1$ is a hydrogen atom, $R^2$ is a saturated hydrocarbon radical of 1 to 5 carbon atoms, and $R^3$ and $R^4$ are each independently a saturated hydrocarbon radical of 1 to 6 carbon atoms or a saturated or unsaturated hydrocarbon radical of 12 or 18 in formulas (6) and (7).

8. A polymer as claimed in claim 4 wherein $R^1$ is a hydrogen atom, $R^2$ is a saturated hydrocarbon radical of 1 to 5 carbon atoms, and $R^3$ and $R^4$ are each independently a saturated hydrocarbon radical of 1 to 6 carbon atoms, $R^8$ is a saturated hydrocarbon radical of 1 to 5 carbon atoms or a saturated or unsaturated hydrocarbon radical of 12 or 18 in formulas (10) and (11).

9. A polymer as claimed in claim 1 wherein the average number of all repeating units in the molecule is from 10 to 5,000.

10. A process for the preparation of polymer as claimed in claim 1, which comprises the steps of reacting polysuccinimide of formula (12)

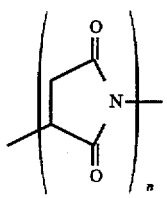

with at least one compound selected from the group consisting of amines of formula (13)

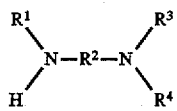

where $R^1$ is a hydrogen atom or a lower hydrocarbon radical of 1 to 6 carbon atoms, $R^2$ is a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, and salts thereof, and making the resulting product amphoteric by reaction with a halogenated fatty acid salt of formula (14)

$$L-R^5-COOM \qquad (14)$$

where L is a halogen atom, $R^5$ is a saturated or unsaturated hydrocarbon radical of 1 to 24 carbon atoms, and M is a hydrogen atom, an alkali metal atom or an alkaline earth metal atom.

11. A process for the preparation of polymer as claimed in claim 1, which comprises the steps of reacting polysuccinimide of formula (12)

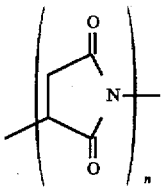

with at least one compound selected from the group consisting of amines containing amphoteric ion of formula (15),

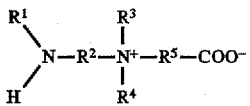

where $R^1$ is a hydrogen atom or a lower hydrocarbon radical of 1 to 6 carbon atoms, $R^2$ and $R^5$ are each independently a saturated or unsaturated hydrocarbon radical of 1 to 24 carbon atoms, and $R^3$ and $R^4$ are each independently a hydrogen atom, or a saturated or unsaturated hydrocarbon radical of 1 to 24 carbon atoms in which $R^3$ and $R^4$ may be bonded together to form a six members ring containing nitrogen atom, and salts thereof.

12. A process as claimed in claim 10 which comprises the steps of reacting polysuccinimide of formula (12) with at least one compound selected from the group consisting of amines of formula (16)

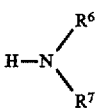

where $R^6$ and $R^7$ are each independently a hydrogen atom, or a saturated or unsaturated hydrocarbon radical of 1 to 24 carbon atoms in which $R^6$ and $R^7$ may bonded together to form a six members ring containing nitrogen atom, and salts thereof, and at least one compound selected from the group consisting of amines of formula (13) And salts thereof, and making the resulting product amphoteric by reaction with a halogenated fatty acid salt of formula (14).

13. A process as claimed in claim 12 which comprises the steps of reacting polysuccinimide of formula (12) with at least one compound selected from the group consisting of amines of formula (16) and salts thereof, and at least one compound selected from the group consisting of amines of formula (13) and salts thereof, and making the resulting product amphoteric and cationic by reaction with a halogenated fatty acid salt of formula (14), a halogenated alkyl and a halogenated ester of formula (17), $$L-R^8-COOR^9 \qquad (17)$$

where $R^8$ and $R^9$ are each independently a saturated or unsaturated hydrocarbon radical of 1 to 24 carbon atoms.

14. A process as claimed in claim 10 wherein $R^1$ is a hydrogen atom, $R^2$ is a saturated hydrocarbon radical of 1 to 5 carbon atoms, and $R^3$ and $R^4$ are each independently a saturated hydrocarbon radical of 1 to 6 carbon atoms in formula (13).

15. A process as claimed in claim 10 wherein $R^5$ is a saturated or unsaturated hydrocarbon radical of 1 to 18 carbon atoms in formula (14).

16. A process as claimed in claim 12 wherein $R^6$ and $R^7$ are each independently a saturated or unsaturated hydrocarbon radical of 4 to 18 carbon atoms in formula (16).

17. A hair-treating composition containing a polymer as claimed in claim 1.

18. A cosmetic composition containing a polymer as claimed in claim 1.

19. A gel-like hairdressing composition comprising (A) 0.1 to 20% by weight of a polymer as claimed in claim 1, (B) 0.1 to 10% by weight of a gel-forming base material, and (C) 70 to 99.8% by weight of a solvent consisting essentially of water and/or a lower alcohol of 1 to 6 carbon atoms.

20. A gel-like hairdressing composition comprising as claimed in claim 19 wherein the gel-forming base material is a partially or completely neutralized salt of a crosslinked carboxyvinyl polymer.

21. A hairdressing spray composition comprising (A) 0.1 to 20% by weight of a polymer as claimed in claim 1, (B) 10 to 99.8% by weight of a solvent, and (C) 10 to 75% by weight of a propellant.

22. A hairdressing resin composition comprising (A) 0.1 to 20% by weight of a polymer as claimed in claim 1, and (B) 80 to 99.9% by weight of a solvent.

23. A hair dye composition comprising (A) 0.1 to 20% by weight of a polymer as claimed in claim 1, (B) 0.1 to 10% by weight of a pigment, and (C) 70 to 99.8% by weight of a solvent consisting essentially of water and/or a lower alcohol of 1 to 6 carbon atoms.

* * * * *